(12) United States Patent
Sherman et al.

(10) Patent No.: US 6,600,029 B1
(45) Date of Patent: Jul. 29, 2003

(54) METABOLIC ENGINEERING OF POLYHYDROXYALKANOATE MONOMER SYNTHASES

(75) Inventors: David H. Sherman, St. Louis Park, MN (US); Mark D. Williams, St. Paul, MN (US); Yongquan Xue, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/091,609

(22) PCT Filed: Dec. 18, 1996

(86) PCT No.: PCT/US96/20119

§ 371 (c)(1),
(2), (4) Date: Jun. 19, 1998

(87) PCT Pub. No.: WO97/22711

PCT Pub. Date: Jun. 26, 1997

Related U.S. Application Data

(60) Provisional application No. 60/008,847, filed on Dec. 19, 1995.

(51) Int. Cl.⁷ ............................ C07H 21/04; C12P 7/52; C12P 7/44; C12P 7/62; C12N 15/63
(52) U.S. Cl. ...................... 536/23.2; 435/141; 435/142; 435/135; 435/320.1; 435/183; 435/146; 435/252.3; 435/252.33; 435/252.35; 435/325; 536/23.1
(58) Field of Search ................................ 435/141, 182, 435/142, 135, 146, 320.1, 325, 252.3, 252.33, 252.35; 536/23.2, 23.1

(56) References Cited

U.S. PATENT DOCUMENTS

| | | | |
|---|---|---|---|
| 4,874,748 A | 10/1989 | Katz et al. | 514/29 |
| 4,935,340 A | 6/1990 | Baltz et al. | 435/6 |
| 4,952,502 A | 8/1990 | Epp et al. | 435/76 |
| 5,063,155 A | 11/1991 | Cox et al. | 435/76 |
| 5,068,189 A | 11/1991 | Epp et al. | 435/183 |
| 5,098,837 A | 3/1992 | Beckmann et al. | 435/172.3 |
| 5,149,638 A | 9/1992 | Beckmann et al. | 435/76 |
| 5,149,639 A | 9/1992 | Katz et al. | 435/76 |
| 5,168,052 A | 12/1992 | Cox et al. | 435/72 |
| 5,229,279 A | 7/1993 | Peoples et al. | 435/135 |
| 5,245,023 A | 9/1993 | Peoples et al. | 536/23.2 |
| 5,250,430 A | 10/1993 | Peoples et al. | 435/232 |
| 5,364,778 A | 11/1994 | Byrom | 435/135 |
| 5,371,002 A | 12/1994 | Dennis et al. | 435/142 |
| 5,387,513 A | 2/1995 | Anderson et al. | 435/135 |
| 5,480,794 A | 1/1996 | Peoples et al. | 435/232 |
| 5,502,273 A | 3/1996 | Bright et al. | 800/205 |
| 5,512,669 A | 4/1996 | Peoples et al. | 536/23.2 |
| 5,514,544 A | 5/1996 | Rao et al. | 435/6 |
| 5,534,432 A | 7/1996 | Peoples et al. | 435/240.4 |
| 5,545,553 A | 8/1996 | Gotschlich | 435/252.33 |
| 5,610,041 A | 3/1997 | Somerville et al. | 435/135 |
| 5,661,026 A | 8/1997 | Peoples et al. | 435/252.3 |
| 5,663,063 A | 9/1997 | Peoples et al. | 435/135 |
| 5,672,491 A | 9/1997 | Khosla et al. | 435/148 |
| 5,672,497 A | 9/1997 | Cox et al. | 435/320.1 |
| 5,702,717 A | 12/1997 | Cha et al. | 424/425 |
| 5,712,146 A * | 1/1998 | Khosla et al. | 435/252.35 |
| 5,716,849 A | 2/1998 | Ligon et al. | 435/419 |
| 5,744,350 A | 4/1998 | Vinci et al. | 435/254.11 |
| 5,798,235 A | 8/1998 | Peoples et al. | 435/135 |
| 5,824,513 A | 10/1998 | Katz et al. | 435/76 |
| 5,830,750 A | 11/1998 | Khosla et al. | 435/252.35 |
| 5,843,718 A | 12/1998 | Khosla et al. | 435/69.1 |
| 5,962,290 A | 10/1999 | Khosla et al. | 435/183 |
| 6,022,731 A | 2/2000 | Khosla et al. | 435/252.35 |
| 6,033,883 A | 3/2000 | Barr et al. | 435/148 |
| 6,077,696 A | 6/2000 | Khosla et al. | 435/135 |

FOREIGN PATENT DOCUMENTS

| | | | |
|---|---|---|---|
| CA | 2107505 | 4/1994 | C12N/15/11 |
| EP | 0 238 323 | 9/1987 | C12N/15/00 |
| EP | 0 361 905 | 4/1990 | C12N/15/52 |
| EP | 0 468 220 | 1/1992 | C12N/15/52 |
| EP | 0 791 655 | 8/1997 | C12N/15/52 |
| EP | 0 791 656 | 8/1997 | C12N/15/52 |
| FR | 2 696 189 | 4/1994 | C12N/15/31 |
| JP | 6261765 | 9/1994 | C12N/15/54 |
| JP | 10094395 | 4/1998 | C12N/15/09 |
| TW | 202481 | 3/1993 | C12N/15/10 |
| WO | 87/03907 | 7/1987 | C12N/15/00 |
| WO | WO-91/00917 | 1/1991 | C12P/7/62 |
| WO | 92/16629 | 10/1992 | C12N/15/31 |
| WO | 92/19747 | 11/1992 | C12N/15/82 |
| WO | 93/02187 | 2/1993 | C12N/15/00 |
| WO | 93/13663 | 7/1993 | A01N/43/22 |
| WO | 93/23545 | 11/1993 | C12N/15/52 |
| WO | WO-94/11519 | 5/1994 | C12N/15/82 |
| WO | 95/08548 | 3/1995 | C07D/311/78 |
| WO | 96/01901 | 1/1996 | C12N/15/52 |
| WO | 96/10084 | 4/1996 | C12N/15/52 |
| WO | 96/40968 | 12/1996 | C12P/7/26 |
| WO | 97/02358 | 1/1997 | C12P/19/62 |
| WO | 98/00557 | 1/1998 | C12N/15/82 |
| WO | 98/01546 | 1/1998 | C12N/15/00 |
| WO | 98/04713 | 2/1998 | C12N/15/52 |

OTHER PUBLICATIONS

Cortes et al., An Unusually Large Multifunctional Polypeptide in the Erythromycin–Producing Polyketide Synthase of *Saccharopolyspora erythraea*. Nature 348: 176–178 (1990).*

(List continued on next page.)

*Primary Examiner*—Karen Cochrane Carlson
*Assistant Examiner*—Chih-Min Kam
(74) *Attorney, Agent, or Firm*—Schwegman, Lundberg, Woessner & Kluth, P.A.

(57) ABSTRACT

A novel pathway for the synthesis of polyhydroxyalkanoate is provided. A method of synthesizing a recombinant polyhydroxyalkanoate monomer synthase is also provided. These recombinant polyhydroxyalknoate synthases are derived from multifunctional fatty acid synthases or polyketide synthases and generate hydroxyacyl acids capable of polymerization by a polyhydroxyalknoate synthase.

44 Claims, 33 Drawing Sheets

OTHER PUBLICATIONS

Bevitt, D.J., et al., "6–Deoxyerythronolide–B synthase 2 from *Saccharopolyspora erythraea*; cloning of the structural gene, sequence analysis and inferred domain structure of the multifunctional enzyme", *European Journal of Biochemistry*, vol. 204, No. 1, pp. 39–49, (Feb. 2, 1992).

Donadio, S., et al., "Organization of the enzymatic domains in the multifunctional polyketide synthase involved in erythromycin formation in saccharopolyspora erythraea", *Gene*, vol. III, No. 1, pp. 51–60, (Feb. 1, 1992).

Fraser, M.H., "The Baculovirus–Infected Insect Cell as a Eukaryotic Gene Expression System", *Dept. of Biological Sciences, University of Notre Dame, Indiana*, 31–172, (1992).

Han, L., et al., "Cloning and characterization of polyketide synthase genes for jadomycin B biosynthesis in *Streptomyces venezuelae*", *Microbiology*, pp. 3379–3389, (Dec. 1994).

Joshi, A.K., et al., "Construction, Expression and Characterization of a Mutated Animal Fatty Acid Synthase Deficient in the Dehydrase Function", *The Journal of Biological Chemistry*, vol. 268, No. 30, pp. 22508–22513, (Oct. 25, 1993).

Adler, T., "Plants: The New Plastics Makers", *Science News of the Week*, 146(26–27), 420 (1994).

Andersen, J.F., et al., "Characterization of *Saccharopolyspora erythraea* Cytochrome P–450 Genes and Enzymes, Including 6–Deoxyerythronolide B Hydroxylase", *Journal of Bacteriology*, 174, 725–735 (1992).

Anderson, A.J., et al., "Occurrence, Metabolism, Metabolic Role, and Industrial Uses of Bacterial Polyhydroxyalkanoates", *Microbiological Review*, 54(4), 450–472 (1990).

Brandl, H., et al., "Plastics from Bacteria and for Bacteria: Poly (β–hydroxy–alkanoates) as Natural, Biocompatible, and Biodegradable Polyesters", *Advances in Biochemical Engineering Biotechnology*, 41, 77–93 (1990).

Byrom, D., "Polymer synthesis by micro–organisms: technology and economics", *Tibtech*, 5, 246–250 (1987).

Cortes, J., et al., "Repositioning of a Domain in a Modular Polyketide Synthase to Promote Specific Chain Cleavage", *Science*, 268, 1487–1489 (1995).

Donadio, S., et al., "An erythromycin analog produced by reprogramming of polyketide synthesis", *Proceedings of the National Academy of Sciences*, 90, 7119–7123 (1993).

Donadio, S., et al., "Modular Organization of Genes Required for Complex Polyketide Biosynthesis", *Science*, 252, 675–679 (1991).

Fu, H., et al., "Antibiotic activity of polyketide products derived from combinatorial biosynthesis: Implications for directed evolution", *Molecular Diversity*, 1(2), 121–124 (1995).

Hopwood, et al., "Genetic Manipulation of Streptomyces: A Laboratory Manual", 77–78, 292–293, 214–224 (1985).

Hopwood, D.A., "Antibiotics: Opportunities for Genetic Manipulation", *Philosophical Transactions of the Royal Society of London*, 324, 549–562 (1989).

Hopwood, D.A., et al., "Molecular Genetics of Polyketides and its Comparison to Fatty Acid Biosynthesis", *Annu. Rev. Genet.*, 24, 37–66 (1990).

Joshi, A.K., et al., "Construction of a cDNA encoding the multifunctional animal fatty acid synthase and expression in *Spodoptera frugiperda* cells using baculoviral vectors", *Biochem. J.*, 296, 143–149 (1993).

Kao, C.M., et al., "Engineered Biosynthesis of a Complete Macrolactone in a Heterologous Host", *Science*, 265, 509–512 (1994).

Kao, C.M., et al., "Manipulation of Macrolide Ring Size by Directed Mutagenesis of a Modular Polyketide Synthase", *J. Am. Chem. Soc.*, 117, 9105–9106 (1995).

Kealey, J.T., et al., "Production of a Polyketide Natural Product in Nonpolyketide–Producing Prokaryotic and Eukaryotic Hosts", *Proc. Natl. Acad. Sci. USA*, 95, 505–509 (1998).

McDaniel, R., et al., "Rational Design of Aromatic Polyketide Natural Products by Recombinant Assembly of Enzymatic Subunits", *Nature*, 375, 549–554 (1995).

Pan, S., et al., "The role of NAD(P)H:Quinone Oxidoreductase in Mitomycin C–and Porfiromycin–Resistant HCT 116 Human Colon–Cancer Cells", *Cancer Chemother. Pharmacol.*, 31, 23–31 (1992).

Peoples, O.P., et al., "Poly–β–hydroxybutyrate Biosynthesis in *Alcaligenes eutrophus* H16 characterization of the genes encoding β–Ketothiolase and acetoacetyl–CoA", *The Journal of Biological Chemistry*, 264(26), 15293–15297 (1989).

Poirier, Y., et al., "Polyhydroxybutyrate, a Biodegradable Thermoplastic, Produced in Transgenic Plants", *Science*, 256, 520–523 (1992).

Poirier, Y., et al., "Production of Polyhydroxyalkanoates, a Family of Biodegradable Plastics and Elastomers, in Bacteria Plants", *Bio/Technology*, 13, 142–150 (1995).

Schneider, A., et al., "Genetic Evidence for a Role of Thioesterase Domains, Integrated in or Associated with Peptide Synthetases, in Non–Ribosomal Peptide Biosythesis in *Bacillus subtili*", *Arch. Microbiol.*, 169, 404–410 (1998).

Schwecke, T., et al., "The Biosynthetic Gene Cluster for the Polyketide Immunosuppressant Rapamycin", *Proc. Natl. Acad. Sci. USA*, 92, 7839–7843 (1995).

Tsoi, C.J., et al., "Combinatorial Biosynthesis of 'Unnatural' Natural Products: The Polyketide Example", *Chemistry and Biology*, 2, 355–362 (1995).

Verdine, G.L., et al., "The Combinatorial Chemistry of Nature", *Nature*, 384, 11–13 (1996).

Witt, D., et al., "Unification of the Genera Streptoverticillum and Streptomyces, and Amendation of Streptomyces Waksman and Henrici 1943, 339", *System. Appl. Microbiol.*, 13, 361–371 (1990).

Eggink, G.,et al. ,"The Role of Fatty Acid Biosynthesis and Degradation in the Supply of Substrates for Poly(3–hydroxyalkanoate) Formation in *Pseudomonas putida*", *FEMS Microbiology Reviews*, 103, (1992), 159–164.

Poirier, Y.,et al. ,"Progress Toward Biologically Produced Biodegradable Thermoplastics", *Advanced Materials*, 5, (1993),30–36.

Williams, M.D. ,et al. ,"Production of a Polyhydroxyalkanoate Biopolymer in Insect Cells with a Modified Eucaryotic Fatty Acid Synthase", *Applied and Environmental Microbiology*, 62, (Jul., 1996),2540–2546.

* cited by examiner

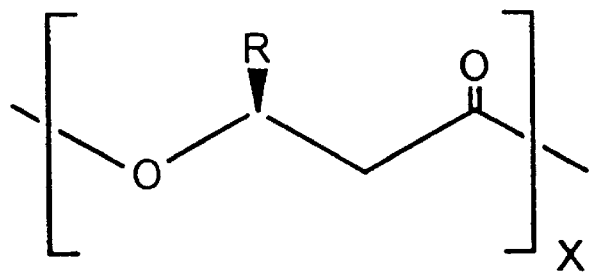

| R-group | Monomer | Abbreviation |
|---|---|---|
| methyl | 3-hydroxybutyrate | (3HB) |
| ethyl | 3-hydroxyvalerate | (3HV) |
| propyl | 3-hydroxycaproate | (3HC) |
| butyl | 3-hydroxyheptanoate | (3HH) |
| pentyl | 3-hydroxyoctanoate | (3HO) |
| hexyl | 3-hydroxynonanoate | (3HN) |
| heptyl | 3-hydroxydecanoate | (3HD) |
| octyl | 3-hydroxyundecanoate | (3HUD) |
| nonyl | 3-hydroxydodecanoate | (3HDD) |

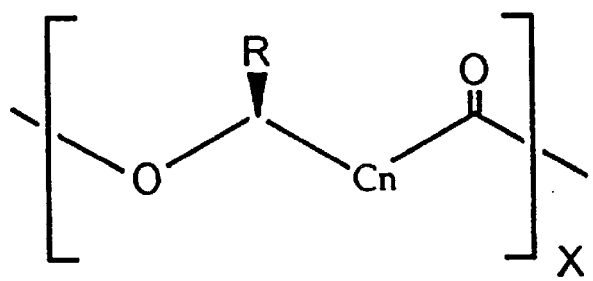

n = 1  3-hydroxyacyl monomer
n = 2  4-hydroxyacyl monomer
n = 3  5-hydroxyacyl monomer

FIG. 2

| N-terminal sequence determined for PHA synthase |
|---|
|     1          10               20    25 |
| a    MATGKGAAASTQEGKSQPFKVTPGP— |
| b            AAASTQEGKSQPFKVTPGP— |
| c                 STQEGKSQPFKVTPGP— |

FIG. 8

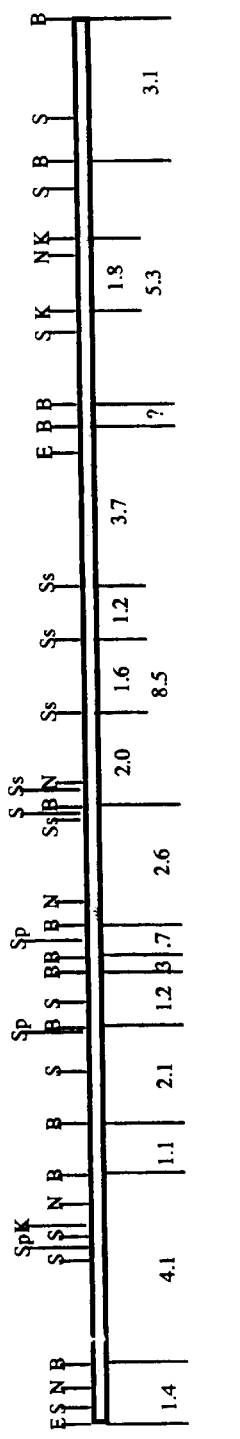
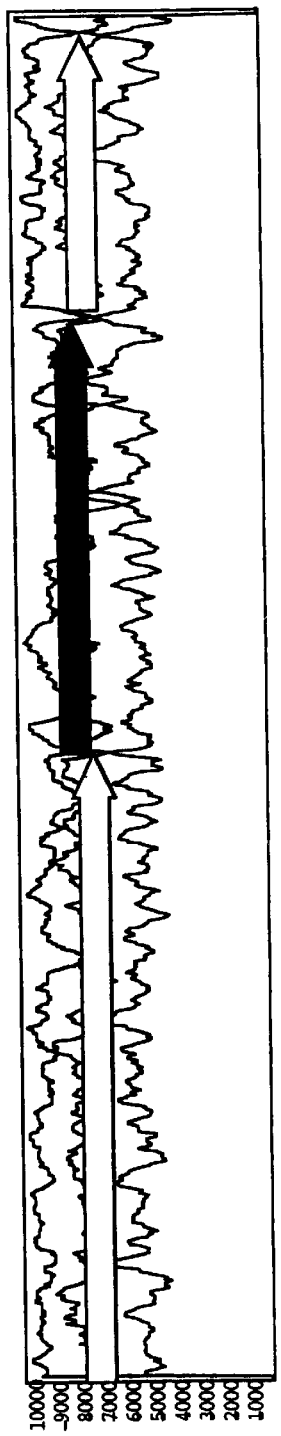
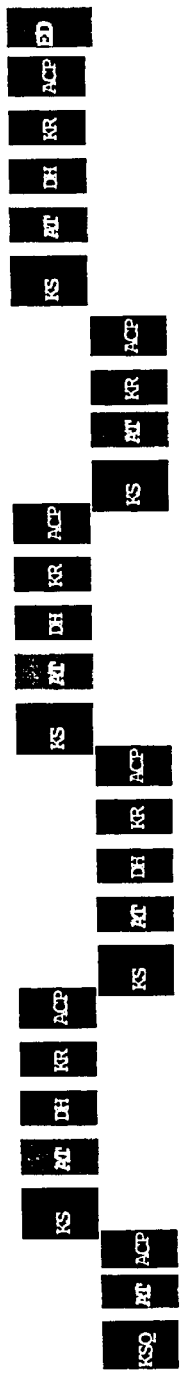
FIG. 19

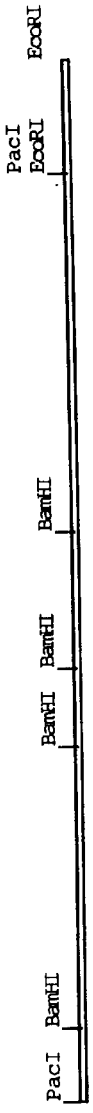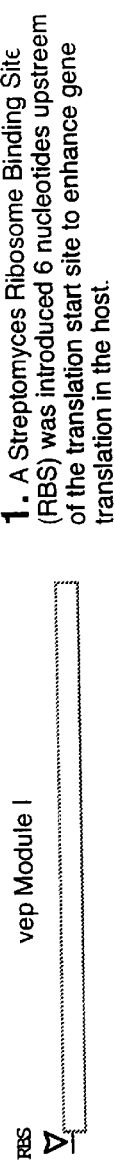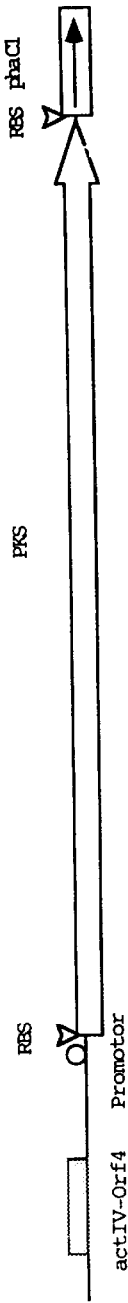
FIG. 22

```
  1 TTAATTAAGGAGGACCATC ATG AAC GAG GCC ATC GCC GTC GTC GGC ATG TCC TGC CGC CTG CCG   64
  1                     M   N   E   A   I   A   V   V   G   M   S   C   R   L   P    15

65 AAG GCC TCG AAC CCG GCC GCC TTC TGG GAG CTG CTG CGG AAC GGG GAG AGC GCC GTC ACC  124
 16 K   A   S   N   P   A   A   F   W   E   L   L   R   N   G   E   S   A   V   T    35

125 GAC GTG CCC TCC GGC CGG TGG ACG TCG GTG CTC GGG GGA GCG GAC GCC GAG GAG CCG GCG  184
 36 D   V   P   S   G   R   W   T   S   V   L   G   G   A   D   A   E   E   P   A    55

185 GAG TCC GGT GTC CGC CGG GGC GGC TTC CTC GAC TCC CTC GAC CTC TTC GAC GCG GCC TTC  244
 56 E   S   G   V   R   R   G   G   F   L   D   S   L   D   L   F   D   A   A   F    75

245 TTC GGA ATC TCG CCC CGT GAG GCC GCC GCC ATG GAC CCG CAG CAG CGA CTG GTC CTC GAA  304
 76 F   G   I   S   P   R   E   A   A   A   M   D   P   Q   Q   R   L   V   L   E    95

305 CTC GCC TGG GAG GCG CTG GAG GAC GCC GGA ATC GTC CCC GGC ACC CTC GCC GGA AGC CGC  364
 96 L   A   W   E   A   L   E   D   A   G   I   V   P   G   T   L   A   G   S   R   115

365 ACC GCC GTC TTC GTC GGC ACC CTG CGG GAC GAC TAC ACG AGC CTC CTC TAC CAG CAC GGC  424
116 T   A   V   F   V   G   T   L   R   D   D   Y   T   S   L   L   Y   Q   H   G   135

425 GAG CAG GCC ATC ACC CAG CAC ACC ATG GCG GGC GTG AAC CGG GGC GTC ATC GCC AAC CGC  484
136 E   Q   A   I   T   Q   H   T   M   A   G   V   N   R   G   V   I   A   N   R   155

485 GTC TCG TAC CAC CTC GGC CTG CAG GGC CCG AGC CTC ACC GTC GAC GCC GCG CAG TCG TCC  544
156 V   S   Y   H   L   G   L   Q   G   P   S   L   T   V   D   A   A   Q   S   S   175

545 TCG CTC GTC GCC GTG CAC CTG GCC TGC GAG TCC CTG CGC GCC GGG GAG TCC ACG ACG GCG  604
176 S   L   V   A   V   H   L   A   C   E   S   L   R   A   G   E   S   T   T   A   195

605 CTC GTC GCC GGC GTG AAC CTC AAC ATC CTC GCG GAG AGC GCC GTG ACG GAG GAG CGC TTC  664
196 L   V   A   G   V   N   L   N   I   L   A   E   S   A   V   T   E   E   R   F   215

665 GGT GGA CTC TCC CCG GAC GGC ACC GCC TAC ACC TTC GAC GCG CGG GCC AAC GGA TTC GTC  724
216 G   G   L   S   P   D   G   T   A   Y   T   F   D   A   R   A   N   G   F   V   235

725 CGG GGC GAG GGC GGC GGA GTC GTC GTA CTC AAG CCG CTC TCC CGC GCC CTC GCC GAC GGC  784
236 R   G   E   G   G   G   V   V   V   L   K   P   L   S   R   A   L   A   D   G   255

785 GAC CGT GTC CAC GGC GTC ATC CGC GCC AGC GCC GTC AAC AAC GAC GGA GCC ACC CCG GGT  844
256 D   R   V   H   G   V   I   R   A   S   A   V   N   N   D   G   A   T   P   G   275

845 CTC ACC GTG CCC AGC AGG GCC GCC CAG GAG AAG GTG CTG CGC GAG GCG TAC CGG AAG GCG  904
276 L   T   V   P   S   R   A   A   Q   E   K   V   L   R   E   A   Y   R   K   A   295

905 GCC CTG GAC CCG TCC GCC GTC CAG TAC GTC GAA CTC CAC GGC ACC GGA ACC CCC GTC GGC  964
296 A   L   D   P   S   A   V   Q   Y   V   E   L   H   G   T   G   T   P   V   G   315

965 GAC CCC ATC GAG GCC GCC GCG CTC GGC GCC GTC CTC GGC TCG GCG CGC CCC GCG GAC GAA 1024
316 D   P   I   E   A   A   A   L   G   A   V   L   G   S   A   R   P   A   D   E   335

1025 CCC CTG CTC GTC GGC TCG GCC AAG ACG AAC GTC GGG CAC CTC GAA GGC GCC GCC GGC ATC 1084
336  P   L   L   V   G   S   A   K   T   N   V   G   H   L   E   G   A   A   G   I   355

1085 GTC GGC CTC ATC AAG ACG CTC CTC GCG CTC GGC CGG CGG ATC CCG GCG AGC CTC AAC     1144
356  V   G   L   I   K   T   L   L   A   L   G   R   R   I   P   A   S   L   N     375

1145 TTC CGT ACG CCC CAC CCG GAC ATC CCG CTC GAC ACC CTC GGG CTC GAC GTG CCC GAC GGC 1204
376  F   R   T   P   H   P   D   I   P   L   D   T   L   G   L   D   V   P   D   G   395

1205 CTG CGG GAG TGG CCG CAC CCG GAC CGC GAA CTC CTC GCC GGC GTC AGC TCG TTC GGC ATG 1264
396  L   R   E   W   P   H   P   D   R   E   L   L   A   G   V   S   S   F   G   M   415

1265 GGC GGC ACC AAC GCC CAC GTC GTC CTC AGC GAA GGC CCC GCC CAG GGC GGC GAG CAG CCC 1324
416  G   G   T   N   A   H   V   V   L   S   E   G   P   A   Q   G   G   E   Q   P   435

1325 GGC ATC GAT GAG GAG ACC CCC GTC GAC AGC GGG GCC GCA CTG CCC TTC GTC GTC ACC GGC 1384
436  G   I   D   E   E   T   P   V   D   S   G   A   A   L   P   F   V   V   T   G   455

1385 CGC GGC GGC GAG GCC CTG CGC GCC CAG GCC CGG CGC CTG CAC GAG GCC GTC GAA GCG GAC 1444
456  R   G   G   E   A   L   R   A   Q   A   R   R   L   H   E   A   V   E   A   D   475
```

FIG. 23A

```
1445 CCG GAG CTC GCG CCC GCC GCA CTC GCC CGG TCG CTG GTC ACC ACC CGT ACG GTC TTC ACG 1504
476  P   E   L   A   P   A   A   L   A   R   S   L   V   T   T   R   T   V   F   T  495

1505 CAC CGG TCG GTC GTC CTC GCC CCG GAC CGC GCC CGC CTC CTC GAC GGC CTC GGC GCC CTC 1564
496  H   R   S   V   V   L   A   P   D   R   A   R   L   L   D   G   L   G   A   L  515

1565 GCC GCC GGG ACG CCC GCG CCC GGC GTG GTC ACC GGC ACC CCC GCC CCC GGG CGC CTC GCC 1624
516  A   A   G   T   P   A   P   G   V   V   T   G   T   P   A   P   G   R   L   A  535

1625 GTC CTG TTC AGC GGC CAG GGT GCC CAA CGT ACG GGC ATG GGC ATG GAG TTG TAC GCC GCC 1684
536  V   L   F   S   G   Q   G   A   Q   R   T   G   M   G   M   E   L   Y   A   A  555

1685 CAC CCC GCC TTC GCG ACG GCC TTC GAC GCC GTC GCC GCC GAA CTG GAC CCC CTC CTC GAC 1744
556  H   P   A   F   A   T   A   F   D   A   V   A   A   E   L   D   P   L   L   D  575

1745 CGG CCC CTC GCC GAA CTC GTC GCG GCG GGC GAC ACC CTC GAC CGC ACC GTC CAC ACA CAG 1804
576  R   P   L   A   E   L   V   A   A   G   D   T   L   D   R   T   V   H   T   Q  595

1805 CCC GCG CTC TTC GCC GTG GAG GTC GCC CTC CAC CGC CTC GTC GAG TCC TGG GGC GTC ACG 1864
596  P   A   L   F   A   V   E   V   A   L   H   R   L   V   E   S   W   G   V   T  615

1865 CCC GAC CTG CTC GCC GGC CAC TCC GTC GGC GAG ATC AGC GCC GCC CAC GTC GCC GGG GTC 1924
616  P   D   L   L   A   G   H   S   V   G   E   I   S   A   A   H   V   A   G   V  635

1925 CTG TCG CTG CGC GAC GCC GCC CGC CTC GTC GCG GCG CGC GGC CGC CTC ATG CAG GCG CTC 1984
636  L   S   L   R   D   A   A   R   L   V   A   A   R   G   R   L   M   Q   A   L  655

1985 CCC GAG GGC GGC GCG ATG GTC GCG GTC GAG GCG AGC GAG GAG GAA GTG CTT CCG CAC CTC 2044
656  P   E   G   G   A   M   V   A   V   E   A   S   E   E   V   L   P   H   L  675

2045 GCG GGA CGC GAG CGG GAG CTC TCC CTC GCG GCC GTG AAC GGC CCC CGC GCG GTC GTC CTC 2104
676  A   G   R   E   R   E   L   S   L   A   A   V   N   G   P   R   A   V   V   L  695

2105 GCG GGC GCC GAG CGC GCC GTC CTC GAC GTC GCC GAG CTG CTG CGC GAA CAG GGC CGC CGG 2164
696  A   G   A   E   R   A   V   L   D   V   A   E   L   L   R   E   Q   G   R   R  715

2165 ACG AAG CGG CTC AGC GTC TCG CAC GCC TTC CAC TCG CCG CTC ATG GAG CCG ATG CTC GAC 2224
716  T   K   R   L   S   V   S   H   A   F   H   S   P   L   M   E   P   M   L   D  735

2225 GAC TTC CGC CGG GTC GTC GAA GAG CTG GAC TTC CAG GAG CCC CGC GTC GAC GTC GTG TCC 2284
736  D   F   R   R   V   V   E   E   L   D   F   Q   E   P   R   V   D   V   V   S  755

2285 ACG GTG ACG GGC CTG CCT GTC ACA GCG GGC CAA TGG ACC GAT CCC GAG TAC TGG GTG GAC 2344
756  T   V   T   G   L   P   V   T   A   G   Q   W   T   D   P   E   Y   W   V   D  775

2345 CAG GTC CGC AGG CCC GTA CGC TTC CTC GAC GCC GTA CGC ACC CTG GAG GAA TCG GGC GCC 2404
776  Q   V   R   R   P   V   R   F   L   D   A   V   R   T   L   E   E   S   G   A  795

2405 GAC ACC TTC CTG GAG CTC GGT CCC GAC GGG GTC TGC TCC GCG ATG GCG GCG GAC TCC GTA 2464
796  D   T   F   L   E   L   G   P   D   G   V   C   S   A   M   A   A   D   S   V  815

2465 CGC GAC CAG GAG GCC GCC ACG GCG GTC TCC GCC CTG CGC AAG GGC CGC CCG GAG CCC CAG 2524
816  R   D   Q   E   A   A   T   A   V   S   A   L   R   K   G   R   P   E   P   Q  835

2525 TCG CTG CTC GCC GCA CTC ACC ACC GTC TTC GTC CGG GGC CAC GAC GTC GAC TGG ACC GCC 2584
836  S   L   L   A   A   L   T   T   V   F   V   R   G   H   D   V   D   W   T   A  855

2585 GCG CAC GGG AGC ACC GGC ACG GTC AGG GTG CCC CTG CCG ACC TAC GCC TTC CAG CGC GAA 2644
856  A   H   G   S   T   G   T   V   R   V   P   L   P   T   Y   A   F   Q   R   E  875

2645 CGC CAC TGG TTC GAC GGC GCC GCG CGA ACG CCG GCC CCG CTC ACG GCG GGC CGA TCG GGC 2704
876  R   H   W   F   D   G   A   A   R   T   A   A   P   L   T   A   G   R   S   G  895

2705 ACC GGT GCG GGC ACC GGC CCG GCC GCG GGT GTG ACG TCG GGC GAG GGC GAG GGC GAG GGC 2764
896  T   G   A   G   T   G   P   A   A   G   V   T   S   G   E   G   E   G   E   G  915

2765 GAG GGC GCG GGT GCG GGT GGC GGT GAT CGG CCG GCT CGC CAC GAG ACG ACC GAG CGC GTG 2824
916  E   G   A   G   A   G   G   G   D   R   P   A   R   H   E   T   T   E   R   V  935

2825 CGC GCA CAC GTC GCC GCC GTC CTC GAG TAC GAC GAC CCG ACC CGC GTC GAA CTC GGC CTC 2884
936  R   A   H   V   A   A   V   L   E   Y   D   D   P   T   R   V   E   L   G   L  955

2885 ACC TTC AAG GAG CTG GGC TTC GAC TCC CTC ATG TCC GTC GAG CTG CGG AAC GCG CTC GTC 2944
956  T   F   K   E   L   G   F   D   S   L   M   S   V   E   L   R   N   A   L   V  975

2945 GAC GAC ACG GGA CTG CGC CTG CCC AGC GGA CTG CTC TTC GAC CAC CCG ACG CCG CGC GCC 3004
976  D   D   T   G   L   R   L   P   S   G   L   L   F   D   H   P   T   P   R   A  995
```

FIG. 23B

```
3005 CTC GCC GCC CAC CTG GGC GAC CTG CTC ACC GGC GGC AGC GGC GAG ACC GGA TCG GCC GAC 3064
 996 L   A   A   H   L   G   D   L   L   T   G   G   S   G   E   T   G   S   A   D  1015

3065 GGG ATA CCG CCC GCG ACC CCG GCG GAC ACC ACC GCC GAG CCC ATC GCG ATC ATC GGC ATG 3124
1016 G   I   P   P   A   T   P   A   D   T   T   A   E   P   I   A   I   I   G   M  1035

3125 GCC TGC CGC TAC CCC GGC GGC GTC ACC TCC CCC GAG GAC CTG TGG CGG CTC GTC GCC GAG 3184
1036 A   C   R   Y   P   G   G   V   T   S   P   E   D   L   W   R   L   V   A   E  1055

3185 GGG CGC GAC GCC GTC TCG GGG CTG CCC ACC GAC CGC GGC TGG GAC GAG GAC CTC TTC GAC 3244
1056 G   R   D   A   V   S   G   L   P   T   D   R   G   W   D   E   D   L   F   D  1075

3245 GCC GAC CCC GAC CGC AGC GGC AAG AGC TCG GTC CGC GAG GGC GGA TTC CTG CAC GAC GCC 3304
1076 A   D   P   D   R   S   G   K   S   S   V   R   E   G   G   F   L   H   D   A  1095

3305 GCC CTG TTC GAC GCC GGC TTC TTC GGG ATA TCG CCC CGC GAG GCC CTC GGC ATG GAC CCG 3364
1096 A   L   F   D   A   G   F   F   G   I   S   P   R   E   A   L   G   M   D   P  1115

3365 CAG CAG CGG CTG CTC CTG GAG ACG GCA TGG GAG GCC GTG GAG CGC GCA GGG CTC GAC CCC 3424
1116 Q   Q   R   L   L   L   E   T   A   W   E   A   V   E   R   A   G   L   D   P  1135

3425 GAA GGC CTC AAG GGC AGC CGG ACG GCC GTC TTC GTC GGC GCC ACC GCC CTG GAC TAC GGC 3484
1136 E   G   L   K   G   S   R   T   A   V   F   V   G   A   T   A   L   D   Y   G  1155

3485 CCG CGC ATG CAC GAC GGC GCC GAG GGC GTC GAG GGC CAC CTC CTG ACC GGG ACC ACG CCC 3544
1156 P   R   M   H   D   G   A   E   G   V   E   G   H   L   L   T   G   T   T   P  1175

3545 AGC GTG ATG TCG GGC CGC ATC GCC TAC CAG CTC GGC CTC ACC GGT CCT GCG GTC ACC GTC 3604
1176 S   V   M   S   G   R   I   A   Y   Q   L   G   L   T   G   P   A   V   T   V  1195

3605 GAC ACG GCC TGC TCG TCC TCG CTC GTC GCG CTG CAC CTG GCC GTC CGT TCG CTG CGG CAG 3664
1196 D   T   A   C   S   S   S   L   V   A   L   H   L   A   V   R   S   L   R   Q  1215

3665 GGC GAG TCG AGC CTC GCG CTC GCC GGC GGA GCG ACC GTC ATG TCG ACA CCG GGC ATG TTC 3724
1216 G   E   S   S   L   A   L   A   G   G   A   T   V   M   S   T   P   G   M   F  1235

3725 GTC GAG TTC TCG CGG CAG CGC GGC CTC GCC GCC GAC GGC CGC TCC AAG GCC TTC TCC GAC 3784
1236 V   E   F   S   R   Q   R   G   L   A   A   D   G   R   S   K   A   F   S   D  1255

3785 TCC GCC GAC GGC ACC TCC TGG GCC GAG GGC GTC GGC CTC CTC GTC GTC GAG CGG CTC TCG 3844
1256 S   A   D   G   T   S   W   A   E   G   V   G   L   L   V   V   E   R   L   S  1275

3845 GAC GCC GAG CGC AAC GGC CAC CCC GTG CTC GCC GTG ATC CGG GGC AGC GCG GTC AAC CAG 3904
1276 D   A   E   R   N   G   H   P   V   L   A   V   I   R   G   S   A   V   N   Q  1295

3905 GAC GGC GCC TCC AAC GGG CTC ACC GCC CCC AAC GGC CCG TCC CAG CAG CGC GTC ATC CGA 3964
1296 D   G   A   S   N   G   L   T   A   P   N   G   P   S   Q   Q   R   V   I   R  1315

3965 CAG GCC CTG GCC GAC GCC GGG CTC ACC CCG GCC GAC GTC GAC GCC GTC GAG GCG CAC GGT 4024
1316 Q   A   L   A   D   A   G   L   T   P   A   D   V   D   A   V   E   A   H   G  1335

4025 ACG GGT ACC CGG CTC GGC GAC CCC ATC GAG GCC GAG GCG ATC CTC GGC ACC TAC GGC CGG 4084
1336 T   G   T   R   L   G   D   P   I   E   A   E   A   I   L   G   T   Y   G   R  1355

4085 GAC CGG GGC GAG GGC GCT CCG CTC CAG CTC GGC TCG CTG AAG TCG AAC ATC GGC CAC GCG 4144
1356 D   R   G   E   G   A   P   L   Q   L   G   S   L   K   S   N   I   G   H   A  1375

4145 CAG GCC GCC GCG GGC GTG GGC GGG CTC ATC AAG ATG GTC CTC GCG ATG CGC CAC GGC GTC 4204
1376 Q   A   A   A   G   V   G   G   L   I   K   M   V   L   A   M   R   H   G   V  1395

4205 CTG CCC AGG ACG CTC CAC GTG GAC CGG CCC ACC ACC CGC GTC GAC TGG GAG GCC GGC GGC 4264
1396 L   P   R   T   L   H   V   D   R   P   T   T   R   V   D   W   E   A   G   G  1415

4265 GTC GAG CTC CTC ACC GAG GAG CGG GAG TGG CCG GAG ACG GGC CGC CCG CGC CGC GCG GCG 4324
1416 V   E   L   L   T   E   E   R   E   W   P   E   T   G   R   P   R   R   A   A  1435

4325 ATC TCC TCC TTC GGC ATC AGC GGC ACC AAC GCC CAC ATC GTG GTC GAA CAG GCC CCG GAA 4384
1436 I   S   S   F   G   I   S   G   T   N   A   H   I   V   V   E   Q   A   P   E  1455

4385 GCC GGG GAG GCG GCG GTC ACC ACC ACC GCC CCG GAA GCA GGG GAA GCC GGG GAA GCG GCG 4444
1456 A   G   E   A   A   V   T   T   T   A   P   E   A   G   E   A   G   E   A   A  1475

4445 GAC ACC ACC GCC ACC ACG ACG CCG GCC GCG GTC GGC GTC CCC GAA CCC GTA CGC GCC CCC 4504
1476 D   T   T   A   T   T   T   P   A   A   V   G   V   P   E   P   V   R   A   P  1495

4505 GTC GTG GTC TCC GCG CGG GAC GCC GCC GCC CTG CGC GCC CAG GCC GTT CGG CTG CGG ACC 4564
1496 V   V   V   S   A   R   D   A   A   A   L   R   A   Q   A   V   R   L   R   T  1515
```

FIG. 23C

```
4565 TTC CTC GAC GGC CGA CCG GAC GTC ACC GTC GCC GAC CTC GGA CGC TCG CTG GCC GCC CGT 4624
1516  F   L   D   G   R   P   D   V   T   V   A   D   L   G   R   S   L   A   A   R  1535

4625 ACC GCC TTC GAG CAC AAG GCC GCC CTC ACC ACC GCC ACC AGG GAC GAG CTG CTC GCC GGG 4684
1536  T   A   F   E   H   K   A   A   L   T   T   A   T   R   D   E   L   L   A   G  1555

4685 CTC GAC GCC CTC GGC CGC GGG GAG CAA GCC ACG GGC CTG GTC ACC GGC GAA CCG GCC AGG 4744
1556  L   D   A   L   G   R   G   E   Q   A   T   G   L   V   T   G   E   P   A   R  1575

4745 GCC GGA CGC ACG GCC TTC CTG TTC ACC GGC CAG GGA GCG CAG CGC GTC GCC ATG GGC GAG 4804
1576  A   G   R   T   A   F   L   F   T   G   Q   G   A   Q   R   V   A   M   G   E  1595

4805 GAA CTG CGC GCC GCG CAC CCC GTG TTC GCC GCC GCC CTC GAC ACC GTG TAC GCG GCC CTC 4864
1596  E   L   R   A   A   H   P   V   F   A   A   A   L   D   T   V   Y   A   A   L  1615

4865 GAC CGT CAC CTC GAC CGG CCG CTG CGG GAG ATC GTC GCC GCC GGG GAG GAG CTG GAC CTC 4924
1616  D   R   H   L   D   R   P   L   R   E   I   V   A   A   G   E   E   L   D   L  1635

4925 ACC GCG TAC ACC CAG CCC GCC CTC TTC GCC TTC GAG GTG GCG CTG TTC CGC CTC CTC GAA 4984
1636  T   A   Y   T   Q   P   A   L   F   A   F   E   V   A   L   F   R   L   L   E  1655

4985 CAC CAC GGC CTC GTC CCC GAC CTG CTC ACC GGC CAC TCC GTC GGC GAG ATC GCC GCC GCG 5044
1656  H   H   G   L   V   P   D   L   L   T   G   H   S   V   G   E   I   A   A   A  1675

5045 CAC GTC GCC GGT GTC CTC TCC CTC GAC GAC GCC GCA CGT CTC GTC ACC GCC CGC GGC CGG 5104
1676  H   V   A   G   V   L   S   L   D   D   A   A   R   L   V   T   A   R   G   R  1695

5105 CTC ATG CAG TCG GCC CGC GAG GGC GGC GCG ATG ATC GCC GTG CAG GCG GGC GAG GCC GAG 5164
1696  L   M   Q   S   A   R   E   G   G   A   M   I   A   V   Q   A   G   E   A   E  1715

5165 GTC GTC GAG TCC CTG AAG GGC TAC GAG GGC AGG GTC GCC GTC GCC GCC GTC AAC GGA CCC 5224
1716  V   V   E   S   L   K   G   Y   E   G   R   V   A   V   A   A   V   N   G   P  1735

5225 ACC GCC GTG GTC GTC TCC GGC GAC GCG GAC GCC GCC GAG GAG ATC CGC GCC GTA TGG GCG 5284
1736  T   A   V   V   V   S   G   D   A   D   A   A   E   E   I   R   A   V   W   A  1755

5285 GGA CGC GGC CGG CGC ACC CGC AGG CTG CGC GTC AGC CAC GCC TTC CAC TCC CCG CAC ATG 5344
1756  G   R   G   R   R   T   R   R   L   R   V   S   H   A   F   H   S   P   H   M  1775

5345 GAC GAC GTC CTC GAC GAG TTC CTC CGG GTC GCC GAG GGC CTG ACC TTC GAG GAG CCG CGG 5404
1776  D   D   V   L   D   E   F   L   R   V   A   E   G   L   T   F   E   E   P   R  1795

5405 ATC CCC GTC GTC TCC ACG GTC ACC GGC GCG CTC GTC ACG TCC GGC GAG CTC ACC TCG CCC 5464
1796  I   P   V   V   S   T   V   T   G   A   L   V   T   S   G   E   L   T   S   P  1815

5465 GCG TAC TGG GTC GAC CAG ATC CGG CGG CCC GTG CGC TTC CTG GAC GCC GTC CGC ACC CTG 5524
1816  A   Y   W   V   D   Q   I   R   R   P   V   R   F   L   D   A   V   R   T   L  1835

5525 GCC GCC CAG GAC GCG ACC GTC CTC GTC GAG ATC GGC CCC GAC GCC GTC CTC ACG GCA CTC 5584
1836  A   A   Q   D   A   T   V   L   V   E   I   G   P   D   A   V   L   T   A   L  1855

5585 GCC GAG GAG GCT CTC GCG CCC GGC ACG GAC GCC CCG GAC GCC CGG GAC GTC ACG GTC GTC 5644
1856  A   E   E   A   L   A   P   G   T   D   A   P   D   A   R   D   V   T   V   V  1875

5645 CCG CTG CTG CGC GCG GGG CGC CCC GAG CCC GAG ACC CTC GCC GCC GGT CTC GCG ACC GCC 5704
1876  P   L   L   R   A   G   R   P   E   P   E   T   L   A   A   G   L   A   T   A  1895

5705 CAT GTC CAC GGC GCA CCC TTG GAC CGG GCG TCG TTC TTC CCG GAC GGG CGC CGC ACG GAC 5764
1896  H   V   H   G   A   P   L   D   R   A   S   F   F   P   D   G   R   R   T   D  1915

5765 CTG CCC ACG TAC GCC TTC CGG CGC GAG CAC TAC TGG CTG ACG CCC GAG GCC CGT ACG GAC 5824
1916  L   P   T   Y   A   F   R   R   E   H   Y   W   L   T   P   E   A   R   T   D  1935

5825 GCC CGC GCA CTC GGC TTC GAC CCG GCG CGG CAC CCG CTG CTG ACG ACC ACG GTC GAG GTC 5884
1936  A   R   A   L   G   F   D   P   A   R   H   P   L   L   T   T   T   V   E   V  1955

5885 GCC GGC GGC GAC GGC GTC CTG CTG ACC GGC CGT CTC TCC CTG ACC GAC CAG CCC TGG CTG 5944
1956  A   G   G   D   G   V   L   L   T   G   R   L   S   L   T   D   Q   P   W   L  1975

5945 GCC GAC CAC ATG GTC AAC GGC GCC GTC CTG TTG CCG GCC ACC GCC TTC CTG GAG CTC GCC 6004
1976  A   D   H   M   V   N   G   A   V   L   L   P   A   T   A   F   L   E   L   A  1995

6005 CTC GCG GCG GGC GAC CAC GTC GGG GCG GTC CGG GTG GAG GAA CTC ACC CTC GAA GCG CCG 6064
1996  L   A   A   G   D   H   V   G   A   V   R   V   E   E   L   T   L   E   A   P  2015

6065 CTC GTC CTG CCC GAG CGG GGC GCC GTC CGC ATC CAG GTC GGC GTG AGC GGC GAC GGC GAG 6124
2016  L   V   L   P   E   R   G   A   V   R   I   Q   V   G   V   S   G   D   G   E  2035
```

FIG. 23D

```
6125 TCG CCG GCC GGG CGC ACC TTC GGT GTG TAC AGC ACC CCC GAC TCC GGC GAC ACC GGT GAC 6184
2036  S   P   A   G   R   T   F   G   V   Y   S   T   P   D   S   G   D   T   G   D  2055

6185 GAC GCG CCC CGG GAG TGG ACC CGC CAT GTC TCC GGC GTA CTC GGC GAA GGG GAC CCG GCC 6244
2056  D   A   P   R   E   W   T   R   H   V   S   G   V   L   G   E   G   D   P   A  2075

6245 ACG GAG TCG GAC CAC CCC GGC ACC GAC GGG GAC GGT TCA GCG GCC TGG CCG CCT GCG GCG 6304
2076  T   E   S   D   H   P   G   T   D   G   D   G   S   A   A   W   P   P   A   A  2095

6305 GCG ACC GCC ACA CCC CTC GAC GGC GTC TAC GAC CGG CTC GCG GAG CTC GGC TAC GGA TAC 6364
2096  A   T   A   T   P   L   D   G   V   Y   D   R   L   A   E   L   G   Y   G   Y  2115

6365 GGT CCG GCC TTC CAG GGC CTG ACG GGC TGG CGC GAC GGC GCC GAC ACG CTC GCC GAG 6424
2116  G   P   A   F   Q   G   L   T   G   L   W   R   D   G   A   D   T   L   A   E  2135

6425 ATC CGG CTG CCC GCG GCG CAG CAC GAG AGC GCG GGG CTC TTC GGC GTA CAC CCG GCG CTG 6484
2136  I   R   L   P   A   A   Q   H   E   S   A   G   L   F   G   V   H   P   A   L  2155

6485 CTC GAC GCG GCG CTC CAC CCG ATC GTC CTG GAG GGC AAC TCA GCT GCC GGT GCC TGT GAC 6544
2156  L   D   A   A   L   H   P   I   V   L   E   G   N   S   A   A   G   A   C   D  2175

6545 GCC GAT ACC GAC GCG ACC GAC CGG ATC CGG CTG CCG TTC GCG TGG GCG GGG GTG ACC CTC 6604
2176  A   D   T   D   A   T   D   R   I   R   L   P   F   A   W   A   G   V   T   L  2195

6605 CAC GCC GAA GGG GCC ACC GCG CTC CGC GTA CGG ATC ACA CCC ACC GGC CCG GAC ACG GTC 6664
2196  H   A   E   G   A   T   A   L   R   V   R   I   T   P   T   G   P   D   T   V  2215

6665 ACG CTC CGC CTC ACC GAC ACC ACC GGT GCG CCC GTG GCC ACC GTG GAG TCC CTG ACC CTG 6724
2216  T   L   R   L   T   D   T   T   G   A   P   V   A   T   V   E   S   L   T   L  2235

6725 CGC GCG GTG GCG AAG GAC CGG CTG GGC ACC ACC GCC GGG CGC GTC GAC GAC GCC CTG TTC 6784
2236  R   A   V   A   K   D   R   L   G   T   T   A   G   R   V   D   D   A   L   F  2255

6785 ACG GTC GTG TGG ACG GAG ACC GGC ACA CCG GAA CCC GCA GGG CGC GGA GCC GTG GAG GTC 6844
2256  T   V   V   W   T   E   T   G   T   P   E   P   A   G   R   G   A   V   E   V  2275

6845 GAG GAA CTC GTC GAC CTC GCC GGC CTC GGC GAC CTC GTG GAG CTC GGC GCC GCG GAC GTC 6904
2276  E   E   L   V   D   L   A   G   L   G   D   L   V   E   L   G   A   A   D   V  2295

6905 GTC CTC CGG GCC GAC CGC TGG ACG CTC GAC GGG GAC CCG TCC GCC GCC GCG CGC ACA GCC 6964
2296  V   L   R   A   D   R   W   T   L   D   G   D   P   S   A   A   A   R   T   A  2315

6965 GTC CGG CGC ACC CTC GCC ATC GTC CAG GAG TTC CTG TCC GAG CCG CGC TTC GAC GGC TCG 7024
2316  V   R   R   T   L   A   I   V   Q   E   F   L   S   E   P   R   F   D   G   S  2335

7025 CGA CTG GTG TGC GTC ACC AGG GGC GCG GTC GCC GCA CTC CCC GGC GAG GAC GTC ACC TCC 7084
2336  R   L   V   C   V   T   R   G   A   V   A   A   L   P   G   E   D   V   T   S  2355

7085 CTC GCC ACC GGC CCC CTC TGG GGC CTC GTC CGC TCC GCC CAG TCC GAG AAC CCG GGA CGC 7144
2356  L   A   T   G   P   L   W   G   L   V   R   S   A   Q   S   E   N   P   G   R  2375

7145 CTG TTC CTC CTG GAC CTG GGT GAA GGC GAA GGC GAG CGC GAC GGA GCC GAG GAG CTG ATC 7204
2376  L   F   L   L   D   L   G   E   G   E   G   E   R   D   G   A   E   E   L   I  2395

7205 CGC GCG GCC ACG GCC GGG GAC GAG CCG CAG CTC GCG GCA CGG GAC GGC CGA CTG CTC GCG 7264
2396  R   A   A   T   A   G   D   E   P   Q   L   A   A   R   D   G   R   L   L   A  2415

7265 CCG AGG CTG GCC CGT ACC GCC GCC CTT TCG AGT GAG GAC ACC GCC GGC GGC GCC GAC CGT 7324
2416  P   R   L   A   R   T   A   A   L   S   S   E   D   T   A   G   G   A   D   R  2435

7325 TTC GGC CCC GAC GGC ACC GTC CTC GTC ACC GGG GGC ACC GGA GGC CTC GGA GCG CTC CTC 7384
2436  F   G   P   D   G   T   V   L   V   T   G   G   T   G   G   L   G   A   L   L  2455

7385 GCC CGC CAC CTC GTG GAG CGT CAC GGG GTG CGC CGG CTG CTG CTG GTG AGC CGC CGC GGG 7444
2456  A   R   H   L   V   E   R   H   G   V   R   R   L   L   L   V   S   R   R   G  2475

7445 GCC GAC GCC CCC GGC GCG GCC GAC CTG GGC GAG GAC CTC GCG GGC CTC GGC GCG GAG GTG 7504
2476  A   D   A   P   G   A   A   D   L   G   E   D   L   A   G   L   G   A   E   V  2495

7505 GCG TTC GCC GCC GCC GAC GCC GCC GAC CGC GAG AGC CTG GCG CGG GCG ATC GCC ACC GTG 7564
2496  A   F   A   A   A   D   A   A   D   R   E   S   L   A   R   A   I   A   T   V  2515

7565 CCC GCC GAG CAT CCG CTG ACG GCC GTC GTG CAC ACG GCG GGA GTC GTC GAC GAC GCG ACG 7624
2516  P   A   E   H   P   L   T   A   V   V   H   T   A   G   V   V   D   D   A   T  2535

7625 GTG GAG GCG CTC ACA CCG GAA CGG CTG GAC GCG GTA CTG CGC CCG AAG GTC GAC GCC GCG 7684
2536  V   E   A   L   T   P   E   R   L   D   A   V   L   R   P   K   V   D   A   A  2555
```

FIG. 23E

```
7685 TGG AAC CTG CAC GAG CTC ACC AAG GAC CTG CGG CTC GAC GCC TTC GTC CTC TTC TCC TCC 7744
2556  W   N   L   H   E   L   T   K   D   L   R   L   D   A   F   V   L   F   S   S  2575

7745 GTC TCC GGC ATC GTC GGC ACC GCC GGC CAG GCC AAC TAC GCG GCG GCC AAC ACG GGC CTC 7804
2576  V   S   G   I   V   G   T   A   G   Q   A   N   Y   A   A   A   N   T   G   L  2595

7805 GAC GCC CTC GCC GCC CAC CGC GCC GCC ACG GGC CTG GCC GCC ACG TCG CTG GCC TGG GGC 7864
2596  D   A   L   A   A   H   R   A   A   T   G   L   A   A   T   S   L   A   W   G  2615

7865 CTC TGG GAC GGC ACG CAC GGC ATG GGC GGC ACG CTC GGC GCC GCC GAC CTC GCC CGC TGG 7924
2616  L   W   D   G   T   H   G   M   G   G   T   L   G   A   A   D   L   A   R   W  2635

7925 AGC CGG GCC GGA ATC ACC CCG CTC ACC CCG CTG CAG GGC CTC GCG CTC TTC GAC GCC GCG 7984
2636  S   R   A   G   I   T   P   L   T   P   L   Q   G   L   A   L   F   D   A   A  2655

7985 GTC GCC AGG GAC GAC GCC CTC CTC GTA CCC GCC GGG CTC CGT CCC ACC GCC CAC CGG GGC 8044
2656  V   A   R   D   D   A   L   L   V   P   A   G   L   R   P   T   A   H   R   G  2675

8045 ACG GAC GGA CAG CCT CCT GCG CTG TGG CGC GGC CTC GTC CGG GCG CGC CCG CGC CGT GCC 8104
2676  T   D   G   Q   P   P   A   L   W   R   G   L   V   R   A   R   P   R   R   A  2695

8105 GCG CGG ACG GCC GCC GAG GCG GCG GAC ACG ACC GGC GGC TGG CTG AGC GGG CTC GCC GCA 8164
2696  A   R   T   A   A   E   A   A   D   T   T   G   G   W   L   S   G   L   A   A  2715

8165 CAG TCC CCC GAG GAG CGG CGC AGC ACA GCC GTC ACG CTC GTG ACG GGT GTC GTC GCG GAC 8224
2716  Q   S   P   E   E   R   R   S   T   A   V   T   L   V   T   G   V   V   A   D  2735

8225 GTC CTC GGG CAC GCC GAC TCC GCC GCG GTC GGG GCG GAG CGG TCC TTC AAG GAC CTC GGC 8284
2736  V   L   G   H   A   D   S   A   A   V   G   A   E   R   S   F   K   D   L   G  2755

8285 TTC GAC TCC CTG GCC GGG GTG GAG CTC CGC AAC CGG CTG AAC GCC GCC ACC GGC CTG CGG 8344
2756  F   D   S   L   A   G   V   E   L   R   N   R   L   N   A   A   T   G   L   R  2775

8345 CTC CCC GCG ACC ACG GTC TTC GAC CAT CCC TCG CCG GCC GCG CTC GCG TCC CAT CTC CTC 8404
2776  L   P   A   T   T   V   F   D   H   P   S   P   A   A   L   A   S   H   L   L  2795

8405 GCC CAG GTG CCC GGG TTG AAG GAG GGG ACG GCG GCG ACC GCG ACC GTC GTG GCC GAG CGG 8464
2796  A   Q   V   P   G   L   K   E   G   T   A   A   T   A   T   V   V   A   E   R  2815

8465 GGC GCT TCC TTC GGT GAC CGT GCG ACC GAC GAC GAT CCG ATC GCG ATC GTG GGC ATG GCA 8524
2816  G   A   S   F   G   D   R   A   T   D   D   D   P   I   A   I   V   G   M   A  2835

8525 TGC CGC TAT CCG GGT GGT GTG TCG TCG CCG GAG GAC CTG TGG CGG CTG GTG GCC GAG GGG 8584
2836  C   R   Y   P   G   G   V   S   S   P   E   D   L   W   R   L   V   A   E   G  2855

8585 ACG GAC GCG ATC AGC GAG TTC CCC GTC AAC CGC GGC TGG GAC CTG GAG AGC CTC TAC GAC 8644
2856  T   D   A   I   S   E   F   P   V   N   R   G   W   D   L   E   S   L   Y   D  2875

8645 CCG GAT CCC GAG TCG AAG GGC ACC ACG TAC TGC CGG GAG GGC GGG TTC CTG GAA GGC GCC 8704
2876  P   D   P   E   S   K   G   T   T   Y   C   R   E   G   G   F   L   E   G   A  2895

8705 GGT GAC TTC GAC GCC GCC TTC TTC GGC ATC TCG CCG CGC GAG GCC CTG GTG ATG GAC CCG 8764
2896  G   D   F   D   A   A   F   F   G   I   S   P   R   E   A   L   V   M   D   P  2915

8765 CAG CAG CGG CTG CTG CTG GAG GTG TCC TGG GAG GCG CTG GAA CGC GCG GGC ATC GAC CCG 8824
2916  Q   Q   R   L   L   L   E   V   S   W   E   A   L   E   R   A   G   I   D   P  2935

8825 TCC TCG CTG CGC GGC AGC CGC GGT GGT GTC TAC GTG GGC GCC GCG CAC GGC TCG TAC GCC 8884
2936  S   S   L   R   G   S   R   G   G   V   Y   V   G   A   A   H   G   S   Y   A  2955

8885 TCC GAT CCC CGG CTG GTG CCC GAG GGC TCG GAG GGC TAT CTG CTG ACC GGC AGC GCC GAC 8944
2956  S   D   P   R   L   V   P   E   G   S   E   G   Y   L   L   T   G   S   A   D  2975

8945 GCG GTG ATG TCC GGC CGC ATC TCC TAC GCG CTC GGT CTC GAA GGA CCG TCC ATG ACG GTG 9004
2976  A   V   M   S   G   R   I   S   Y   A   L   G   L   E   G   P   S   M   T   V  2995

9005 GAG ACG GCC TGC TCC TCC TCG CTG GTG GCG CTG CAT CTG GCG GTA CGG GCG CTG CGG CAC 9064
2996  E   T   A   C   S   S   S   L   V   A   L   H   L   A   V   R   A   L   R   H  3015

9065 GGC GAG TGC GGG CTC GCG CTG GCG GGC GGG GTG GCG GTG ATG GCC GAT CCG GCG GCG TTC 9124
3016  G   E   C   G   L   A   L   A   G   G   V   A   V   M   A   D   P   A   A   F  3035

9125 GTG GAG TTC TCC CGG CAG AAG GGG CTG GCC GCC GAC GGC CGC TGC AAG GCG TTC TCG GCC 9184
3036  V   E   F   S   R   Q   K   G   L   A   A   D   G   R   C   K   A   F   S   A  3055

9185 GCC GCC GAC GGC ACC GGC TGG GCC GAG GGC GTC GGC GTG CTC GTC CTG GAG CGG CTG TCG 9244
3056  A   A   D   G   T   G   W   A   E   G   V   G   V   L   V   L   E   R   L   S  3075
```

FIG. 23F

```
9245 GAC GCG CGC CGC GCG GGG CAC ACG GTC CTC GGC CTG GTC ACC GGC ACC GCG GTC AAC CAG 9304
3076 D   A   R   R   A   G   H   T   V   L   G   L   V   T   G   T   A   V   N   Q   3095

9305 GAC GGT GCC TCC AAC GGG CTG ACC GCG CCC AAC GGC CCA GCC CAG CAA CGC GTC ATC GCC 9364
3096 D   G   A   S   N   G   L   T   A   P   N   G   P   A   Q   Q   R   V   I   A   3115

9365 GAG GCG CTC GCC GAC GCC GGG CTG TCC CCG GAG GAC GTG GAC GCG GTC GAG GCG CAC GGC 9424
3116 E   A   L   A   D   A   G   L   S   P   E   D   V   D   A   V   E   A   H   G   3135

9425 ACC GGC ACC CGG CTC GGC GAC CCC ATC GAG GCC GGG GCG CTG CTC GCC GCC TCC GGA CGG 9484
3136 T   G   T   R   L   G   D   P   I   E   A   G   A   L   L   A   A   S   G   R   3155

9485 AAC CGT TCC GGC GAC CAC CCG CTG TGG CTC GGC TCG CTG AAG TCC AAC ATC GGG CAT GCC 9544
3156 N   R   S   G   D   H   P   L   W   L   G   S   L   K   S   N   I   G   H   A   3175

9545 CAG GCC GCC GCC GGT GTC GGC GGC GTC ATC AAG ATG CTC CAG GCG CTG CGG CAC GGC TTG 9604
3176 Q   A   A   A   G   V   G   G   V   I   K   M   L   Q   A   L   R   H   G   L   3195

9605 CTG CCC CGC ACC CTC CAC GCC GAC GAG CCG ACC CCG CAT GCC GAC TGG AGC TCC GGC CGG 9664
3196 L   P   R   T   L   H   A   D   E   P   T   P   H   A   D   W   S   S   G   R   3215

9665 GTA CGG CTG CTC ACC TCC GAG GTG CCG TGG CAG CGG ACC GGC CGG CCC CGG CGG ACC GGG 9724
3216 V   R   L   L   T   S   E   V   P   W   Q   R   T   G   R   P   R   R   T   G   3235

9725 GTG TCC GCC TTC GGC GTC GGC GGC ACC AAT GCC CAT GTC GTC CTC GAA GAG GCA CCC GCC 9784
3236 V   S   A   F   G   V   G   G   T   N   A   H   V   V   L   E   E   A   P   A   3255

9785 CCG CCC GCG CCG GAA CCG GCC GGG GAG GCC CCC GGC GGC TCC CGC GCC GCA GAA GGG GCG 9844
3256 P   P   A   P   E   P   A   G   E   A   P   G   G   S   R   A   A   E   G   A   3275

9845 GAA GGG CCC CTG GCC TGG GTG GTC TCC GGA CGC GAC GAG CCG GCC CTG CGG TCC CAG GCC 9904
3276 E   G   P   L   A   W   V   V   S   G   R   D   E   P   A   L   R   S   Q   A   3295

9905 CGG CGG CTC CGC GAC CAC CTC TCC CGC ACC CCC GGG GCC CGC CCG CGT GAC ATC GCC TTC 9964
3296 R   R   L   R   D   H   L   S   R   T   P   G   A   R   P   R   D   I   A   F   3315

9965 TCC CTC GCC GCC ACG CGC GCA GCC TTT GAC CAC CGC GCC GTG CTG ATC GGC TCG GAC GGG 10024
3316 S   L   A   A   T   R   A   A   F   D   H   R   A   V   L   I   G   S   D   G   3335

10025 GCC GAA CTC GCC GCC GCC CTG GAC GCG TTG GCC GAA GGA CGC GAC GGT CCG GCG GTG GTG 10084
3336 A   E   L   A   A   A   L   D   A   L   A   E   G   R   D   G   P   A   V   V   3355

10085 CGC GGA GTC CGC GAC CGG GAC GGC AGG ATG GCC TTC CTC TTC ACC GGG CAG GGC AGC CAG 10144
3356 R   G   V   R   D   R   D   G   R   M   A   F   L   F   T   G   Q   G   S   Q   3375

10145 CGC GCC GGG ATG GCC CAC GAC CTG CAT GCC GCC CAT ACC TTC TTC GCG TCC GCC CTC GAC 10204
3376 R   A   G   M   A   H   D   L   H   A   A   H   T   F   F   A   S   A   L   D   3395

10205 GAG GTG ACG GAC CGT CTC GAC CCG CTG CTC GGC CGG CCG CTC GGC GCG CTG CTG GAC GCC 10264
3396 E   V   T   D   R   L   D   P   L   L   G   R   P   L   G   A   L   L   D   A   3415

10265 CGA CCC GGC TCG CCC GAA GCG GCA CTC CTG GAC CGG ACC GAG TAC ACC CAG CCG GCG CTC 10324
3416 R   P   G   S   P   E   A   A   L   D   R   T   E   Y   T   Q   P   A   L   3435

10325 TTC GCC GTC GAG GTG GCG CTC CAC CGG CTG CTG GAG CAC TGG GGG ATG CGC CCC GAC CTG 10384
3436 F   A   V   E   V   A   L   H   R   L   L   E   H   W   G   M   R   P   D   L   3455

10385 CTG CTG GGG CAC TCG GTG GGC GAA CTG GCG GCC GCC CAC GTC GCG GGT GTG CTC GAT CTC 10444
3456 L   L   G   H   S   V   G   E   L   A   A   A   H   V   A   G   V   L   D   L   3475

10445 CAC GAC GCC TGC GCG CTG GTG GCC GCC CGC GGC AGG CTG ATG CAG CGC CTG CCG CCC GGC 10504
3476 D   D   A   C   A   L   V   A   A   R   G   R   L   M   Q   R   L   P   P   G   3495

10505 GGC GCG ATG GTC TCC GTG CGG GCC GGC GAG GAC GAG GTC CGC GCA CTG CTG GCC GGC CGC 10564
3496 G   A   M   V   S   V   R   A   G   E   D   E   V   R   A   L   L   A   G   R   3515

10565 GAG GAC GCC GTC TGC GTC GCC GCG GTG AAC GGC CCC CGG TCG GTG GTG ATC TCC GGC GCG 10624
3516 E   D   A   V   C   V   A   A   V   N   G   P   R   S   V   V   I   S   G   A   3535

10625 GAG GAA GCG GTG GCC GAG GCG GCG GCG CAG CTC GCC GGA CGA GGC CGC CGC ACC AGG CGG 10684
3536 E   E   A   V   A   E   A   A   A   Q   L   A   G   R   R   R   T   R   R   3555

10685 CTC CGC GTC GCG CAC GCC TTC CAC TCA CCC CTG ATG GAC GGC ATG CTC GCC GGA TTC CGG 10744
3556 L   R   V   A   H   A   F   H   S   P   L   M   D   G   M   L   A   G   F   R   3575

10745 GAG GTC GCC GCC GGC CTG CGC TAC CGG GAA CCG GAG CTG ACG GTC GTC TCC ACG GTC ACG 10804
3576 E   V   A   A   G   L   R   Y   R   E   P   E   L   T   V   V   S   T   V   T   3595
```

FIG. 23G

```
10805 GGG CGG CCC GCC CGC CCC GGT GAA CTC ACC GGC CCC GAC TAC TGG GTG GCC CAG GTC CGT 10864
3596  G   R   P   A   R   P   G   E   L   T   G   P   D   Y   W   V   A   Q   V   R   3615

10865 GAG CCC GTG CGC TTC GCG GAC GCG GTC CGC ACG GCA CAC CGC CTC GGA GCC CGC ACC TTC 10924
3616  E   P   V   R   F   A   D   A   V   R   T   A   H   R   L   G   A   R   T   F   3635

10925 CTG GAG ACC GGC CCG GAC GGC GTG CTG TGC GGC ATG GCA GAG GAG TGC CTG GAG GAC GAC 10984
3636  L   E   T   G   P   D   G   V   L   C   G   M   A   E   E   C   L   E   D   D   3655

10985 ACC GTG GCC CTG CTG CCG GCG ATC CAC AAG CCC GGC ACC GCG CCG CAC GGT CCG GCG GCT 11044
3656  T   V   A   L   L   P   A   I   H   K   P   G   T   A   P   H   G   P   A   A   3675

11045 CCC GGC GCG CTG CGG GCG GCC GCC GCC GCG TAC GGC CGG GGC GCC CGG GTG GAC TGG GCC 11104
3676  P   G   A   L   R   A   A   A   A   A   Y   G   R   G   A   R   V   D   W   A   3695

11105 GGG ATG CAC GCC GAC GGC CCC GAG GGG CCG GCC CGC CGC GTC GAA CTG CCC GTC CAC GCC 11164
3696  G   M   H   A   D   G   P   E   G   P   A   R   R   V   E   L   P   V   H   A   3715

11165 TTC CGG CAC CGC CGC TAC TGG CTC GCC CCG GGC CGC GCG GCG GAC ACC GAC GAC TGG ATG 11224
3716  F   R   H   R   R   Y   W   L   A   P   G   R   A   A   D   T   D   D   W   M   3735

11225 TAC CGG ATC GGC TGG GAC CGG CTG CCG GCT GTG ACC GGC GGG GCC CGG ACC GCC GGC CGC 11284
3736  Y   R   I   G   W   D   R   L   P   A   V   T   G   G   A   R   T   A   G   R   3755

11285 TGG CTG GTG ATC CAC CCC GAC AGC CCG CGC TGC CGG GAG CTG TCC GGC CAC GCC GAA CGC 11344
3756  W   L   V   I   H   P   D   S   P   R   C   R   E   L   S   G   H   A   E   R   3775

11345 GCG CTG CGC GCC GCG GGC GCG AGC CCC GTA CCG CTG CCC GTG GAC GCT CCG GCC GCC GAC 11404
3776  A   L   R   A   A   G   A   S   P   V   P   L   P   V   D   A   P   A   A   D   3795

11405 CGG GCG TCC TTC GCG GCA CTG CTG CGC TCC GCC ACC GGA CCT GAC ACA CGA GGT GAC ACA 11464
3796  R   A   S   F   A   A   L   L   R   S   A   T   G   P   D   T   R   G   D   T   3815

11465 GCC GCG CCC GTG GCC GGT GTG CTG TCG CTG CTG TCC GAG GAG GAT CGG CCC CAT CGC CAG 11524
3816  A   A   P   V   A   G   V   L   S   L   L   S   E   E   D   R   P   H   R   Q   3835

11525 CAC GCC CCG GTA CCC GCC GGG GTC CTG GCG ACG CTG TCC CTG ATG CAG GCT ATG GAG GAG 11584
3836  H   A   P   V   P   A   G   V   L   A   T   L   S   L   M   Q   A   M   E   E   3855

11585 GAG GCG GTG GAG GCT CGC GTG TGG TGC GTC TCC CGC GCC GCG GTC GCC GCC GCC GAC CGG 11644
3856  E   A   V   E   A   R   V   W   C   V   S   R   A   A   V   A   A   A   D   R   3875

11645 GAA CGG CCC GTC GGC GCG GGC GCC GCC CTG TGG GGG CTG GGC CGG GTG GCC GCC CTG GAA 11704
3876  E   R   P   V   G   A   G   A   A   L   W   G   L   G   R   V   A   A   L   E   3895

11705 CGC CCC ACC CGG TGG GGC GGT CTC GTG GAC CTG CCC GCC TCG CCC GGT GCG GCG CAC TGG 11764
3896  R   P   T   R   W   G   G   L   V   D   L   P   A   S   P   G   A   A   H   W   3915

11765 GCG GCC GCC GTG GAA CGG CTC GCC GGT CCC GAG GAC CAG ATC GCC GTG CGC GCG TCC GGC 11824
3916  A   A   A   V   E   R   L   A   G   P   E   D   Q   I   A   V   R   A   S   G   3935

11825 AGT TGG GGC CGG CGC CTC ACC AGG CTG CCG CGC GAC GGC GGC GGC CGG ACG GCC GCA CCC 11884
3936  S   W   G   R   R   L   T   R   L   P   R   D   G   G   G   R   T   A   A   P   3955

11885 GCG TAC CGG CCG CGC GGC ACG GTG CTC GTC ACC GGT GGC ACC GGC GCG CTC GGC GGG CAT 11944
3956  A   Y   R   P   R   G   T   V   L   V   T   G   G   T   G   A   L   G   G   H   3975

11945 CTC GCC CGC TGG CTC GCC GCG GCG GGC GCC GAA CAC CTG GCG CTC ACC AGC CGC CGG GGC 12004
3976  L   A   R   W   L   A   A   A   G   A   E   H   L   A   L   T   S   R   R   G   3995

12005 CCG GAC GCG CCC GGC GCC GCC GGA CTC GAG GCC GAA CTC CTC CTC CTG GCC GCC AAG GTG 12064
3996  P   D   A   P   G   A   A   G   L   E   A   E   L   L   L   L   G   A   K   V   4015

12065 ACG TTC GCC GCC TGC GAC ACC GCC GAC CGC GAC GGC CTC GCC CGG GTC CTG CGG GCG ATA 12124
4016  T   F   A   A   C   D   T   A   D   R   D   G   L   A   R   V   L   R   A   I   4035

12125 CCG GAG GAC ACC CCG CTC ACC GCG GTG TTC CAC GCC GCG GGC GTA CCG CAG GTC ACG CCG 12184
4036  P   E   D   T   P   L   T   A   V   F   H   A   A   G   V   P   Q   V   T   P   4055

12185 CTG TCC CGT ACC TCG CCC GAG CAC TTC GCC GAC GTG TAC GCG GGC AAG GCG GCG GGC GCC 12244
4056  L   S   R   T   S   P   E   H   F   A   D   V   Y   A   G   K   A   A   G   A   4075

12245 GCG CAC CTG GAC GAA CTG ACC CGC GAA CTC GGC GCC GGA CTC GAC GCG TTC GTC CTC TAC 12304
4076  A   H   L   D   E   L   T   R   E   L   G   A   G   L   D   A   F   V   L   Y   4095

12305 TCC TCC GGC GCC GGC GTC TGG GGC AGC GCC GGC CAG GGT GCC TAC GCC GCC GCC AAC GCC 12364
4096  S   S   G   A   G   V   W   G   S   A   G   Q   G   A   Y   A   A   A   N   A   4115
```

FIG. 23H

```
12365 GCC CTG GAC GCG CTC GCC CGG CGC CGT GCG GCG GAC GGA CTC CCC GCC ACC TCC ATC GCC 12424
4116  A   L   D   A   L   A   R   R   R   A   A   D   G   L   P   A   T   S   I   A  4135

12425 TGG GGC GTG TGG GGC GGC GGC GGT ATG GGG GCC GAC GAG GCG GGC GCG GAG TAT CTG GGC 12484
4136  W   G   V   W   G   G   G   G   M   G   A   D   E   A   G   A   E   Y   L   G  4155

12485 CGG CGC GGT ATG CGC CCC ATG GCA CCG GTC TCC GCG CTC CGG GCG ATG GCC ACC GCC ATC 12544
4156  R   R   G   M   R   P   M   A   P   V   S   A   L   R   A   M   A   T   A   I  4175

12545 GCC TCC GGG GAA CCC TGC CCC ACC GTC ACC CAC ACC GAC TGG GAG CGC TTC GGC GAG GGC 12604
4176  A   S   G   E   P   C   P   T   V   T   H   T   D   W   E   R   F   G   E   G  4195

12605 TTC ACC GCC TTC CGG CCC AGC CCT CTG ATC GCG GGC CTC GGC ACG CCG GGC GGC GGC CGG 12664
4196  F   T   A   F   R   P   S   P   L   I   A   G   L   G   T   P   G   G   G   R  4215

12665 GCG GCG GAG ACC CCC GAG GAG GGG AAC GCC ACC GCT GCG GCG GAC CTC ACC GCC CTG CCG 12724
4216  A   A   E   T   P   E   E   G   N   A   T   A   A   A   D   L   T   A   L   P  4235

12725 CCC GCC GAA CTC CGC ACC GCG CTG CGC GAG CTG GTG CGA GCC CGG ACC GCC GCG GCG CTC 12784
4236  P   A   E   L   R   T   A   L   R   E   L   V   R   A   R   T   A   A   A   L  4255

12785 GGC CTC GAC GAC CCG GCC GAG GTC GCC GAG GGC GAA CGG TTC CCC GCC ATG GGC TTC GAC 12844
4256  G   L   D   D   P   A   E   V   A   E   G   E   R   F   P   A   M   G   F   D  4275

12845 TCC CTG GCC ACC GTA CGG CTG CGC CGC GGA CTC GCC TCG GCC ACG GGC CTC GAC CTG CCC 12904
4276  S   L   A   T   V   R   L   R   R   G   L   A   S   A   T   G   L   D   L   P  4295

12905 CCC GAT CTG CTC TTC GAC CGG GAC ACC CCG GCC GCG CTC GCC GCC CAC CTG GCC GAA CTG 12964
4296  P   D   L   L   F   D   R   D   T   P   A   A   L   A   A   H   L   A   E   L  4315

12965 CTC GCC ACC GCA CGG GAC CAC GGA CCC GGC GGC CCC GGG ACC GGT GCC GCG CCG GCC GAT 13024
4316  L   A   T   A   R   D   H   G   P   G   G   P   G   T   A   A   P   A   D  4335

13025 GCC GGA AGC GGC CTG CCG GCC CTC TAC CGG GAG GCC GTC CGC ACC GGC CGG GCC GCG GAA 13084
4336  A   G   S   G   L   P   A   L   Y   R   E   A   V   R   T   G   R   A   A   E  4355

13085 ATG GCC GAA CTG CTC GCC GCC GCT TCC CGG TTC CGC CCC GCC TTC GGG ACG GCG GAC CGG 13144
4356  M   A   E   L   L   A   A   A   S   R   F   R   P   A   F   G   T   A   D   R  4375

13145 CAG CCG GTG GCC CTC GTG CCG CTG GCC GAC GGC GCG GAG GAC ACC GGG CTC CCG CTG CTC 13204
4376  Q   P   V   A   L   V   P   L   A   D   G   A   E   D   T   G   L   P   L   L  4395

13205 GTG GGC TGC GCC GGG ACG GCG GTG GCC TCC GGC CCG GTG GAG TTC ACC GCC TTC GCC GGA 13264
4396  V   G   C   A   G   T   A   V   A   S   G   P   V   E   F   T   A   F   A   G  4415

13265 GCG CTG GCG GAC CTC CCG GCG GCG GCC CCG ATG GCC GCG CTG CCG CAG CCC GGC TTT CTG 13324
4416  A   L   A   D   L   P   A   A   A   P   M   A   A   L   P   Q   P   G   F   L  4435

13325 CCG GGA GAA CGA GTC CCG GCC ACC CCG GAG GCA TTG TTC GAG GCC CAG GCG GAA GCG CTG 13384
4436  P   G   E   R   V   P   A   T   P   E   A   L   F   E   A   Q   A   E   A   L  4455

13385 CTG CGC TAC GCG GCC GGC CGG CCC TTC GTG CTG CTG GGG CAC TCC GCC GGC GCC AAC ATG 13444
4456  L   R   Y   A   A   G   R   P   F   V   L   L   G   H   S   A   G   A   N   M  4475

13445 GCC CAC GCC CTG ACC CGT CAT CTG GAG GCG AAC GGT GGC GGC CCC GCA GGG CTG GTG CTC 13504
4476  A   H   A   L   T   R   H   L   E   A   N   G   G   P   A   G   L   V   L  4495

13505 ATG GAC ATC TAC ACC CCC GCC GAC CCC GGC GCG ATG GGC GTC TGG CGG AAC GAC ATG TTC 13564
4496  M   D   I   Y   T   P   A   D   P   G   A   M   G   V   W   R   N   D   M   F  4515

13565 CAG TGC GTC TGG CGG CGC TCG GAC ATC CCC CCG GAC GAC CAC CGC CTC ACG GCC ATG GGC 13624
4516  Q   W   V   W   R   R   S   D   I   P   P   D   D   H   R   L   T   A   M   G  4535

13625 GCC TAC CAC CGG CTG CTT CTC GAC TGG TCG CCC ACC CCC GTC CGC GCC CCC GTA CTG CAT 13684
4536  A   Y   H   R   L   L   L   D   W   S   P   T   P   V   R   A   P   V   L   H  4555

13685 CTG CGC GCC GCG GAA CCC ATG GGC GAC TGG CCA CCC GGG GAC ACC GGC TGG CAG TCC CAC 13744
4556  L   R   A   A   E   P   M   G   D   W   P   P   G   D   T   G   W   Q   S   H  4575

13745 TGG GAC GGC GCG CAC ACC ACC GCC GGC ATC CCC GGA AAC CAC TTC ACG ATG ATG ACC GAA 13804
4576  W   D   G   A   H   T   T   A   G   I   P   G   N   H   F   T   M   M   T   E  4595

13805 CAC GCC TCC GCC GCC GCC CGG CTC GTG CAC GGC TGG CTC GCG GAA CGG ACC CCG TCC GGG 13864
4596  H   A   S   A   A   A   R   L   V   H   G   W   L   A   E   R   T   P   S   G  4615

13865 CAG GGC GGG TCA CCG TCC CGC GCG GCG GGG AGA GAG GAG AGG CCG TGA ACACGGCAGCCGGCCC 13928
4616  Q   G   G   S   P   S   R   A   A   G   R   E   E   R   P   *                    4631
```

FIG. 231

```
13929 GACCGGCACCGCCGCCGGCGGCACCACCGCCCCGGCGGCGGCACACGACCTGTCCCGCGCCGGACGCAGGCTCCAACTCA 14008

14009 CCCGGGCCGCACAGTGGTTCGCCGGCAACCAGGGAGACCCCTACGGG ATG ATC CTG CGC GCC GGC ACC GCC 14079
     1                                                   M   I   L   R   A   G   T   A   8

14080 GAC CCG GCA CCG TAC GAG GAA GAG ATC CCC GGG TAC CGA GCT CGA ATT CTT AAT TAA GGAG 14140
    9 D   P   A   P   Y   E   E   E   I   P   G   Y   R   A   R   I   L   N   *     27

14141 GTCGTAG ATG AGT AAC AAG AAC AAC GAT GAG CTG CAG CGG CAG GCC TCG GAA AAC ACC CTG 14201
    1       M   S   N   K   N   N   D   E   L   Q   R   Q   A   S   E   N   T   L   18

14202 GGG CTG AAC CCG GTC ATC GGT ATC CGC CGC AAA GAC CTG TTG AGC TCG GCA CGC ACC GTG 14261
   19 G   L   N   P   V   I   G   I   R   R   K   D   L   L   S   S   A   R   T   V   38

14262 CTG CGC CAG GCC GTG CGC CAA CCG CTG CAC AGC GCC AAG CAT GTG GCC CAC TTT GGC CTG 14321
   39 L   R   Q   A   V   R   Q   P   L   H   S   A   K   H   V   A   H   F   G   L   58

14322 GAG CTG AAG AAC GTG CTG CTG GGC AAG TCC AGC CTT GCC CCG GAA AGC GAC GAC CGT CGC 14381
   59 E   L   K   N   V   L   L   G   K   S   S   L   A   P   E   S   D   D   R   R   78

14382 TTC AAT GAC CCG GCA TGG AGC AAC AAC CCA CTT TAC CGC CGC TAC CTG CAA ACC TAT CTG 14441
   79 F   N   D   P   A   W   S   N   N   P   L   Y   R   R   Y   L   Q   T   Y   L   98

14442 GCC TGG CGC AAG GAG CTG CAG GAC TGG ATC GGC AAC AGC GAC CTG TCG CCC CAG GAC ATC 14501
   99 A   W   R   K   E   L   Q   D   W   I   G   N   S   D   L   S   P   Q   D   I   118

14502 AGC CGC GGC CAG TTC GTC ATC AAC CTG ATG ACC GAA GCC ATG GCT CCG ACC AAC ACC CTG 14561
  119 S   R   G   Q   F   V   I   N   L   M   T   E   A   M   A   P   T   N   T   L   138

14562 TCC AAC CCG GCA GCA GTC AAA CGC TTC TTC GAA ACC GGC GGC AAG AGC CTG CTC GAT GGC 14621
  139 S   N   P   A   A   V   K   R   F   F   E   T   G   G   K   S   L   L   D   G   158

14622 CTG TCC AAC CTG GCC AAG GAC CTG GTC AAC AAC GGT GGC ATG CCC AGC CAG GTG AAC ATG 14681
  159 L   S   N   L   A   K   D   L   V   N   N   G   G   M   P   S   Q   V   N   M   178

14682 GAC GCC TTC GAG GTG GGC AAG AAC CTG GGC ACC AGT GAA GGC GCC GTG GTG TAC CGC AAC 14741
  179 D   A   F   E   V   G   K   N   L   G   T   S   E   G   A   V   V   Y   R   N   198

14742 GAT GTG CTG GAG CTG ATC CAG TAC AAG CCC ATC ACC GAG CAG GTG CAT GCC CGC CCG CTG 14801
  199 D   V   L   E   L   I   Q   Y   K   P   I   T   E   Q   V   H   A   R   P   L   218

14802 CTG GTG GTG CCG CCG CAG ATC AAC AAG TTC TAC GTA TTC GAC CTG AGC CCG GAA AAG AGC 14861
  219 L   V   V   P   P   Q   I   N   K   F   Y   V   F   D   L   S   P   E   K   S   238

14862 CTG GCA CGC TAC TGC CTG CGC TCG CAG CAG CAG ACC TTC ATC ATC AGC TGG CGC AAC CCG 14921
  239 L   A   R   Y   C   L   R   S   Q   Q   Q   T   F   I   I   S   W   R   N   P   258

14922 ACC AAA GCC CAG CGC GAA TGG GGC CTG TCC ACC TAC ATC GAC GCG CTC AAG GAG GCG GTC 14981
  259 T   K   A   Q   R   E   W   G   L   S   T   Y   I   D   A   L   K   E   A   V   278

14982 GAC GCG GTG CTG GCG ATT ACC GGC AGC AAG GAC CTG AAC ATG CTC GGT GCC TGC TCC GGC 15041
  279 D   A   V   L   A   I   T   G   S   K   D   L   N   M   L   G   A   C   S   G   298

15042 GGC ATC ACC TGC ACG GCA TTG GTC GGC CAC TAT GCC GCC CTC GGC GAA AAC AAG GTC AAT 15101
  299 G   I   T   C   T   A   L   V   G   H   Y   A   A   L   G   E   N   K   V   N   318

15102 GCC CTG ACC CTG CTG GTC AGC GTG CTG GAC ACC ACC ATG GAC AAC CAG GTC GCC CTG TTC 15161
  319 A   L   T   L   L   V   S   V   L   D   T   T   M   D   N   Q   V   A   L   F   338

15162 GTC GAC GAG CAG ACT TTG GAG GCC GCC AAG CGC CAC TCC TAC CAG GCC GGT GTG CTC GAA 15221
  339 V   D   E   Q   T   L   E   A   A   K   R   H   S   Y   Q   A   G   V   L   E   358

15222 GGC AGC GAG ATG GCC AAG GTG TTC GCC TGG ATG CGC CCC AAC GAC CTG ATC TGG AAC TAC 15281
  359 G   S   E   M   A   K   V   F   A   W   M   R   P   N   D   L   I   W   N   Y   378

15282 TGG GTC AAC AAC TAC CTG CTC GGC AAC GAG CCG CCG GTG TTC GAC ATC CTG TTC TGG AAC 15341
  379 W   V   N   N   Y   L   L   G   N   E   P   P   V   F   D   I   L   F   W   N   398

15342 AAC GAC ACC ACG CGC CTG CCG GCC GCC TTC CAC GGC GAC CTG ATC GAA ATG TTC AAG AGC 15401
  399 N   D   T   T   R   L   P   A   A   F   H   G   D   L   I   E   M   F   K   S   418

15402 AAC CCG CTG ACC CGC CCG GAC GCC CTG GAG GTT TGC GGC ACT CCG ATC GAC CTG AAA CAG 15461
  419 N   P   L   T   R   P   D   A   L   E   V   C   G   T   P   I   D   L   K   Q   438

15462 GTC AAA TGC GAC ATC TAC AGC CTT GCC GGC ACC AAC GAC CAC ATC ACC CCG TGG CAG TCA 15521
  439 V   K   C   D   I   Y   S   L   A   G   T   N   D   H   I   T   P   W   Q   S   458
```

FIG. 23J

```
15522 TGC TAC CGC TCG GCG CAC CTG TTC GGC GGC AAG ATC GAG TTC GTG CTG TCC AAC AGC GGC 15581
 459  C   Y   R   S   A   H   L   F   G   G   K   I   E   F   V   L   S   N   S   G   478

15582 CAC ATC CAG AGC ATC CTC AAC CCG CCA GGC AAC CCC AAG GCG CGC TTC ATG ACC GGT GCC 15641
 479  H   I   Q   S   I   L   N   P   P   G   N   P   K   A   R   F   M   T   G   A   498

15642 GAT CGC CCG GGT GAC CCG GTG GCC TGG CAG GAA AAC GCC ACC AAG CAT GCC GAC TCC TGG 15701
 499  D   R   P   G   D   P   V   A   W   Q   E   N   A   T   K   H   A   D   S   W   518

15702 TGG CTG CAC TGG CAA AGC TGG CTG GGC GAG CGT GCC GGC GAG CTG GAA AAG GCG CCG ACC 15761
 519  W   L   H   W   Q   S   W   L   G   E   R   A   G   E   L   E   K   A   P   T   538

15762 CGC CTG GGC AAC CGT GCC TAT GCC GCT GGC GAG GCA TCC CCG GGC ACC TAC GTT CAC GAG 15821
 539  R   L   G   N   R   A   Y   A   A   G   E   A   S   P   G   T   Y   V   H   E   558

15822 CGT TGA GCTGCAGCGCCGTGGCCACCTGCGGGACGCCACGGTGTTGAATTC                            15872
 559  R   *                                                                          560
```

FIG. 23K

METABOLIC ENGINEERING OF POLYHYDROXYALKANOATE MONOMER SYNTHASES

This application is a 371 of PCT/US96/20119 filed Dec. 18, 1996 and claims the benefits of Provisional Application No. 60/008,847 filed Dec. 19, 1995.

BACKGROUND OF THE INVENTION

Polyhydroxyalkanoates (PHAs) are one class of biodegradable polymers. The first identified member of the PHAs thermoplastics was polyhydroxybutyrate (PHB), the polymeric ester of D(-)-3-hydroxybutyrate.

The biosynthetic pathway of PHB in the gram negative bacterium *Alcaligenes eutrophus* is depicted in FIG. 1. PHAs related to PHB differ in the structure of the pendant arm, R (FIG. 2). For example, $R=CH_3$ in PHB, while $R=CH_2CH_3$ in polyhydroxyvalerate, and $R=(CH_2)_4CH_3$ in polyhydroxyoctanoate.

The genes responsible for PHB synthesis in *A. eutrophus* have been cloned and sequenced. (Peoples et al., *J. Biol. Chem.*, 264, 15293 (1989); Peoples et al., *J. Biol. Chem.* 264, 15298 (1989)). Three enzymes: β-ketothiolase (phbA), acetoacetyl-CoA reductase (phbB), and PHB synthase (phbC) are involved in the conversion of acetyl-CoA to PHB. The PHB synthase gene encodes a protein of $M_r=63,900$ which is active when introduced into *E. coli* (Peoples et al., *J. Biol. Chem.*, 26, 15298 (1989)).

Although PHB represents the archetypical form of a biodegradable thermoplastic, its physical properties preclude significant use of the homopolymer form. Pure PHB is highly crystalline and, thus, very brittle. However, unique physical properties resulting from the structural characteristics of the R groups in a PHA copolymer may result in a polymer with more desirable characteristics. These characteristics include altered crystallinity, UV weathering resistance, glass to rubber transition temperature ($T_g$), melting temperature of the crystalline phase, rigidity and durability (Holmes et al., EPO 00052 459; Anderson et al., *Microbiol. Rev.*, 54, 450 (1990)). Thus, these polyesters behave as thermoplastics, with melting temperatures of 50–180° C., which can be processed by conventional extension and molding equipment.

Traditional strategies for producing random PHA copolymers involve feeding short and long chain fatty acid monomers to bacterial cultures. However, this technology is limited by the monomer units which can be incorporated into a polymer by the endogenous PHA synthase and the expense of manufacturing PHAs by existing fermentation methods (Haywood et al., *FEMS Microbiol. Lett.*, 57, 1 (1989); Poi et al., *Int. J. Biol. Macromol.*, 12, 106 (1990); Steinbuchel et al., In: *Novel Biomaterials from Biological Sources*. D. Byron (ed.), MacMillan, N.Y. (1991); Valentin et al., *Appl. Microbiol. Biotechnical*, 36, 507 (1992)).

The production of diverse hydroxyacylCoA monomers for homo- and co-polymeric PHAs also occurs in some bacteria through the reduction and condensation pathway of fatty acids. This pathway employs a fatty acid synthase (FAS) which condenses malonate and acetate. The resulting β-keto group undergoes three processing steps, β-keto reduction, dehydration, and enoyl reduction, to yield a fully saturated butyryl unit. However, this pathway provides only a limited array of PHA monomers which vary in alkyl chain length but not in the degree of alkyl group branching, saturation, or functionalization along the acyl chain.

The biosynthesis of polyketides, such as erythromycin, is mechanistically related to formation of long-chain fatty acids. However, polyketides, in contrast to FASs, retain ketone, hydroxyl, or olefinic functions and contain methyl or ethyl side groups interspersed along an acyl chain comparable in length to that of common fatty acids. This asymmetry in structure implies that the polyketide synthase (PKS), the enzyme system responsible for formation of these molecules, although mechanistically related to a FAS, results in an end product that is structurally very different than that of a long chain fatty acid.

Because PHAs are biodegradable polymers that have the versatility to replace petrochemical-based thermoplastics, it is desirable that new, more economic methods be provided for the production of defined PHAs. Thus, what is needed are methods to produce recombinant PHA monomer synthases for the generation of PHA polymers.

SUMMARY OF THE INVENTION

The present invention provides a method of preparing a polyhydroxyalkanoate synthase. The method comprises introducing an expression cassette into a non-plant eukaryotic cell. The expression cassette comprises a DNA molecule encoding a polyhydroxyalkanoate synthase operably linked to a promoter functional in the non-plant eukaryotic cell. The DNA molecule encoding the polyhydroxyalkanoate synthase is then expressed in the cell. Thus, another embodiment of the invention provides a purified, isolated recombinant polyhydroxybutyrate synthase.

Another embodiment of the invention is a method of preparing a polyhydroxyalkanoate polymer. The method comprises introducing a first expression cassette and a second expression cassette into a eukaryotic cell. The first expression cassette comprises a DNA segment encoding a fatty acid synthase in which the dehydrase activity has been inactivated that is operably linked to a promoter functional in the eukaryotic cell. The second expression cassette comprises a DNA segment encoding a polyhydroxyalkanoate synthase operably linked to a promoter functional in the eukaryotic cell. The DNA segments in the expression cassettes are expressed in the cell so as to yield a polyhydroxyalkanoate polymer.

Another embodiment of the invention is a baculovirus expression cassette comprising a nucleic acid molecule encoding a polyhydroxyalkanoate synthase operably linked to a promoter functional in an insect cell.

The present invention also provides an expression cassette comprising a nucleic acid molecule encoding a polyhydroxyalkanoate monomer synthase operably linked to a promoter functional in a host cell. The nucleic acid molecule comprises a plurality of DNA segments. Thus, the nucleic acid molecule comprises at least a first and a second DNA segment. No more than one DNA segment is derived from the eryA gene cluster of *Saccharopolyspora erythraea*. The first DNA segment encodes a first module and the second DNA segment encodes a second module, wherein the DNA segments together encode a polyhydroxyalkanoate synthase.

Also provided is an isolated and purified DNA molecule. The DNA molecule comprises a plurality of DNA segments. Thus, the DNA molecule comprises at least a first and a second DNA segment. The first DNA segment encodes a first module and the second DNA segment encodes a second module. No more than one DNA segment is derived from the eryA gene cluster of *Saccharopolyspora erythraea*. Together the DNA segments encode a recombinant polyhydroxyalkanoate monomer synthase. A preferred embodiment of the invention employs a first DNA segment derived from the vep gene cluster of Streptomyces. Another preferred embodiment of the invention employs a second DNA segment derived from the tyl gene cluster of Streptomyces.

Yet another embodiment of the invention is a method of providing a polyhydroxyalkanoate monomer. The method comprises introducing a DNA molecule into a host cell. The DNA molecule comprises a DNA segment encoding a recombinant polyhydroxyalkanoate monomer synthase operably linked to a promoter functional in the host cell. The DNA encoding the recombinant polyhydroxyalkanoate monomer synthase, which synthase comprises at least a first module and a second module, is expressed in the host cell so as to generate a polyhydroxyalkanoate monomer.

Also provided is a method of preparing a polyhydroxyalkanoate polymer. The method comprises introducing a first DNA molecule and a second DNA molecule into a host cell. The first DNA molecule comprises a DNA segment encoding a recombinant polyhydroxyalkanoate monomer synthase. The recombinant polyhydroxyalkanoate monomer synthase comprises a plurality of modules. Thus, the monomer synthase comprises at least a first module and a second module. The first DNA molecule is operably linked to a promoter functional in a host cell. The second DNA molecule comprises a DNA segment encoding a polyhydroxyalkanoate synthase operably linked to a promoter functional in the host cell. The DNAs encoding the recombinant polyhydroxyalkanoate monomer synthase and polyhydroxyalkanoate synthase are expressed in the host cell so as to generate a polyhydroxyalkanoate polymer.

Yet another embodiment of the invention is an isolated and purified DNA molecule. The DNA molecule comprises a plurality of DNA segments. That is, the DNA molecule comprises at least a first and a second DNA segment. The first DNA segment encodes a fatty acid synthase and the second DNA segment encodes a module of a polyketide synthase. A preferred embodiment of the invention employs a second DNA segment encoding a module which comprises a β-ketoacyl synthase amino-terminal to an acyltransferase which is amino-terminal to a ketoreductase which is amino-terminal to an acyl carrier protein which is amino-terminal to a thioesterase.

The invention also provides a method of preparing a polyhydroxyalkanoate monomer. The method comprises introducing a DNA molecule comprising a plurality of DNA segments into a host cell. Thus, the DNA molecule comprises at least a first and a second DNA segment. The first DNA segment encodes a fatty acid synthase operably linked to a promoter functional in the host cell. The second DNA segment encodes a polyketide synthase. The second DNA segment is located 3' to the first DNA segment. The first DNA segment is linked to the second DNA segment so that the encoded protein is expressed as a fusion protein. The DNA molecule is then expressed in the host cell so as to generate a polyhydroxyalkanoate monomer.

Another embodiment of the invention is an expression cassette comprising a DNA molecule comprising a DNA segment encoding a fatty acid synthase and a polyhydroxyalkanoate synthase.

Also provided is a method of providing a polyhydroxyalkanoate monomer synthase. The method comprises introducing an expression cassette into a host cell. The expression cassette comprises a DNA molecule encoding a polyhydroxyalkanoate monomer synthase operably linked to a promoter functional in the host cell. The monomer synthase comprises a plurality of modules. Thus, the monomer synthase comprises at least a first and second module which together encode the monomer synthase.

A further embodiment of the invention is an isolated and purified DNA molecule comprising a DNA segment which encodes a *Streptomyces venezuelae* polyhydroxyalkanoate monomer synthase, a biologically active variant or subunit thereof. Preferably, the DNA segment encodes a polypeptide having an amino acid sequence comprising SEQ ID NO:2. Preferably, the DNA segment comprises SEQ ID NO:1. The DNA molecules of the invention are double stranded or single stranded. A preferred embodiment of the invention is a DNA molecule that has at least about 70%, more preferably at least about 80%, and even more preferably at least about 90%, identity to the DNA segment comprising SEQ ID NO:1, e.g., a "variant" DNA molecule. A variant DNA molecule of the invention can be prepared by methods well known to the art, including oligonucleotide-mediated mutagenesis. See Adelman et al., *DNA*, 2, 183 (1983) and Sambrook et al., *Molecular Cloning: A Laboratory Manual* (1989).

The invention also provides an isolated, purified polyhydroxyalkanoate monomer synthase, e.g., a polypeptide having an amino acid sequence comprising SEQ ID NO:2, a biologically active subunit, or a biologically active variant thereof. Thus, the invention provides a variant polypeptide having at least about 80%, more preferably at least about 90%, and even more preferably at least about 95%, identity to the polypeptide having an amino acid sequence comprising SEQ ID NO:2. A preferred variant polypeptide, or subunit of a polypeptide, of the invention includes a variant or subunit polypeptide having at least about 10%, more preferably at least about 50% and even more preferably at least about 90%, the activity of the polypeptide having the amino acid sequence comprising SEQ ID NO:2. Preferably, a variant polypeptide of the invention has one or more conservative amino acid substitutions relative to the polypeptide having the amino acid sequence comprising SEQ ID NO:2. For example, conservative substitutions include aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. The biological activity of a polypeptide of the invention can be measured by methods well known to the art.

As used herein, a "linker region" is an amino acid sequence present in a multifunctional protein which is less well conserved in amino acid sequence than an amino acid sequence with catalytic activity.

As used herein, an "extender unit" catalytic or enzymatic domain is an acyl transferase in a module that catalyzes chain elongation by adding 2–4 carbon units to an acyl chain and is located carboxy-terminal to another acyl transferase. For example, an extender unit with methylmalonylCoA specificity adds acyl groups to a methylmalonylCoA molecule.

As used herein, a "polyhydroxyalkanoate" or "PHA" polymer includes, but is not limited to, linked units of related, preferably heterologous, hydroxyalkanoates such as 3-hydroxybutyrate, 3-hydroxyvalerate, 3-hydroxycaproate, 3-hydroxyheptanoate, 3-hydroxyhexanoate, 3-hydroxyoctanoate, 3-hydroxyundecanoate, and 3-hydroxydodecanoate, and their 4-hydroxy and 5-hydroxy counterparts.

As used herein, a "Type I polyketide synthase" is a single polypeptide with a single set of iteratively used active sites. This is in contrast to a Type II polyketide synthase which employs active sites on a series of polypeptides.

As used herein, a "recombinant" nucleic acid or protein molecule is a molecule where the nucleic acid molecule which encodes the protein has been modified in vitro, so that its sequence is not naturally occurring, or corresponds to naturally occurring sequences that are not positioned as they would be positioned in a genome which has not been modified.

As used herein, a "multifunctional protein" is one where two or more enzymatic activities are present on a single polypeptide.

As used herein, a "module" is one of a series of repeated units in a multifunctional protein, such as a Type I polyketide synthase or a fatty acid synthase.

As used herein, a "premature termination product" is a product which is produced by a recombinant multifunctional protein which is different than the product produced by the non-recombinant multifunctional protein. In general, the product produced by the recombinant multifunctional protein has fewer acyl groups.

As used herein, a DNA that is "derived from" a gene cluster, is a DNA that has been isolated and purified in vitro from genomic DNA, or synthetically prepared on the basis of the sequence of genomic DNA.

As used herein, the terms "isolated and/or purified" refer to in vitro isolation of a DNA or polypeptide molecule from its natural cellular environment, and from association with other components of the cell, such as nucleic acid or polypeptide, so that it can be sequenced, replicated and/or expressed. Moreover, the DNA may encode more than one recombinant Type I polyketide synthase and/or fatty acid synthase. For example, "an isolated DNA molecule encoding a polyhydroxyalkanoate monomer synthase" is RNA or DNA containing greater than 7, preferably 15, and more preferably 20 or more sequential nucleotide bases that encode a biologically active polypeptide, fragment, or variant thereof, that is complementary to the non-coding, or complementary to the coding strand, of a polyhydroxyalkanoate monomer synthase RNA, or hybridizes to the RNA or DNA encoding the polyhydroxyalkanoate monomer synthase and remains stably bound under stringent conditions, as defined by methods well known to the art, e.g., in Sambrook et al., supra.

BRIEF DESCRIPTION OF THE FIGURES

FIG. 2: Molecular structure of common bacterial PHAs. Most of the known PHAs are polymers of 3-hydroxy acids possessing the general formula shown. For example, R=CH$_3$ in PHB, R=CH$_2$CH$_3$ in polyhydroxyvalerate (PHV), and R=(CH$_2$)$_4$CH$_3$ in polyhydroxyoctanoate (PHO).

FIG. 8: N-terminal analysis of PHA synthase purified from insect cells. (a) The expected N-terminal 25 amino acid sequence of A. eutrophus PHA synthase. (b&c) The two N-terminal sequences determined for the A. eutrophus PHA synthase produced in insect cells. The bolded sequences are the actual N-termini determined.

Figure 16:
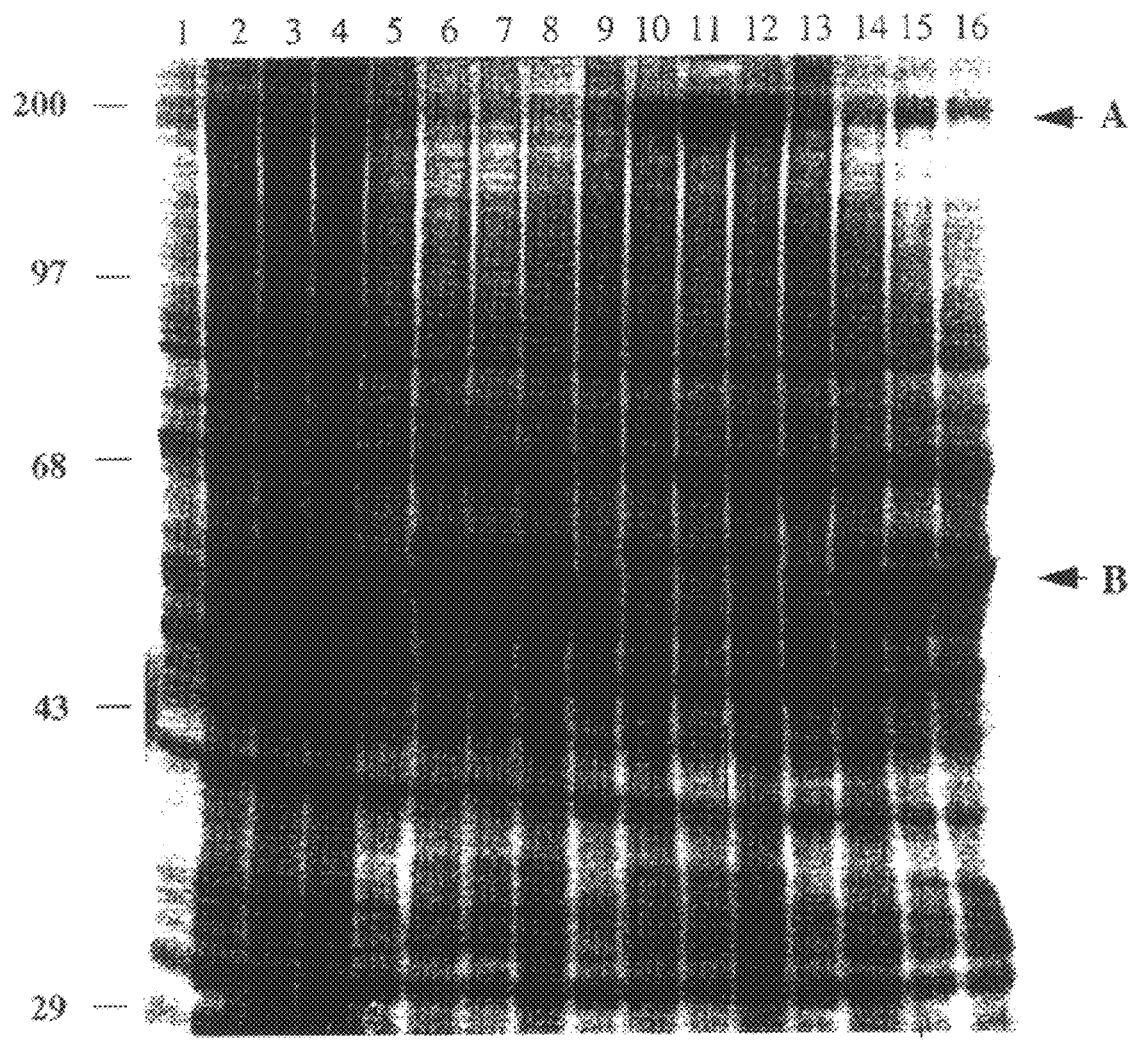

FIG. 16: SDS/PAGE analysis of proteins synthesized at various time-points during infection of Sf21 cells. Approximately 0.5 mg of total cellular protein from various samples was fractionated on a 10% polyacrylamide gel. Samples include: uninfected cells, lanes 1–4, days 0, 1, 2, 3 respectively; infection with BacPAK6::phbC alone, lanes 5–8, days 0, 1, 2, 3 respectively; infection with baculoviral clone containing ratFAS206 alone, lanes 9–12, days 0, 1, 2, 3 respectively; and ratFAS206 and BacPAK6 infected cells, lanes 13–16 days 0, 1, 2, 3, respectively. A=mobility of FAS, B=mobility of PHA synthase. Molecular weight standard lanes are marked M.

Figure 17:
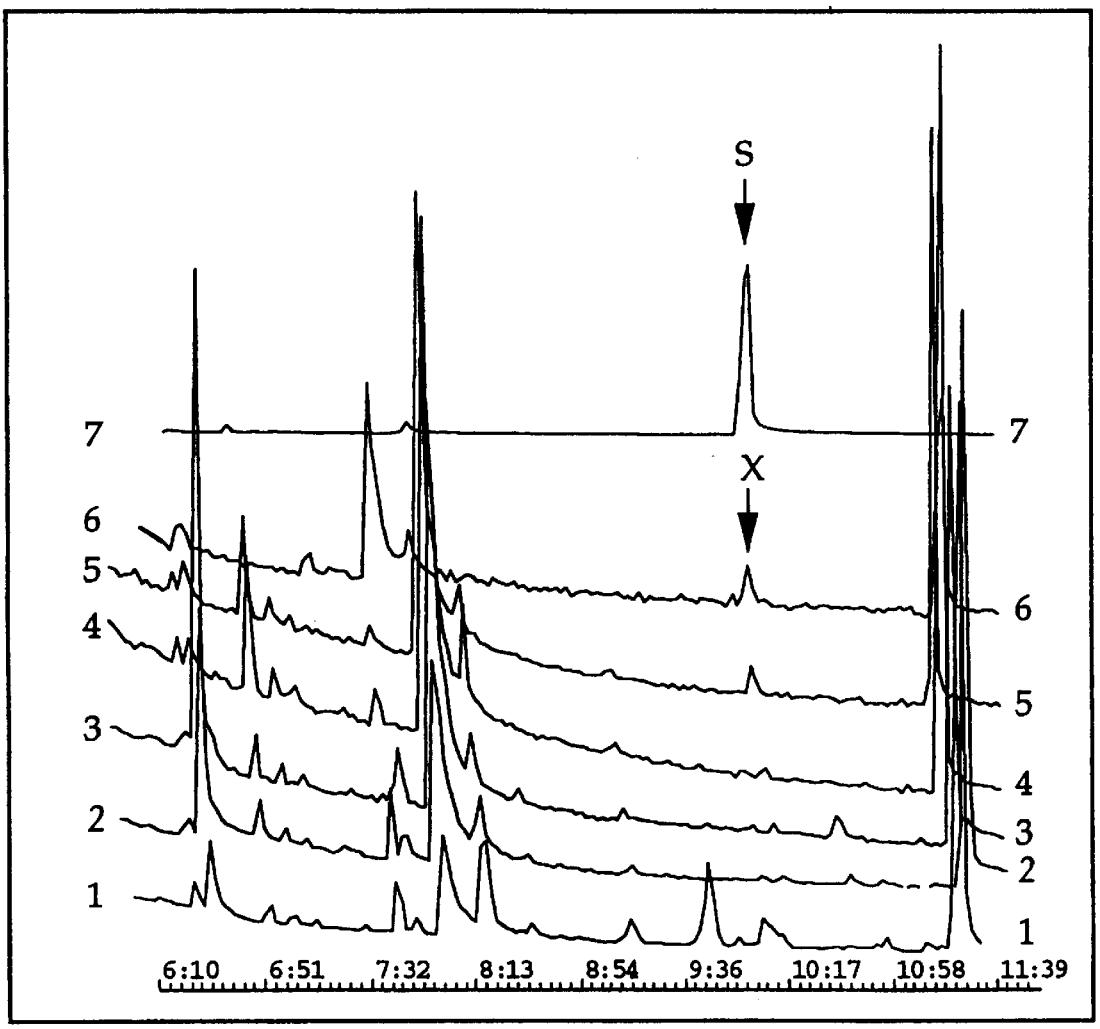

FIG. 17: Gas chromatographic evidence for PHB accumulation in Sf21 cells. Gas chromatograms from various samples are superimposed. PHB standard (Sigma) is chromatogram #7 showing a propylhydroxybutyrate elution time of 10.043 minutes (s, arrow). The gas chromatograms of extracts of the uninfected (#1); singly infected with ratFAS206 (#2, day 3); and singly infected with PHA synthase (#3, day 3) are shown at the bottom of the figure. Gas chromatograms of extracts of dual-infected cells at day 1 (#4), 2 (#5), and 3 (#6) are also shown exhibiting a peak eluting at 10.096 minutes (x, arrow). The peak of dual-infected, day 3 extract (#6) was used for mass spectrometry (MS) analysis.

Figure 18:
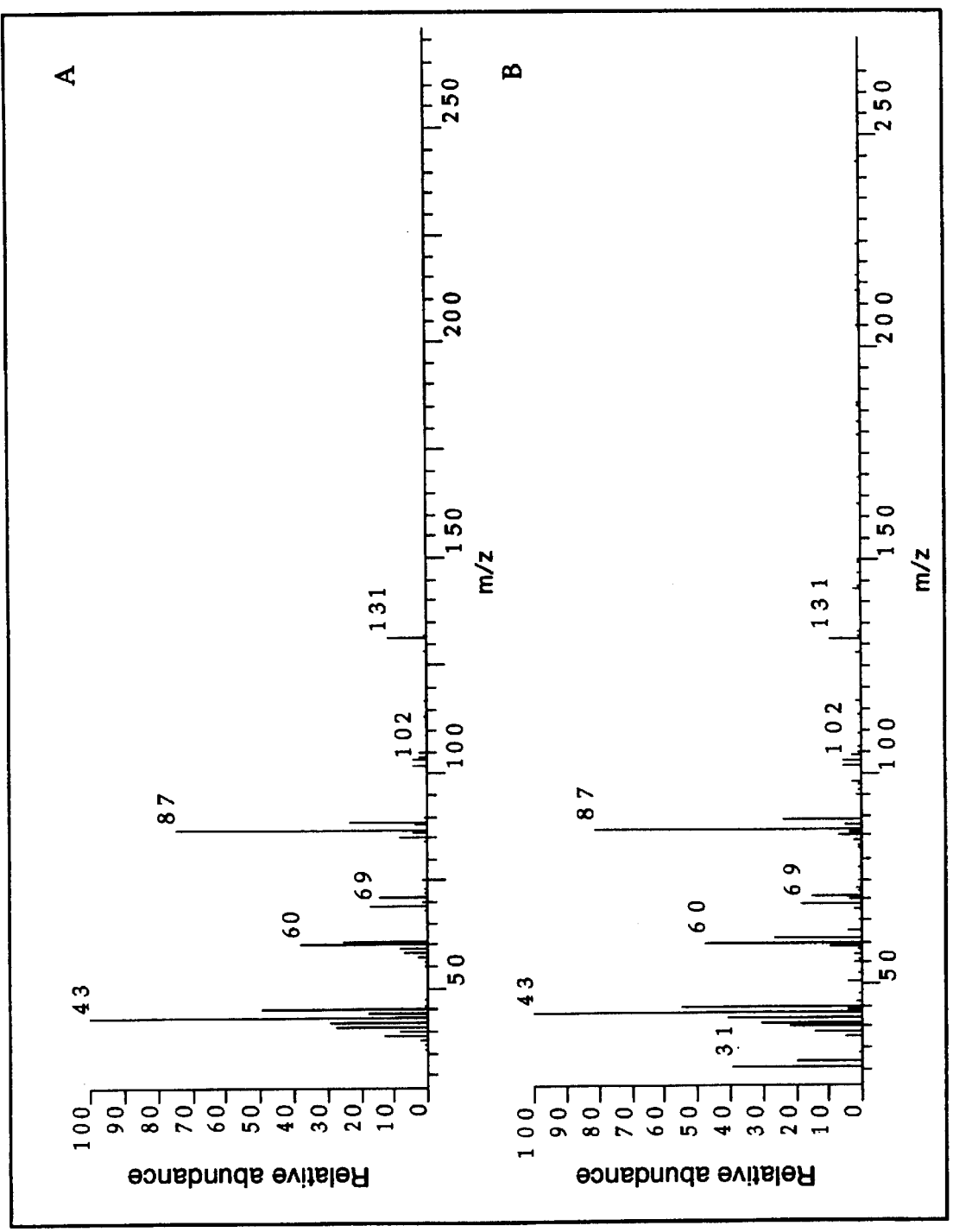

FIG. 18: Gas-chromatography-mass spectrometry analysis of PHB. The characteristic fragmentation of propylhydroxybutyrate at m/z of 43, 60, 87, and 131 is shown. A) standard PHB from bacteria (Sigma), and B) peak X from ratFAS206 and BacPAK6: phbC baculovirus infected, day 3 (#6, FIG. 17) Sf21 cells expressing rat FAS dehydrase inactivated protein and PHA synthase.

FIG. 19: Map of the vep (*Streptomyces venezuelae* polyene encoding) gene cluster.

Figure 20:
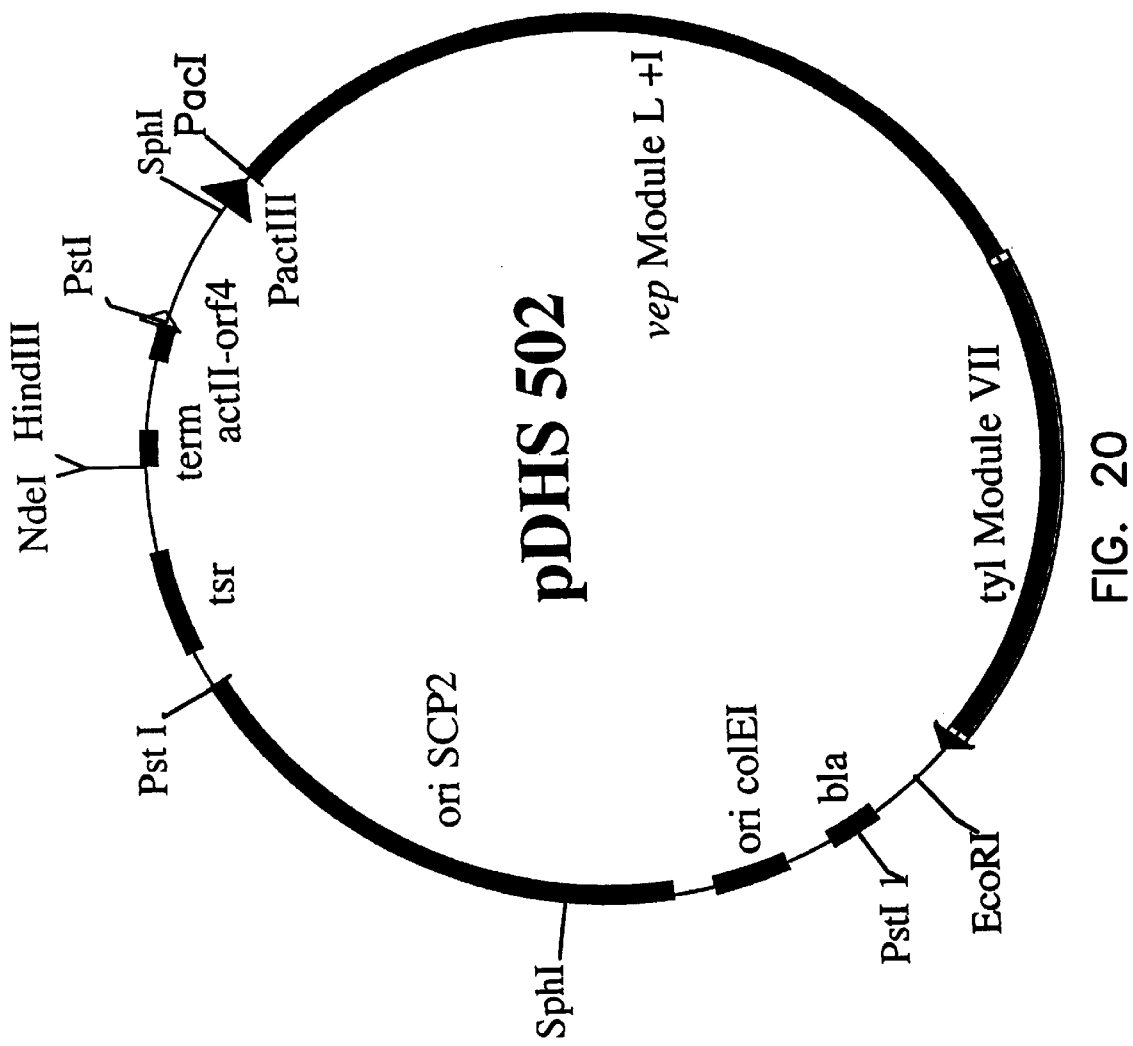

FIG. 20: Plasmid map of pDHS502.

Figure 21:
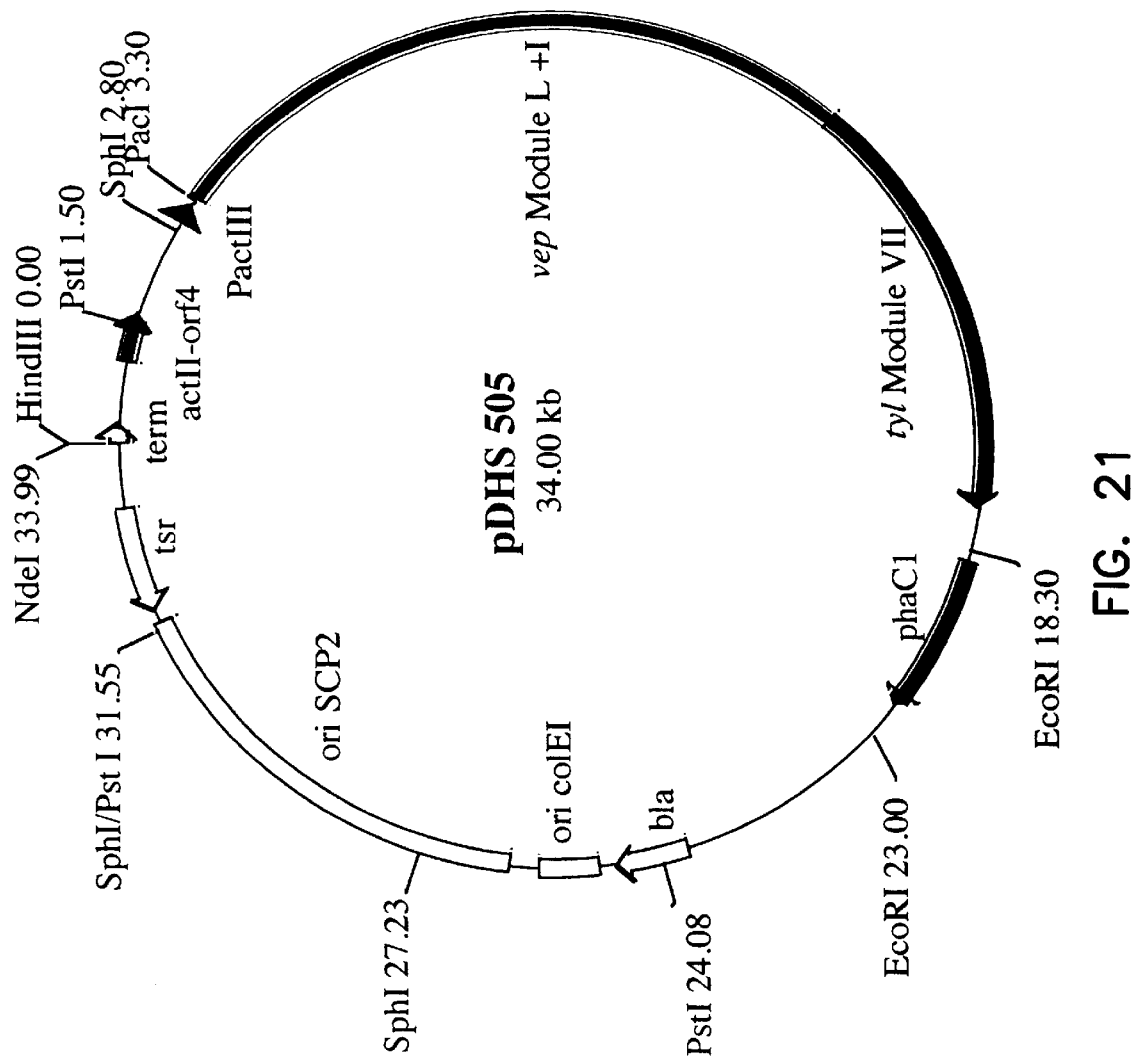

FIG. 21: Plasmid map of pDHS505.

FIG. 22: Cloning protocol for pDHS505.

FIGS. 23A–K: Nucleotide sequence (SEQ ID NO:1) and corresponding amino acid sequence (SEQ ID NO:2) of the vep ORFI.

DETAILED DESCRIPTION OF THE INVENTION

The invention described herein can be used for the production of a diverse range of biodegradable PHA polymers through genetic redesign of DNA encoding a FAS or Streptomyces spp. Type I PKS polypeptide to provide a recombinant PHA monomer synthase. Different PHA synthases can then be tested for their ability to polymerize the monomers produced by the recombinant PHA synthase into a biodegradable polymer. The invention also provides a method by which various PHA synthases can be tested for their specificity with respect to different monomer substrates.

The potential uses and applications of PHAs produced by PHA monomer synthases and PHA synthases includes both medical and industrial applications. Medical applications of PHAs include surgical pins, sutures, staples, swabs, wound dressings, blood vessel replacements, bone replacements and plates, stimulation of bone growth by piezoelectric properties, and biodegradable carrier for long-term dosage of pharmaceuticals. Industrial applications of PHAs include disposable items such as baby diapers, packaging containers, bottles, wrappings, bags, and films, and biodegradable carriers for long-term dosage of herbicides, fungicides, insecticides, or fertilizers.

In animals, the biosynthesis of fatty acids de novo from malonyl-CoA is catalyzed by FAS. For example, the rat FAS is a homodimer with a subunit structure consisting of 2505 amino acid residues having a molecular weight of 272,340 Da. Each subunit consists of seven catalytic activities in separate physical domains (Amy et al., *Proc. Natl. Acad. Sci. USA*, 86, 3114 (1989)). The physical location of six of the catalytic activities, ketoacyl synthase (KS), malonyl/acetyltransferase (M/AT), enoyl reductase (ER), ketoreductase (KR), acyl carrier protein (ACP), and thioesterase (TE), has been established by (1) the identification of the various active site residues within the overall amino acid sequence by isolation of catalytically active fragments from limited proteolytic digests of the whole FAS, (2) the identification of regions within the FAS that exhibit sequence similarity with various monofunctional proteins, (3) expression of DNA encoding an amino acid sequence with catalytic activity to produce recombinant proteins, and (4) the identification of DNA that does not encode catalytic activity, i.e., DNA encoding a linker region. (Smith et al., *Proc. Natl. Acad. Sci. USA*, 73, 1184 (1976); Tsukamoto et al., *J. Biol. Chem.*, 263, 16225 (1988); Rangan et al., *J. Biol. Chem.*, 266, 19180 (1991)).

The seventh catalytic activity, dehydrase (DH), was identified as physically residing between AT and ER by an amino acid comparison of FAS with the amino acid sequences encoded by the three open reading frames of the eryA polyketide synthase (PKS) gene cluster of *Saccharopolyspora erythraea*. The three polypeptides that comprise this PKS are constructed from "modules" which resemble animal FAS, both in terms of their amino acid sequence and in the ordering of the constituent domains (Donadio et al., *Gene*, 111, 51 (1992); Benh et al., *Eur. J. Biochem.* 204, 39 (1992)).

One embodiment of the invention employs a FAS in which the DH is inactivated (FAS DH-). The FAS DH- employed in this embodiment of the invention is preferably a eukaryotic FAS DH- and, more preferably, a mammalian FAS DH-. The most preferred embodiment of the invention is a FAS where the active site in the DH has been inactivated by mutation. For example, Joshi et al. (*J. Biol. Chem.*, 268, 22508 (1993)) changed the His$^{878}$ residue in the rat FAS to an alanine residue by site directed mutagenesis. In vitro studies showed that a FAS with this change (ratFAS206) produced 3-hydroxybutyrylCoA as a premature termination product from acetyl-CoA, malonyl-CoA and NADPH.

As shown below, a FAS DH- effectively replaces the β-ketothiolase and acetoacetyl-CoA reductase activities of the natural pathway by producing D(−)-3-hydroxybutyrate as a premature termination product, rather than the usual 16-carbon product, palmitic acid. This premature termination product can then be incorporated into PHB by a PHB synthase (See Example 2).

Another embodiment of the invention employs a recombinant Streptomyces spp. PKS to produce a variety of β-hydroxyCoA esters that can serve as monomers for a PHA synthase. One example of a DNA encoding a Type I PKS is the eryA gene cluster, which governs the synthesis of erythromycin aglycone deoxyerythronolide B (DEB). The gene cluster encodes six repeated units, termed modules or synthase units (SUs). Each module or SU, which comprises a series of putative FAS-like activities, is responsible for one of the six elongation cycles required for DEB formation. Thus, the processive synthesis of asymmetric acyl chains found in complex polyketides is accomplished through the use of a programmed protein template, where the nature of the chemical reactions occurring at each point is determined by the specificities in each SU.

Two other Type I PKS are encoded by the tyl (tylosin) (FIG. 4) and met (methymycin) (FIG. 5) gene clusters. The macrolide multifunctional synthases encoded by tyl and met provide a greater degree of metabolic diversity than that found in the eryA gene cluster. The PKSs encoded by the eryA gene cluster only catalyze chain elongation with methylmalonylCoA, as opposed to tyl and met PKSs, which catalyze chain elongation with malonylCoA, methylmalonylCoA and ethylmalonylCoA. Specifically, the tyl PKS includes two malonylCoA extender units and one ethylmalonylCoA extender unit, and the met PKS includes one malonylCoA extender unit. Thus, a preferred embodiment of the invention includes, but is not limited to, replacing catalytic activities encoded in met PKS open reading frame 1 (ORF1) to provide a DNA encoding a protein that possesses the required keto group processing capacity and short chain acylCoA ester starter and extender unit specificity necessary to provide a saturated β-hydroxyhexanoylCoA or unsaturated β-hydroxyhexenoylCoA monomer.

In order to manipulate the catalytic specificities within each module, DNA encoding a catalytic activity must remain undisturbed. To identify the amino acid sequences between the amino acid sequences with catalytic activity, the "linker regions," amino acid sequences of related modules, preferably those encoded by more than one gene cluster, are compared. Linker regions are amino acid sequences which are less well conserved than amino acid sequences with catalytic activity. Witkowski et al., *Eur. J. Biochem.,* 198, 571 (1991).

Figure 6:
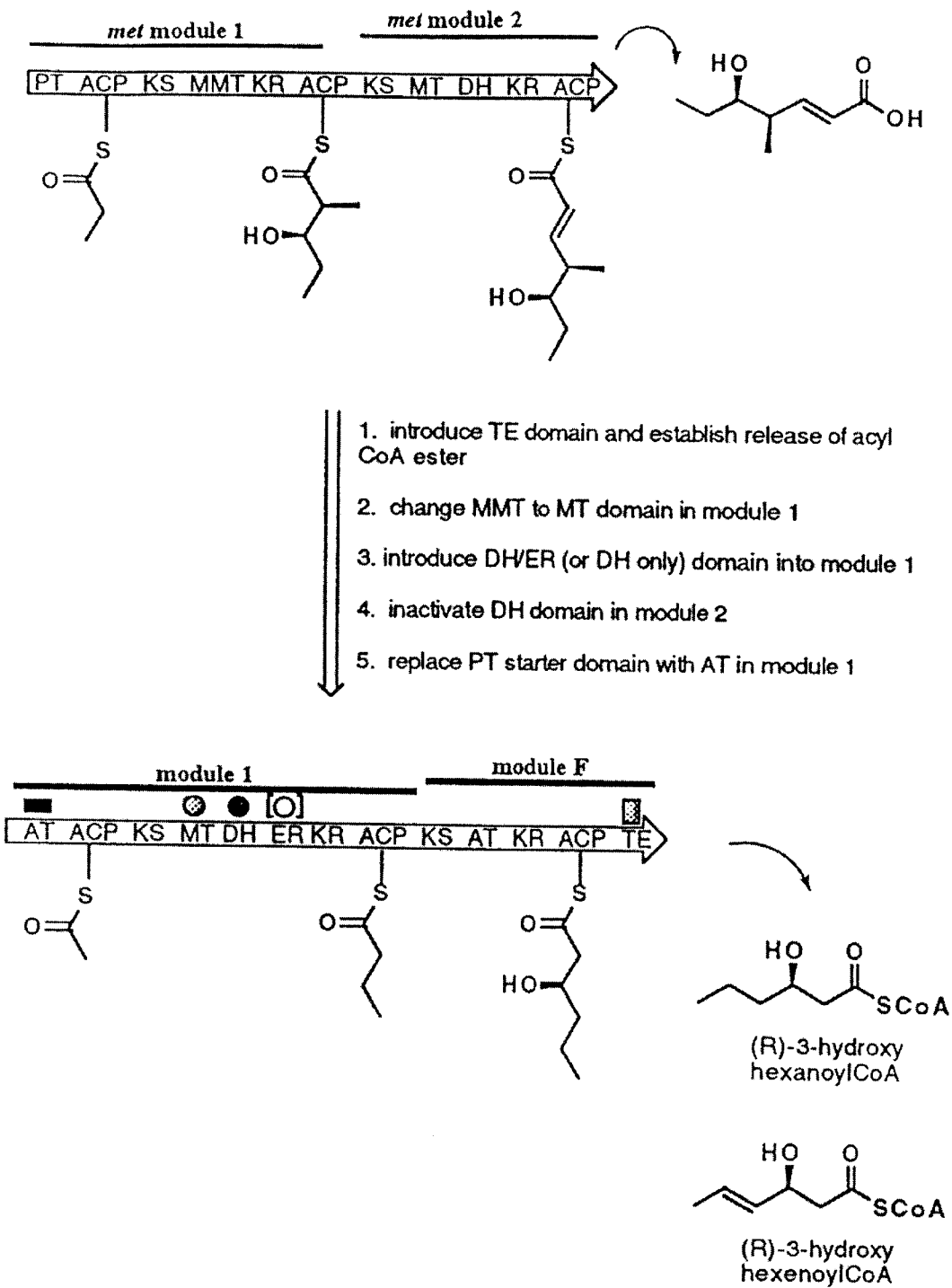
FIG. 6: Strategy for producing a recombinant PHA monomer synthase by domain replacement.

In an alternative embodiment of the invention, to provide a DNA encoding a Type I PKS module with a TE and lacking a functional DH, a DNA encoding a module F, containing KS, MT, KR, ACP, and TE catalytic activities, is introduced at the 3' end of a DNA encoding a first module (FIG. 6). Module F introduces the final (R)-3-hydroxyl acyl group at the final step of PHA monomer synthesis, as a result of the presence of a TE domain. DNA encoding a module F is not present in the eryA PKS gene cluster (Donadio et al., supra, 1991).

A DNA encoding a recombinant monomer synthase is inserted into an expression vector. The expression vector employed varies depending on the host cell to be transformed with the expression vector. That is, vectors are employed with transcription, translation and/or post-translational signals, such as targeting signals, necessary for efficient expression of the genes in various host cells into which the vectors are introduced. Such vectors are constructed and transformed into host cells by methods well known in the art. See Sambrook et al., *Molecular Cloning: A Laboratory Manual,* Cold Spring Harbor (1989). Preferred host cells for the vectors of the invention include insect, bacterial, and plant cells. Preferred insect cells include *Spodoptera frugiperda* cells such as Sf21, and *Trichoplusia ni* cells. Preferred bacterial cells include *Escherichia coli,* Streptomyces and Pseudomonas. Preferred plant cells include monocot and dicot cells, such as maize, rice, wheat, tobacco, legumes, carrot, squash, canola, soybean, potato, and the like.

Moreover, the appropriate subcellular compartment in which to locate the enzyme in eukaryotic cells must be considered when constructing eukaryotic expression vectors. Two factors are important: the site of production of the acetyl-CoA substrate, and the available space for storage of the PHA polymer. To direct the enzyme to a particular subcellular location, targeting sequences may be added to the sequences encoding the recombinant molecules.

The baculovirus system is particularly amenable to the introduction of DNA encoding a recombinant FAS or a PKS monomer synthase because an increasing variety of transfer plasmids are becoming available which can accommodate a large insert, and the virus can be propagated to high titers. Moreover, insect cells are adapted readily to suspension culture, facilitating relatively large scale recombinant protein production. Further, recombinant proteins tend to be produced exclusively as soluble proteins in insect cells, thus, obviating the need for refolding, a task that might be particularly daunting in the case of a large multifunctional protein. The Sf21/baculovirus system has routinely expressed milligram quantities of catalytically active recombinant fatty acid synthase. Finally, the baculovirus/insect cell system provides the ability to construct and analyze different synthase proteins for the ability to polymerize monomers into unique biodegradable polymers.

A further embodiment of the invention is the introduction of at least one DNA encoding a PHA synthase and a DNA encoding a PHA monomer synthase into a host cell. Such synthases include, but are not limited to, *A. eutrophus* 3-hydroxy, 4-hydroxy, and 5-hydroxy alkanoate synthases, *Rhodococcus ruber* $C_3$–$C_5$ hydroxyalkanoate synthases, *Pseudomonas oleororans* $C_6$–$C_{14}$ hydroxyalkanoate synthases, *P. putida* $C_6$–$C_{14}$ hydroxyalkanoate synthases, *P. aeruginosa* $C_5$–$C_{10}$ hydroxyalkanoate synthases, *P. resinovorans* $C_4$–$C_{10}$ hydroxyalkanoate synthases, *Rhodospirillum rubrum* $C_4$–$C_7$ hydroxyalkanoate synthases, *R. gelatinorus* $C_4$–$C_7$, *Thiocapsa pfennigii* $C_4$–$C_8$ hydroxyalkanoate synthases, and *Bacillus megaterium* $C_4$–$C_5$ hydroxyalkanoate synthases.

The introduction of DNA(s) encoding more than one PHA synthase may be necessary to produce a particular PHA polymer due to the specificities exhibited by different PHA synthases. As multifunctional proteins are altered to produce unusual monomeric structures, synthase specificity may be problematic for particular substrates. Although the *A. eutrophus* PHB synthase utilizes only C4 and C5 compounds as substrates, it appears to be a good prototype synthase for initial studies since it is known to be capable of producing copolymers of 3-hydroxybutyrate and 4-hydroxybutyrate (Kunioka et al., *Macromolecules,* 22, 694 (1989)) as well as copolymers of 3-hydroxyvalerate, 3-hydroxybutyrate, and 5-hydroxyvalerate (Doi et al., *Macromolecules,* 19, 2860 (1986)). Other synthases, especially those of *Pseudomonas aeruginosa* (Timm et al., *Eur. J. Biochem.,* 209, 15 (1992)) and *Rhodococcus ruher* (Pieper et al., *FEMS Microbiol. Lett.,* 92, 73 (1992)), can also be employed in the practice of the invention. Synthase specificity may be alterable through molecular biological methods.

In yet another embodiment of the invention, a DNA encoding a FAS and a PHA synthase can be introduced into a single expression vector, obviating the need to introduce the genes into a host cell individually.

A further embodiment of the invention is the generation of a DNA encoding a recombinant multifunctional protein, which comprises a FAS, of either eukaryotic or prokaryotic origin, and a PKS module F. Module F will carry out the final chain extension to include two additional carbons and the reduction of the β-keto group, which results in a (R)-3-hydroxy acyl CoA moiety.

To produce this recombinant protein, DNA encoding the FAS TE is replaced with a DNA encoding a linker region which is normally found in the ACP-KS interdomain region of bimodular ORFs. DNA encoding a module F is then inserted 3' to the DNA encoding the linker region. Different linker regions, such as those described below, which vary in length and amino acid composition, can be tested to determine which linker most efficiently mediates or allows the required transfer of the nascent saturated fatty acid intermediate to module F for the final chain elongation and keto reduction steps. The resulting DNA encoding the protein can then be tested for expression of long chain β-hydroxy fatty acids in insect cells, such as Sf21 cells, or Streptomyces, or Pseudomonas. The expected 3-hydroxy C-18 fatty acid can serve as a potential substrate for PHA synthases which are able to accept long chain alkyl groups. A preferred embodiment of the invention is a FAS that has a chain length specificity between 4–22 carbons.

Examples of linker regions that can be employed in this embodiment of the invention include, but are not limited to, the ACP-KS linker regions encoded by the tyl ORFI ($ACP_1$-$KS_2$; $ACP_2$-$KS_3$), and ORF3 ($ACP_5$-$KS_6$), and eryA ORFI ($ACP_1$-$KS_1$; $ACP_2$-$KS_2$), ORF2 ($ACP_3$-$KS_4$) and ORF3 ($ACP_5$-$KS_6$).

This approach can also be used to produce shorter chain fatty acid groups by limiting the ability of the FAS unit to generate long chain fatty acids. Mutagenesis of DNA encoding various FAS catalytic activities, starting with the KS, may result in the synthesis of short chain (R)-3-hydroxy fatty acids.

The PHA polymers are then recovered from the biomass. Large scale solvent extraction can be used, but is expensive. An alternative method involving heat shock with subsequent enzymatic and detergent digestive processes is also available (Byron, *Trends Biotechnical,* 5, 246 (1987); Holmes, In: *Developments in Crystalline Polymers,* D. C. Bassett (ed), pp. 1–65 (1988)). PHB and other PHAs are readily extracted from microorganisms by chlorinated hydrocarbons. Refluxing with chloroform has been extensively used; the resulting solution is filtered to remove debris and concentrated, and the polymer is precipitated with methanol or ethanol, leaving low-molecular-weight lipids in solution. Longer-side-chain PHAs show a less restricted solubility than PHB and are, for example, soluble in acetone. Other strategies adopted include the use of ethylene carbonate and propylene carbonate as disclosed by Lafferty et al. (*Chem. Rundschau,* 30, 14 (1977)) to extract PHB from biomass. Scandola et al., (*Int. J. Biol. Microbiol.,* 10, 373 (1988)) reported that 1 M HCl-chloroform extraction of *Rhizobium meliloti* yielded PHB of $M_w=6\times10^4$ compared with $1.4\times10^6$ when acetone was used.

Methods are well known in the art for the determination of the PHB or PHA content of microorganisms, the composition of PHAs, and the distribution of the monomer units in the polymer. Gas chromatography and high-pressure liquid chromatography are widely used for quantitative PHB analysis. See Anderson et al. *Microbiol. Rev.,* 54, 450 (1990) for a review of such methods. NMR techniques can also be used to determine polymer composition, and the distribution of monomer units.

The invention has been described with reference to various specific and preferred embodiments and will be further described by reference to the following detailed examples. It is understood however, that there are many extensive variations, and modifications on the basic theme of the present invention beyond that shown in the examples and description, which are within the spirit and scope of the present invention.

I. Experimental Procedures

Materials and Methods

Materials

Sodium R-(-)-3-hydroxybutyrate, coenzyme-A, ethylchloroformate, pyridine and diethyl ether were purchased from Sigma Chemical Co. Amberlite IR-120 was purchased from Mallinckrodt Inc. 6-O-(N-Heptylcarbamoyl)methyl α-D-glucopyranoside (Hecameg) was obtained from Vegatec (Villeejuif, France). Two-piece spectrophotometer cells with pathlengths of 0.1 (#20/0-Q-1) and 0.01 cm (#20/0-Q-0.1) were obtained from Starna Cells Inc., (Atascadero, Calif.). Rabbit anti-*A. eutrophus* PHA synthase antibody was a gracious gift from Dr. F. Srienc and S. Stoup (Biological Process Technology Institute, University of Minnesota). Sf21 cells and *T. ni* cells were kindly provided by Greg Franzen (R&D Systems, Minneapolis, Minn.) and Stephen Harsch (Department of Veterinary Pathobiology, University of Minnesota), respectively.

Plasmid pFAS206 and a recombinant baculoviral clone encoding FAS206 (Joshi et al., *J. Biol. Chem.,* 268, 22508 (1993)) were generous gifts of A. Joshi and S. Smith. Plasmid pAet41 (Peoples et al., *J. Biol. Chem.,* 264, 15298, (1989)), the source of the *A. eutrophus* PHB synthase, was obtained from A. Sinskey. Baculovirus transfer vector, pBacPAK9, and linearized baculoviral DNA, were obtained from Clontech Inc. (Palo Alto, Calif.). Restriction enzymes, T4 DNA ligase, *E. coli* DH5α competent cells, molecular weight standards, lipofectin reagent, Grace's insect cell medium, fetal bovine serum (FBS), and antibiotic/antimycotic reagent were obtained from GIBCO-BRL (Grand Island, N.Y.). Tissue culture dishes were obtained from Corning Inc. Spinner flasks were obtained from Bellco Glass Inc. Seaplaque agarose GTG was obtained from FMC Bioproducts Inc.

Methods

Preparation of R-3HBCoA. R-(-)-3 HBCoA was prepared by the mixed anhydride method described by Haywood et al., *FEMS Microbiol. Lett.,* 57, 1 (1989). 60 mg (0.58 mmol) of R-(-)-3 hydroxybutyric acid was freeze dried and added to a solution of 72 mg of pyridine in 10 ml diethyl ether at 0° C. Ethylchloroformate (100 mg) was added, and the mixture was allowed to stand at 4° C. for 60 minutes. Insoluble pyridine hydrochloride was removed by centrifugation. The resulting anhydride was added, dropwise with mixing, to a solution of 100 mg coenzyme-A (0.13 mmol) in 4 ml 0.2 M potassium bicarbonate, pH 8.0 at 0° C. The reaction was monitored by the nitroprusside test of Stadtman, *Meth. Enzymol.,* 3, 931 (1957), to ensure sufficient anhydride was added to esterify all the coenzyme-A. The concentration of R-3-HBCoA was determined by measuring the absorbance at 260 nm (e=16.8 mM$^{-1}$ cm$^{-1}$; 18).

Construction of pBP-phbC. The phbC gene (approximately 1.8 kb) was excised from pAet41 (Peoples et al., *J. Biol. Chem.,* 264, 15293 (1989)) by digestion with BstBI and StuI, purified as described by Williams et al. (*Gene,* 109, 445 (1991)), and ligated to pBacPAK9 digested with BstBI and StuI. This resulted in pBP-phbC, the baculovirus transfer vector used in formation of recombinant baculovirus particles carrying phbC.

Large scale expression of PHA synthase. A 1 L culture of *T. ni* cells ($1.2\times10^6$ cells/ml) in logarithmic growth was infected by the addition of 50 ml recombinant viral stock solution ($2.5\times10^8$ pfu/ml) resulting in a multiplicity of infection (MOI) of 10. This infected culture was split between two Bellco spinners (350 ml/500 ml spinner, 700 ml/1 L spinner) to facilitate oxygenation of the culture. These cultures were incubated at 28° C. and stirred at 60 rpm for 60 hours. Infected cells were harvested by centrifugation at 1000×g for 10 minutes at 4° C. Cells were flash-frozen in liquid $N_2$ and stored in 4 equal aliquots, at −80° C. until purification.

Insect cell maintenance and recombinant baculovirus formation. Sf21 cells were maintained at 26–28° C. in Grace's insect cell medium supplemented with 10% FBS, 1.0% pluronic F68, and 1.0% antibiotic/antimycotic (GIBCO-BRL). Cells were typically maintained in suspension at 0.2–2.0×10$^6$/ml in 60 ml total culture volume in 100 ml spinner flasks at 55–65 rpm. Cell viability during the culture period was typically 95–100%. The procedures for use of the transfer vector and baculovirus were essentially those described by the manufacturer (Clontech, Inc.). Purified pBP-phbC and linearized baculovirus DNA were used for cotransfection of Sf21 cells using the liposome mediated method (Felgner et al., *Proc. Natl. Acad. Sci. USA*, 84, 7413 (1987)) utilizing Lipofectin (GIBCO-BRL). Four days later cotransfection supernatants were utilized for plaque purification. Recombinant viral clones were purified from plaque assay plates containing 1.5% Seaplaque GTG after 5–7 days at 28° C. Recombinant viral clone stocks were then amplified in T25-flask cultures (4 ml, 3×10$^6$/ml on day 0) for 4 days; infected cells were determined by their morphology and size and then screened by SDS/PAGE using 10% polyacrylamide gels (Laemmli, *Nature*, 227, 680 (1970)) for production of PHA synthase.

Purification of PHA synthase from BTI-TN-5B1-4 *T. ni* cells. Purification of PHA synthase was performed according to the method of Gerngross et al., *Biochemistry*, 33, 9311 (1994) with the following alterations. One aliquot (110 mg protein) of frozen cells was thawed on ice and resuspended in 10 mM KPi (pH 7.2), 5% glycerol, and 0.05% Hecameg (Buffer A) containing the following protease inhibitors at the indicated final concentrations: benzamidine (2 mM), phenylmethylsulfonyl fluoride (PMSF, 0.4 mM), pepstatin (2 mg/ml), leupeptin (2.5 mg/ml), and Na-p-tosyl-1-lysine chloromethyl ketone (TLCK, 2 mM). EDTA was omitted at this stage due to its incompatibility with hydroxylapatite (HA). This mixture was homogenized with three series of 10 strokes each in two Thomas homogenizers while partially submerged in an ice bath and then sonicated for 2 minutes in a Branson Sonifier 250 at 30% cycle, 30% power while on ice. All subsequent procedures were carried out at 4° C.

The lysate was immediately centrifuged at 100000×g in a Beckman 50.2 Ti rotor for 80 minutes, and the resulting supernatant (10.5 ml, 47 mg) was immediately filtered through a 0.45 mm Uniflow filter (Schleicher and Schuell Inc., Keene, N. H.) to remove any remaining insoluble matter. Aliquots of the soluble fraction (1.5 ml, 7 mg) were loaded onto a 5 ml BioRad Econo-Pac HTP column that had been equilibrated with Buffer A (+protease inhibitor mix) attached to a BioRad Econo-system, and the column was washed with 30 ml Buffer A. All chromatographic steps were carried out at a flow rate of 0.8 ml/minute. PHA synthase was eluted from the HA column with a 32×32 ml linear gradient from 10 to 300 mM KPi.

Fraction collection tubes were prepared by addition of 30 ml of 100 mM EDTA to provide a metalloprotease inhibitor at 1 mM immediately after HA chromatography. PHA synthase was eluted in a broad peak between 110–180 mM KPi. Fractions (3 ml) containing significant PHA synthase activity were pooled and stored at 0° C. until the entire soluble fraction had been run through the chromatographic process. Pooled fractions then were concentrated at 4° C. by use of a Centriprep-30 concentrator (Amicon) to 3.8 mg/ml. Aliquots (0.5 ml) were either flash-frozen and stored in liquid $N_2$ or glycerol was added to a final concentration of 50% and samples (1.9 mg/ml) were stored at −20° C.

Western analysis. Samples of *T. ni* cells were fractionated by SDS-PAGE on 10% polyacrylamide gels, and the proteins then were transferred to 0.2 mm nitrocellulose membranes using a BioRad Transblot SD Semi-Dry electrophoretic transfer cell according to the manufacturer. Proteins were transferred for 1 hour at 15 V. The membrane was rinsed with doubly distilled $H_2O$, dried, and treated with phosphate-buffered saline (PBS) containing 0.05% Tween-20 (PBS-Tween) and 3% nonfat dry milk to block non-specific binding sites. Primary antibody (rabbit anti-PHA synthase) was applied in fresh blocking solution and incubated at 25° C. for 2 hours. Membranes were then washed four times for 10 minutes with PBS-Tween followed by the addition of horseradish peroxidase-conjugated goat-anti-rabbit antibody (Boehringer-Mannheim) diluted 10,000× in fresh blocking solution and incubated at 25° C. for 1 hour. Membranes were washed finally in three changes (10 minutes) of PBS, and the immobilized peroxidase label was detected using the chemiluminescent LumiGLO substrate kit (Kirkegaard and Perry, Galthersburg, Md.) and X-ray film.

N-terminal analysis. Approximately 10 mg of purified PHA synthase was run on a 10% SDSpolyacrylamide gel, transferred to PVDF (Immobilon-PSQ, Millipore Corporation, Bedford, Mass.), stained with Amido Black, and sequenced on a 494 Procise Protein Sequencer (Perkin-Elmer, Applied Biosystems Division, Foster City, Calif.).

Double-infection protocol. Four 100 ml spinner flasks were each inoculated with 8×10$^7$ cells in 50 ml of fresh insect medium. To flask 1, an additional 20 ml of fresh insect medium was added (uninfected control); to flask 2, 10 ml BacPAK6::phbC viral stock (1×10$^8$ pfu/ml) and 10 ml fresh insect medium were added; to flask 3, 10 ml BacPAK6::FAS206 viral stock (1×10$^8$ pfu/ml) and 10 ml fresh insect medium were added; and to flask 4, 10 ml BacPAK6::phbC viral stock (1×10$^8$ pfu/ml) and 10 ml BacPAK6::FAS206 viral stock (1×10$^8$ pfu/ml) were added. These viral infections were carried out at a multiplicity of infection of approximately 10. Cultures were maintained under normal growth conditions and 15 ml samples were removed at 24, 48, and 72 hour time points. Cells were collected by gentle centrifugation at 1000×g for 5 minutes, the medium was discarded, and the cells were immediately stored at −70° C.

PHA synthase assays. Coenzyme A released by PHA synthase in the process of polymerization was monitored precisely as described by Gerngross et al. (surra) using 5,5'-dithiobis (2-nitrobenzoic acid, DTNB) (Ellman, *Arch. Biochem. Biophys.*, 82, 70 (1959)).

The presence of HBCoA was monitored spectrophotometrically. Assays were performed at 25° C. in a Hewlett Packard 8452A diode array spectrophotometer equipped with a water jacketed cell holder. Two-piece Starna Spectrosil spectrophotometer cells with pathlengths of 0.1 and 0.01 cm were employed to avoid errors arising from the compression of the absorbance scale at higher values. Absorbance was monitored at 232 nm, and $E_{232}$ nm of 4.5×103 $M^{-1}$ $cm^{-1}$ was used in calculations. One unit (U) of enzyme is the amount required to hydrolyze 1 mmol of substrate minute$^{-1}$. Buffer (0.15 M KPi, pH 7.2) and substrate were equilibrated to 25° C. and then combined in an Eppendorf tube also at 25° C. Enzyme was added and mixed once in the pipet tip used to transfer the entire mixture to the spectrophotometer cell. The two piece cell was immediately assembled, placed in the spectrophotometer with the cell holder (type CH) adapted for the standard 10 mm path length cell holder of the spectrophotometer. Manipulations of sample, from mixing to initiation of monitoring, took only 10–15 seconds. Absorbance was continually monitored for up to 10 minutes. Calibration of reactions was against a solution of buffer and enzyme (no substrate) which lead to absorbance values that represented substrate only.

PHB assay. PHB was assayed from Sf21 cell samples according to the propanolysis method of Riis et al., *J. Chromo.*, 445, 285 (1988). Cell pellets were thawed on ice, resuspended in 1 ml cold dd$H_2$O and transferred to 5 ml screwtop test tubes with teflon seals. 2 ml dd$H_2$O was added, the cells were washed and centrifuged and then 3 ml of acetone were added and the cells washed and centrifuged. The samples were then dessicated by placing them in a 94° C. oven for 12 hours. The following day 0.5 ml of 1,2-dichloroethane, 0.5 ml acidified propanol (20 ml HCl, 80 ml 1-propanol) and 50 ml benzoic acid standard were added and the sealed tubes were heated to 100° C. in a boiling water bath for 2 hours with periodic vortexing. The tubes were cooled to room temperature and the organic phase was used for gas-chromatographic (GC) analysis using a Hewlett Packard 5890A gas-chromatograph equipped with a Hewlett Packard 7673A automatic injector and a fused silica capillary column, DB-WAX 30W of 30 meter length. Positive samples were further subjected to GC-mass spectrometric (MS) analysis for the presence of propylhydroxybutyrate using a Kratos MS25 GC/MS. The following parameters were used: source temperature, 210° C.; voltage, 70 eV; and accelerating voltage, 4 KeV.

Catalytic activities.

Ketoacyl synthase (KS) activity was assessed radiochemically by the condensation-$^{14}CO_2$ exchange reaction (Smith et al., *PNAS USA*, 73, 1184 (1976)).

Transferase (AT) activity was assayed, using malonyl-CoA as donor and pantetheine as acceptor, by determining spectrophotometrically the free CoA released in a coupled ATP citrate-lyase-malate dehydrogenase reaction (see, Rangen et al., *J. Biol. Chem.*, 266, 19180 (1991).

Ketoreductase (KR) was assayed spectrophotometrically at 340 nm: assay systems contained 0.1 M potassium phosphate buffer (pH 7), 0.15 mM NADPH, enzyme and either 10 mM trans-1-decalone or 0.1 mM acetoacetyl-CoA substrate.

Dehydrase (DH) activity was assayed spectrophotometrically at 270 nm using S-DL-$\beta$-hydroxybutyryl N-acetylcysteamine as substrate (Kumar et al., *J. Biol. Chem.*, 245, 4732 (1970)).

Enoyl reductase (ER) activity was assayed spectrophotometrically at 340 nm essentially as described by Strometal (*J. Biol. Chem.*, 254, 8159 (1979)); the assay system contained 0.1 M potassium phosphate buffer (pH 7), 0.15 mM NADPH, 0.375 mM crotonoyl-CoA, 20 $\mu$M CoA and enzyme.

Thioesterase (TE) activity was assessed radiochemically by extracting and assaying the [$^{14}C$]palmitic acid formed from [1-$^{14}C$]palmitoyl-CoA during a 3 minute incubation Smith, *Meth. Enzymol.*, 71C, 181 (1981); the assay was in a final volume of 0.1 ml, 25 mM potassium phosphate buffer (pH 8), 20 $\mu$M [1-$^{14}C$]palmitoyl-CoA (20 nCi) and enzyme.

Assay of overall fatty acid synthase activity was performed spectrophotometrically as described previously by Smith et al. (*Meth. Enzymol.*, 35, 65 (1975)). All enzyme activities were assayed at 37° C. except the transferase, which was assayed at 20° C. Activity units indicate nmol of substrate consumed/minute. All assays were conducted, at a minimum, at two different protein concentrations with the appropriate enzyme and substrate blanks included.

EXAMPLE 1

Expression of *A. eutrophus* PHA synthase using a baculovirus system.

Recent work has shown that PHA synthase from *A. eutrophus* can be overexpressed in *E. coli*, in the absence of 3-ketothiolase and acetoacetyl-CoA reductase (Gemgross et al. supra) and can be expressed in plants (See Poirier et al., *Biotech*, 13, 142 (1995) for a review). Isolation of the soluble form of PHA synthase provides opportunities to examine the mechanistic details of the priming and initiation reactions. Because the baculovirus system has been successful for the expression of a number of prokaryotic genes as soluble proteins, and insect cells, unlike bacterial expression systems, carry out a wide array of posttranslational modifications, the baculovirus expression system appeared ideal for the expression of large quantities of soluble PHA synthase, a protein that must be modified by phosphopantetheine in order to be catalytically active (Gerngross et al., supra).

Purification of PHA synthase. The purification procedure employed for PHA synthase is a modification of Gerngross et al. (supra) involving the elimination of the second liquid chromatographic step and inclusion of a protease-inhibitor cocktail in all buffers. All steps were carried out on ice or at 4° C. except where noted. Frozen cells were thawed on ice in 10 ml of Buffer A (10 mM KPi, pH 7.2, 0.5% glycerol, and 0.05% Hecameg) and then immediately homogenized prior to centrifugation and HA chromatography.

The results of these efforts are summarized in Table 1 and FIG. 7. A prominent band at 64 kDa is visible in total, soluble, and HA eluate protein samples fractionated by SDS/PAGE (lanes 4, 5, and 6 of FIG. 7, respectively). The initial specific activity of the isolated PHA synthase was 20-fold higher than previous attempts at expression and purification of this polypeptide. Approximately 1000 units of PHB synthase have been purified, based on calculations from the direct spectrophotometric assay detailed below, with an overall recovery of activity of 70%. The large proportion of synthase present in the membrane fraction, and the fact that over 90% of the initial activity was found in the soluble fraction, suggests either that the synthase in the membrane fraction is in an inactive form or that the direct assay is not applicable to the initial, 12 U/mg, crude extract.

TABLE 1

Purification of PHA Synthase

| sample | total units | vol (mL) | protein (mg) | (mg/ml) | specific activity | recovery |
|---|---|---|---|---|---|---|
| total protein | 1430 | 11.5 | 113 | 9.8 | 12.7 | 100 |
| soluble protein | 1340 | 10.5 | 47 | 4.5 | 28.6 | 93 |
| pooled HA fractions | 1020 | 7.9 | 30 | 3.8 | 34.2 | 71 |

Figures 7A, 7B:
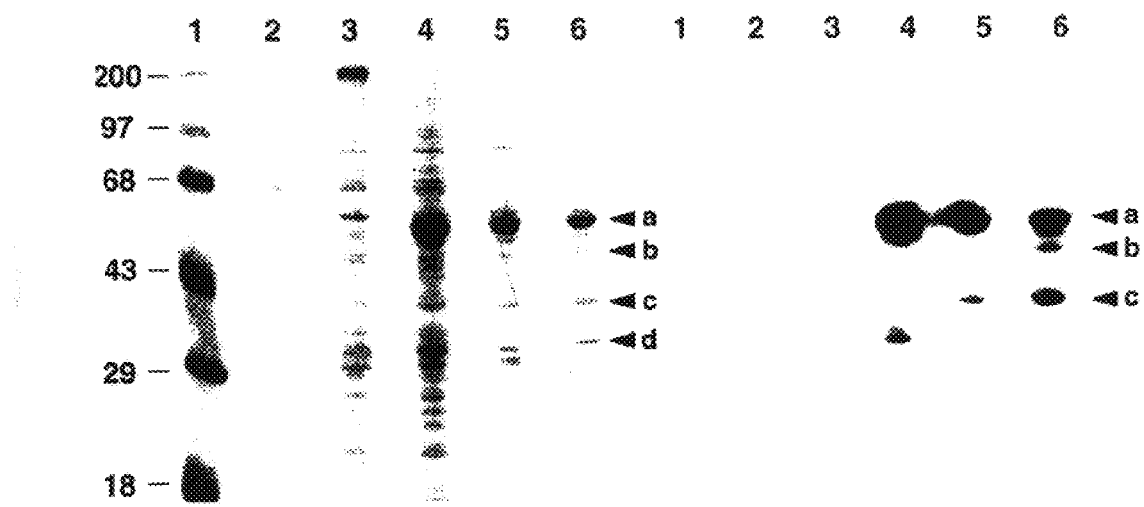
FIGS. 7A and 7B: (A) 10% SDS-PAGE gel showing samples from various stages of the purification of PHA synthase; lane 1, molecular weight markers; lane 2, total protein of uninfected insect cells; lane 3, total protein of insect cells expressing a rat FAS (200 kDa; Joshi et al., Biochem J., 296, 143 (1993)); lane 4, total protein of insect cells expressing PHA synthase; lane 5, soluble protein from sample in lane 4; lane 6, pooled hydroxylapatite (HA) fractions containing PHA synthase. (B) Western analysis of an identical gel using rabbit-α-PHA synthase antibody as probe. Bands designated with arrows are: a, intact PHB synthase with N-terminal alanine at residue 7 and serine at residue 10 (A7/S10); b, 44 kDa fragment of PHB synthase with N-terminal alanine at residue 181 and asparagine at residue 185 (A181/N185); c, PHB synthase fragment of approximately 30 kDa apparently blocked based on resistance to Edman degradation; d, 22 kDa fragment with N-terminal glycine at residue 187 (G187). Band d apparently does not react with rabbit-α-PHB synthase antibody (B, lane 6). The band of similar size in B, lane 4 was not further identified.

N-terminal sequencing of the 64 kDa protein confirmed its identity as PHA synthase (FIG. 8). Two prominent N-termini, at amino acid residue 7 (alanine) and residue 10 (serine) were obtained in a 3:2 ratio. This heterogeneous N-terminus presumably is the result of aminopeptidase activity. Western analysis using a rabbit-anti-PHA synthase antibody corroborated the results of the sequencing and indicated the presence of at least three bands that resulted from proteolysis of PHA synthase (FIG. 7B, Lanes 4–6). The antibody was specific for PHA synthase since neither T. ni nor baculoviral proteins showed reactivity (FIG. 7B, Lanes 2 and 3). N-terminal protein sequencing (FIG. 8) showed directly that the 44 kDa (band b) and 32 kDa (band d) proteins were derived from PHA synthase (fragments beginning at A181/N185 and at G387, respectively). The 35–40 kDa (band c) protein gave low sequencing yields and may contain a blocked N-terminus. Inspection of FIG. 7B suggests that most degradation occurs following cell disruption since the total protein sample for this gel (lane 4) was prepared by boiling intact cells directly in SDS sample buffer while the HA sample (lane 6) went through the purification procedure described above.

Figure 9:
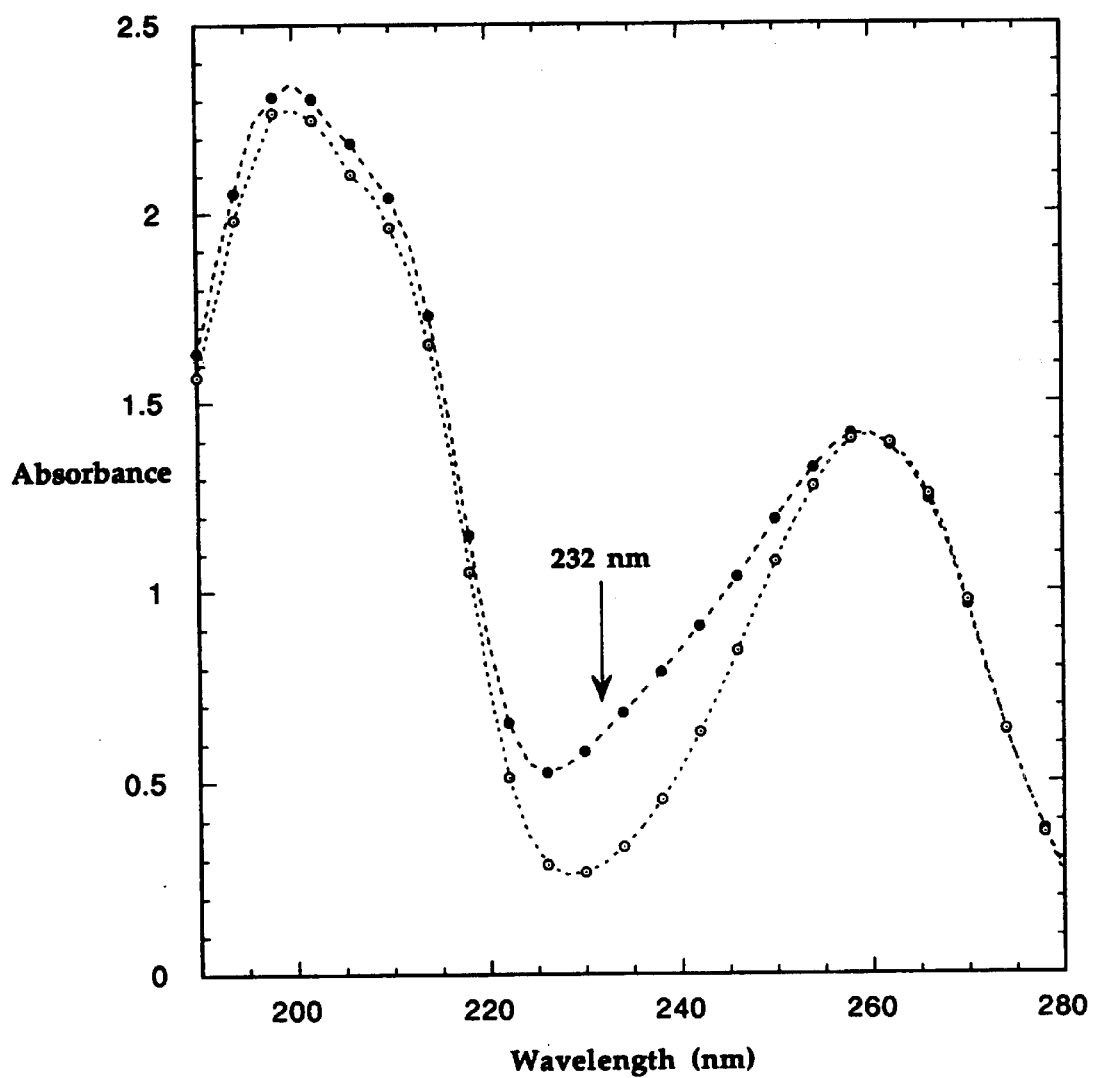
FIG. 9: Spectrophotometric scans of substrate, 3-hydroxybutyrate CoA (HBCoA) and product, CoA. The wavelength at which the direct spectrophotometric assays were carried out (232 nm) is denoted by the arrow; substrate, HBCoA (●) and product, CoA (○).

Assay of Synthase Activity. Due to the significant level of expression obtained using the baculovirus system, the synthase activity could be assayed spectrophotometrically by monitoring hydrolysis of the thioester bond at 232 nm, the wavelength at which there is a maximum decrease in absorbance upon hydrolysis. The difference between substrate (HBCoA) and product (CoA) at this wavelength is shown in FIG. 9. Absorbance of HBCoA and CoA at 232 nm occurs at a trough between two well separated peaks. Assays were carried out at pH 7.2 for comparative analysis with previous studies (Gerngross et al., supra). Substrate (R-(–)3-HBCoA) substrate for these studies was prepared using the mixed anhydride method (Haywood et al., supra), and its concentration was determined by measuring $A_{260}$. The short pathlength cells (0.1 cm and 0.01 cm) allowed use of relatively high reaction concentrations while conserving substrate and enzyme. Assay results showed an initial lag period of 60 seconds prior to the linear decrease in $A_{232}$, and velocities were determined from the slope of these linear regions of the assay curves. The length of the lag period was variable and was inversely related to enzyme concentration. These data are consistent with those using PHA synthase purified from E. coli (Gerngross et al., supra).

Figure 10:
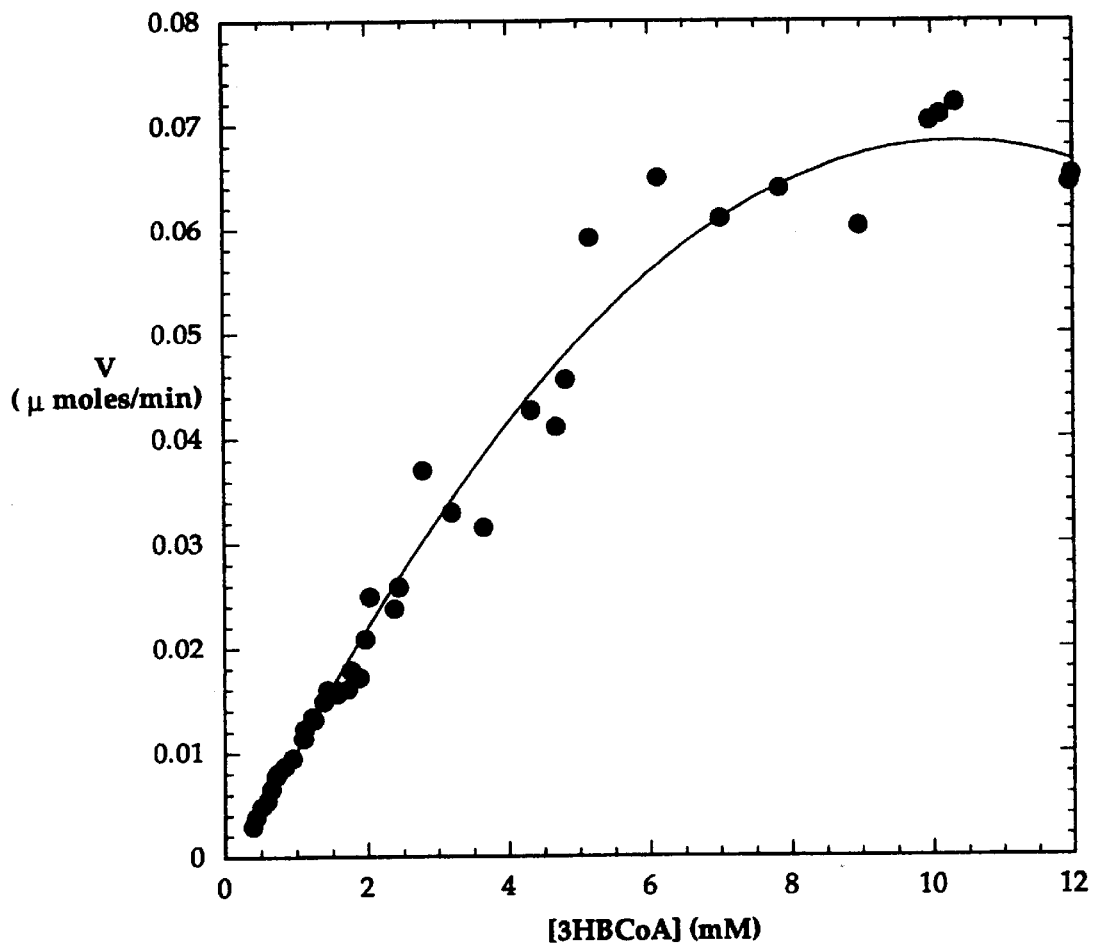
FIG. 10: Velocity of the hydrolysis of HBCoA as a function of substrate concentration. Assays were carried out in 40 or 200 μl assay volumes with enzyme concentration remaining constant at 0.95 mg/ml (3.8 μg/40 μl assay). Velocities were calculated from the linear portions of the assay curves subsequent to the characteristic lag period. The substrate concentration at half-optimal velocity, the apparent $K_m$ value, was estimated to be 2.5 mM from this data.
Figure 11:
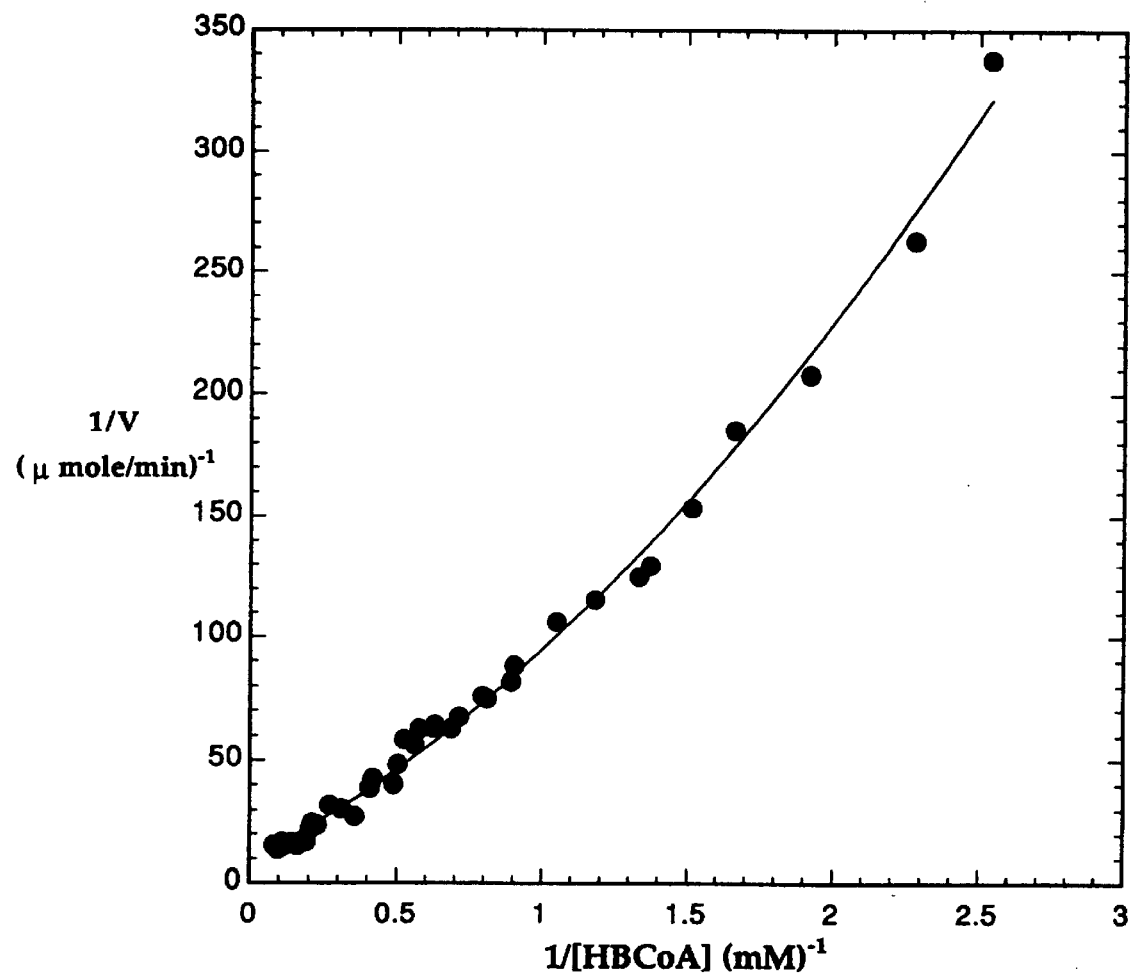
FIG. 11: Double reciprocal plot of velocity versus substrate concentration. The concave upward shape of this plot is similar to results obtained by Fukui et al. (Arch. Microbiol., 110, 149 (1976)) with granular PHA synthase from Z. ramigera.
Figure 12:
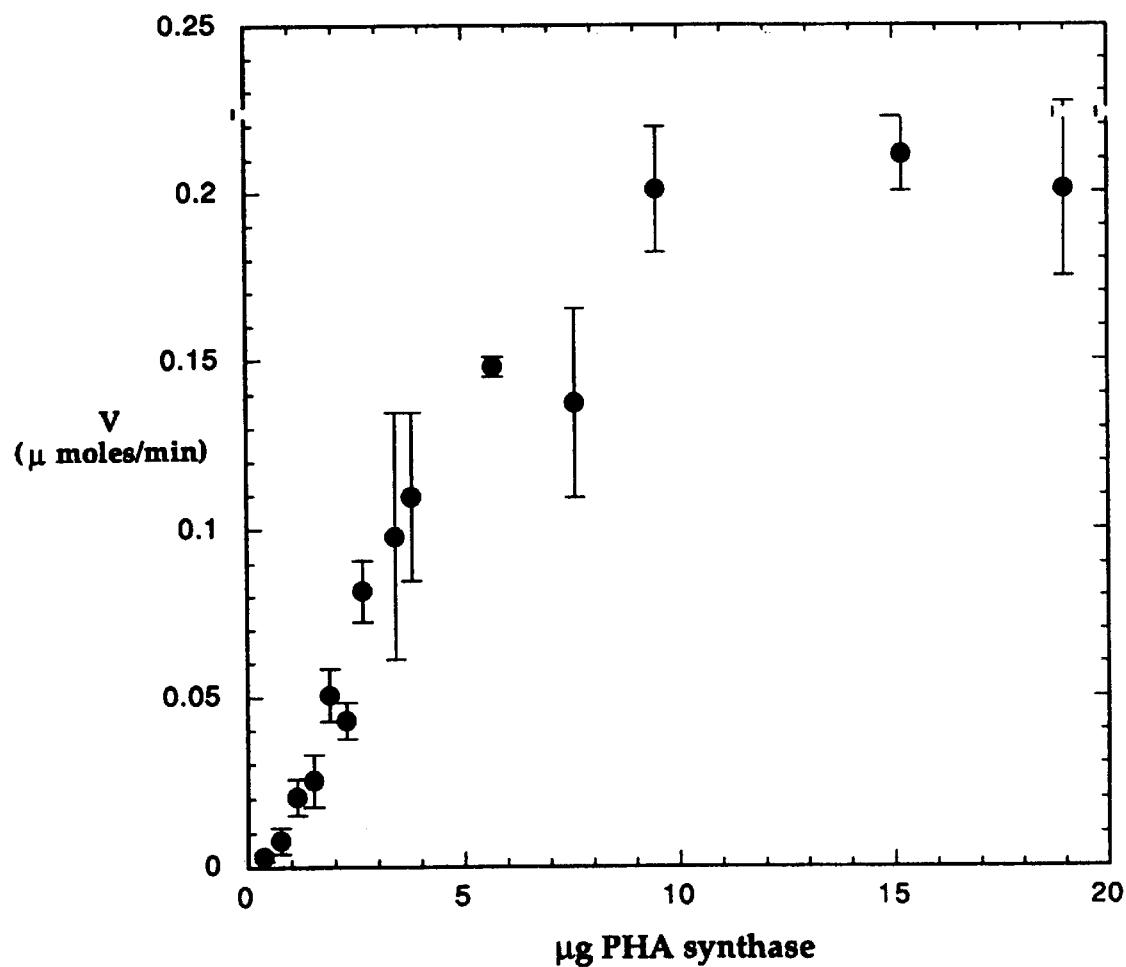
FIG. 12: Velocity of the hydrolysis of HBCoA as a function of enzyme concentration. Assays were carried out in 40 μl assay volumes with the concentration HBCoA remaining constant at 8 μl.
Figure 13:
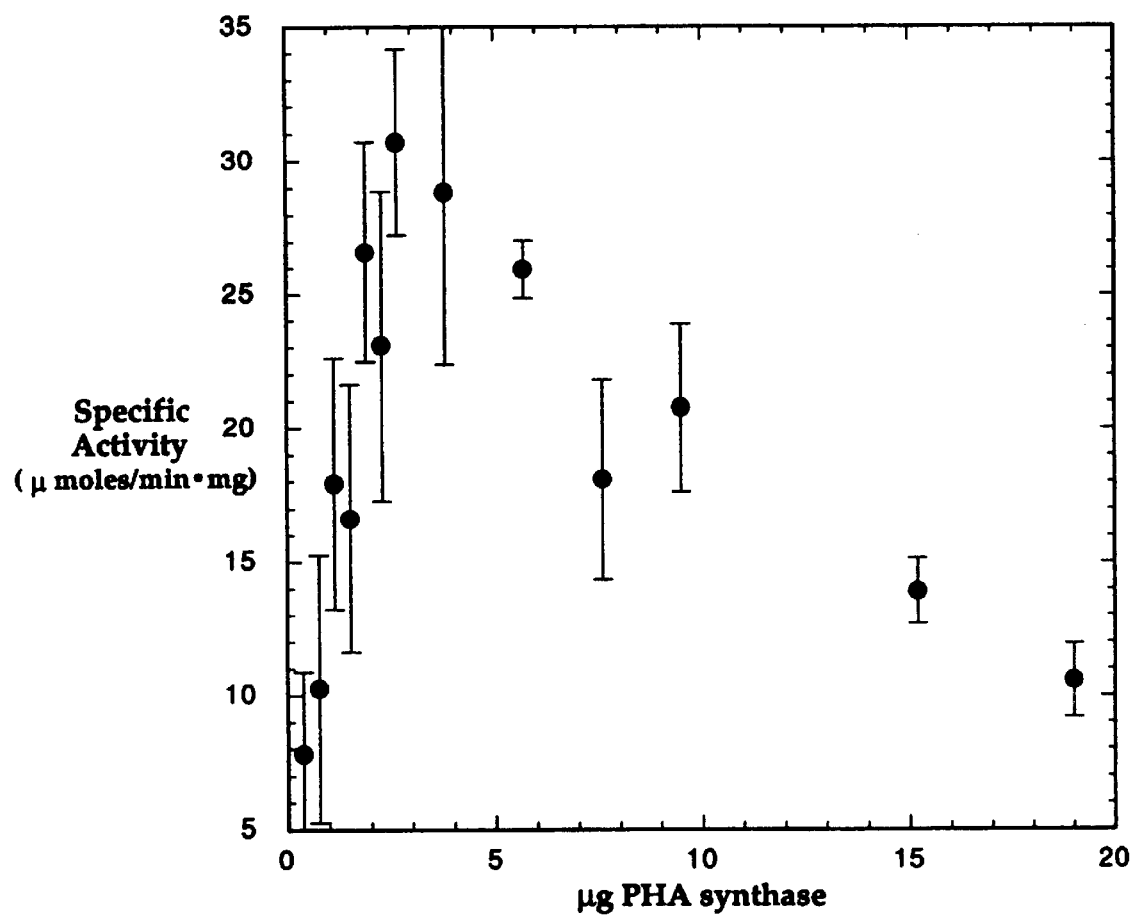
FIG. 13: Specific activity of PHA synthase as a function of enzyme concentration.
Figure 14:
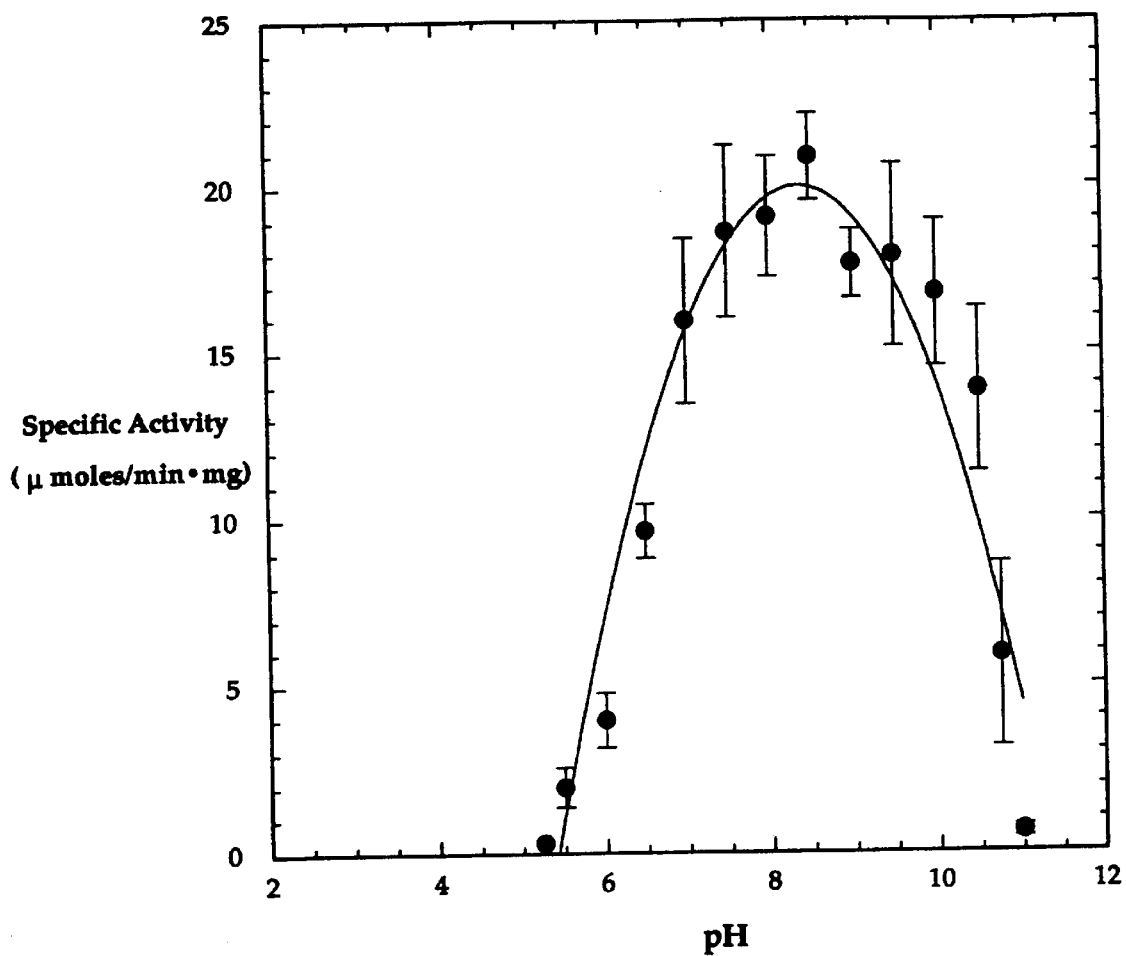
FIG. 14: pH activity curve for soluble PHA synthase produced using the baculovirus system. Reactions were carried out in the presence of 200 mM P$_i$. Buffers of pH<10 were prepared with potassium phosphate, while buffers of pH>10 were prepared with the appropriate proportion of Na$_3$PO$_4$.

FIGS. 10 and 11 show the V versus S and 1/V versus 1/S plots, respectively. The double reciprocal plot was concave upward which is similar to results obtained from studies of the granular PHA synthase from Zooglea ramigera (Fukui et al., Arch. Microbiol., 110, 149 (1976)) and suggests a complex reaction mechanism. Examinations of velocity and specific activity as a function of enzyme concentration are shown in FIGS. 12 and 13. These results confirm that specific activity of the synthase depends upon enzyme concentration. The pH activity curve for A. eutrophus PHA synthase purified from T. ni cells is shown in FIG. 14. The curve shows a broad activity maximum centered around pH 8.5. This result agrees well with prior work on the A. eutrophus PHB synthase although it is significantly different than results obtained for the PHB synthase from Z. ramigera for which the optimum was determined to be pH 7.0.

Figure 15:
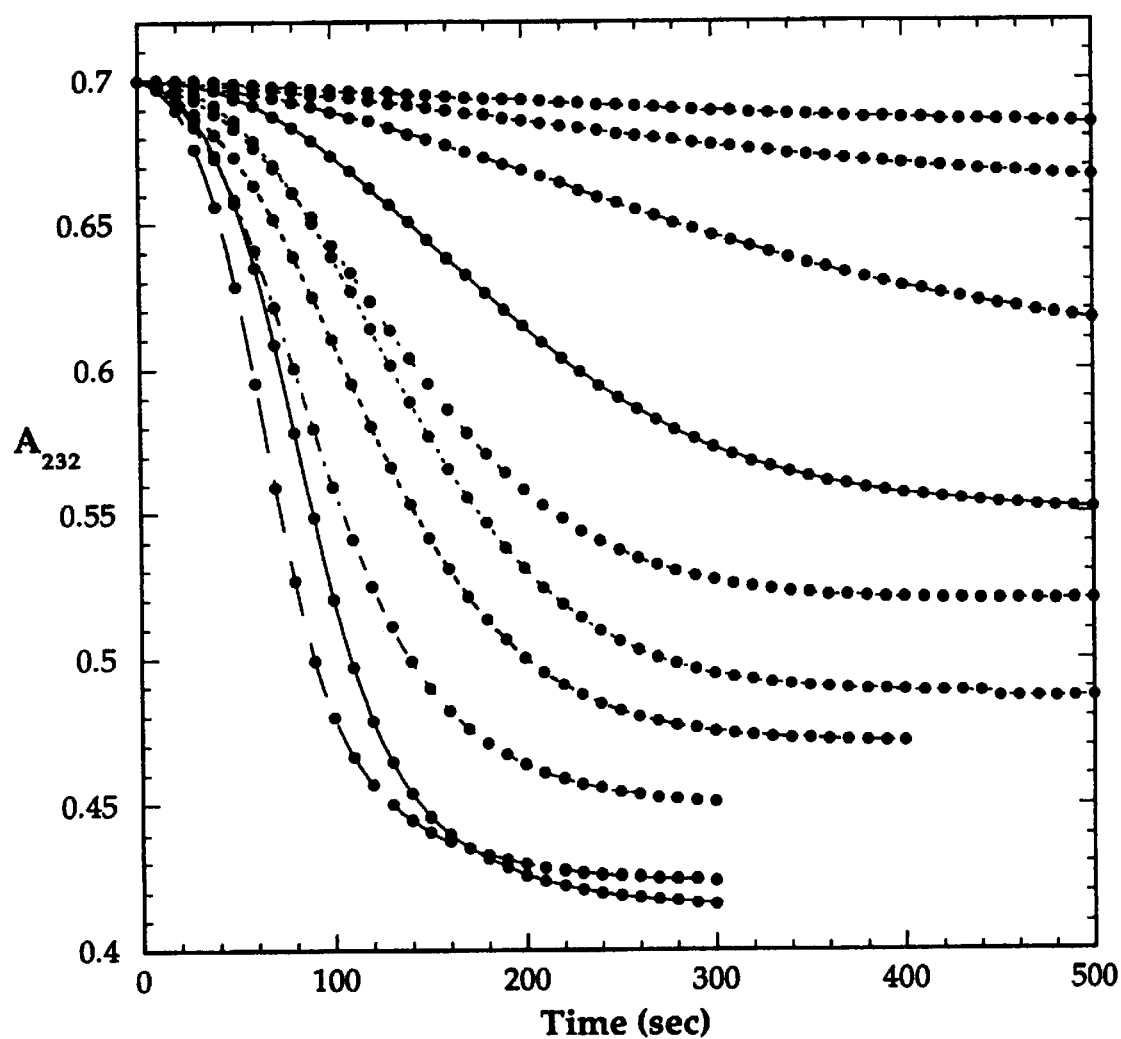
FIG. 15: Assays of the hydrolysis of HBCoA with varying amounts of PHA synthase. Assays were carried out in 40 μl assay volumes with the concentration of HBCoA remaining constant at 8 μM. Initial A$_{232}$ values, originally between 0.62 and 0.77, were normalized to 0.70. Enzyme amounts used in these assays were, from the upper-most curve, 0.38, 0.76, 1.14, 1.52, 1.90, 2.28, 2.66, 3.02, 3.42, 7.6, and 15.2 µg, respectively.

The effect of varying enzyme concentration in the presence of a fixed amount of substrate revealed an intriguing trend (FIG. 15). From these data it appears that the extent of polymerization is dependent on the amount of enzyme included in the reaction mixture. This could be explained if there is a "terminal length" limitation of the polymer, which, once reached, can not be extended any further. If this is the case, it would also suggest that termination of the polymerization reaction, the release of the synthase from the polymer, and/or reinitiation of polymerization by the newly released synthase are relatively slow events since no evidence of these reactions are seen within the timecourse of these studies. The phenomenon observed in FIG. 15 is not the result of decay of the enzyme over the course of the assay since virtually identical results are obtained following a 10 minute preincubation of the synthase at 25° C.

It must also be noted that comparisons of the direct spectrophotometric assays used here and the more common assay involving the use of Ellman's reagent, DTNB, (Ellman, supra) in the formation of thiolate of coenzyme-A showed that the values determined by the direct method were approximately 70% of the values determined using Ellman's reagent. This may be due to phase separation occurring in the cuvettes as the relatively insoluble polymer is formed. In support of this notion, a faint haze or opalescence in the cuvette developed during the course of the reaction, particularly at higher substrate concentrations.

PHA synthase purified from insect cells appears to be relatively stable. Examination of activity following storage, in liquid $N_2$ and at –20° C. in the presence of 50% glycerol showed that approximately 50% of synthase activity remained after 7 weeks when stored in liquid $N_2$ and approximately 75% of synthase activity remained after 7 weeks when stored at –20° C. in the presence of 50% glycerol.

The expression of PHA synthase from A. eutrophus in a baculovirus expression system results in the synthase constituting approximately 50% of total protein 60 hours post-infection; however, approximately 50–75% of the synthase is observed in the membrane-associated fraction. This elevated level of expression allowed purification of the soluble PHA synthase using a single chromatographic step on HA. The purity of this preparation is estimated to be approximately 90% (intact PHA synthase and 3 proteolysis products).

The initial specific activity of 12 U/mg was approximately 20-fold higher than the most successful previous efforts at overexpression of A. eutrophus PHA synthase. The synthase reported here was isolated from a 250 ml culture with 70% recovery which represents an improvement of 500-fold (1000 U/64 U×8 L/0.25 L) when compared to an 8 L E. coli culture with 40% recovery. This high expression level should provide sufficient PHA synthase for extensive structural, functional, and mechanistic studies. Furthermore, it is clear that the baculovirus expression system is an attractive option for isolation of other PHA synthases from various sources.

PHA synthase produced in the baculovirus system was of sufficient potency to allow direct spectrophotometric analysis of the hydrolysis of the thioester bond of HBCoA at 232 nm. These assays revealed a lag period of approximately 60 seconds, the length of which was variable and inversely related to enzyme concentration. Such a lag period presumably reflects a slow step in the reaction, perhaps correlating to dimerization of the enzyme, the priming, and/or initiation steps in formation of PHB. Size exclusion chromatographic examination of the PHB synthase native MW indicated two forms of the synthase. One form showed a MW of approximately 100–160 kDa and the other showed a MW of approximately 50–80 kDa; these two forms likely represent the dimer and monomer of PHA synthase, respectively. Similar results have been reported previously in which two forms of approximately 60 and 130 kDa were observed. Comparisons of the direct assay reported here and the indirect assay using DTNB revealed that the former resulted in values that were 70% of the values determined by the DTNB indirect assay. Although the reason for this difference has not been examined in detail, it is probable that the apparent phase separation that occurred upon PHB formation in the short pathlength cuvettes used, particularly with high [HBCoA], results in this discrepancy.

Enzymatic analyses of the PHA synthase have found that the enzyme has a broad pH optimum centered at pH 8.5; however, the studies described herein have been performed at pH 7.2 to provide comparative values with the results of others. Moreover, the specific activity of this enzyme is dependent upon enzyme concentration which confirms and extends earlier results (Gerngross et al., supra).

In studies intended to examine the dependence of activity upon enzyme concentration, it became apparent that the extent of the polymerization reaction is dependent on the amount of enzyme included in the reaction mixture. Specifically, decreasing the amount of enzyme leads not only to decreased velocity of reaction but also to a decreased extent of condensation (FIG. 15). One possible explanation is that the enzyme is thermally labile; however, identical assays in which the enzyme is preincubated at 25° C. for 10 minutes prior to initiation of the reaction had similar results. Another possibility is that a terminal-length of the polymer is reached precluding further condensations until the particular synthase molecule is released from the terminal-length polymer.

This work clearly demonstrates the value of the baculovirus expression system for the production of A. eutrophus PHA synthase and for the potential application to studies of other PHA synthases. Furthermore, the high level of expression obtained using the baculoviral system should allow convenient analysis for substrate-specificity and structure-function studies of PHA synthases from relatively crude insect cell extracts.

EXAMPLE 2

Co-expression of rat FAS dehydrase mutant cDNA and PHB synthase gene in insect cells.

Expression of a rat FAS DH- cDNA in Sf9 cells has been reported previously (Rangan et al., *J. Biol. Chem.*, 266, 19180 (1991); Joshi et al., *Biochem. J.*, 296, 143 (1993)). Once activity of the phbC gene product had been established in insect cells (see Example 1), baculovirus clones containing the rat FAS DH-cDNA and BacPAK6::phbC were employed in a double infection strategy to determine if PHB would be produced in insect cells. It was not known if an intracellular pool of R(-)-3-hydroxybutyrate would be stable or available as a substrate for the PHB synthase. In order for the R-(-)-3-hydroxybutyrylCoA to be available as a substrate, the R-(-)-3-hydroxybutyrylCoA released from rat FAS DH- protein must be trapped by the PHB synthase and incorporated into a polymer at a rate faster than β-oxidation, which would regenerate acetylCoA. It was also not known if the stereochemical configuration of the 3-hydroxyl group, which must be in the R form, would be recognized as a substrate by PHB synthase. Fortunately, previous biochemical studies on eukaryotic FASs indicated that the R form of 3-hydroxylbutyrylCoA would be generated (Wakil et al., *J. Biol. Chem.*, 237, 687 (1962)).

SDS-PAGE of protein samples from a time course of uninfected, single-infected, and dual-infected Sf21 cells was performed (FIG. 16). From these data, it is clear that the rat FAS DH mutant and PHB synthase polypeptides are efficiently co-expressed in Sf21 cells. However, co-expression results in ~50% reduced levels of both polypeptides compared to Sf21 cells that are producing the individual proteins. Western analysis using anti-rat FAS (Rangan et al., supra) and anti-PHA synthase antibodies confirmed simultaneous production of the corresponding proteins.

To provide further evidence that PHB was being synthesized in insect cells, T. ni cells which had been infected with a baculovirus vector encoding rat FAS DHO and/or a baculovirus vector encoding PHA synthase were analyzed for the presence of granules. Infected cells were fixed in paraformaldehyde and incubated with anti-PHA synthase antibodies (Williams et al., *Protein Exp. Purif.*, 7, 203 (1996)). Granules were observed only in doubly infected cells (Williams et al., *App. Environ. Micro.*, 62, 2540 (1996)).

Characterization of PHB production in insect cells. In order to determine if de novo synthesis of PHB was occurring in Sf21 cells that co-express the rat FAS DH mutant and PHB synthase, fractions of these samples were extracted, the extract subjected to propanolysis, and analyzed for the presence of propylhydroxybutyrate by gas chromatography (FIG. 17). A unique peak with a retention time that coincided with a propylhydroxybutyrate standard was detected only in the double infection samples at 48 and 72 hours, in contrast to the individually expressed gene products and uninfected controls, which were negative. These samples were analyzed further by GC/MS to confirm the identity of the product. FIG. 18 shows mass spectroscopy data corresponding to the material obtained from peak 10.1 in the gas chromatograph compared to an propylhydroxybutyrate standard. The results show that PHB synthesis is occurring only in Sf21 cells co-expressing the rat FAS DH mutant cDNA and the phbC gene from A. eutrophus. Integration of the peak in the gas chromatograph corresponding to propylhydroxybutyrate revealed that approximately 1 mg of PHB was isolated from 1 liter culture of Sf21 cells (approximately 600 mg dry cell weight of Sf21 cells). Thus, the ratFAS206 protein effectively replaces the β-ketothiolase and acetoacetyl-CoA reductase functions, resulting in the production of PHB by a novel pathway.

The approach described here provides a new strategy to combine metabolic pathways that are normally engaged in primary anabolic functions for production of polyesters. The premature termination of the normal fatty acid biosynthetic pathway to provide suitably modified acylCoA monomers for use in PHA synthesis can be applied to both prokaryotic and eukaryotic expression since the formation of polymer will not be dependent on specialized feedstocks. Thus, once a recombinant PHA monomer synthase is introduced into a prokaryotic or eukaryotic system, and co-expressed with the appropriate PHA synthase, novel biopolymer formation can occur.

EXAMPLE 3

Cloning and Sequencing of the vep ORFI PKS Gene Cluster

The entire PKS cluster from *Streptomyces venezuelae* was cloned using a heterologous hybridization strategy. A 1.2 kb DNA fragment that hybridized strongly to a DNA encoding an eryA PKS β-ketoacyl synthase domain was cloned and used to generate a plasmid for gene disruption. This method generated a mutant strain blocked in the synthesis of the antibiotic. A *S. venezuelae* genomic DNA library was generated. and used to clone a cosmid containing the complete methymycin aglycone PKS DNA. Fine-mapping analysis was performed to identify the order and sequence of catalytic domains along the multifunctional PKS (FIG. 19). DNA sequence analysis of the vep ORFI showed that the order of catalytic domains is KSQ/AT/ACP/KS/AT/KR/ACP/KS/AT/DH/KR/ACP. The complete DNA sequence, and corresponding amino acid sequence, of the vep ORFI is shown in FIG. 23 (SEQ ID NO:1 and SEQ ID NO:2, respectively).

The sequence data indicated that the PKS gene cluster encodes a polyene of twelve carbons. The vep gene cluster contains 5 polyketide synthase modules, with a loading module at its 5' end and an ending domain at its 3' end. Each of the sequenced modules includes a keto-ACP (KS), an acyltransferase (AT), a dehydratase (DH), a keto-reductase (KR), and an acyl carrier protein domain. The six acyltransferase domains in the cluster are responsible for the incorporation of six acetyl-CoA moieties into the product. The loading module contains a KSQ, an AT and an ACP domain. KSQ refers to a domain that is homologous to a KS domain except that the active site cysteine (C) is replaced by glutamine (Q). There is no counterpart to the KSQ domain in the PKS clusters which have been previously characterized.

The ending domain (ED) is an enzyme which is responsible for the attachment of the nascent polyketide chain onto another molecule. The amino acid sequence of ED resembles an enzyme, HetM, which is involved in Anabaena heterocyst formation. The homology between vep and HetM suggests that the polypeptide encoded by the vep gene cluster may synthesize a polyene-containing composition which is present in the spore coat or cell wall of its natural host, S. venezuelae.

EXAMPLE 4

To provide a recombinant monomer synthase that generates a saturated β-hydroxyhexanoylCoA or unsaturated β-hydroxyhexanoylCoA monomer, the linear correspondence between the genetic organization of the Type I macrolide PKS and the catalytic domain organization in the multifunctional proteins is assessed (Donadio et al., supra, 1991; Katz et al., Ann. Rev. Microbiol., 47, 875 (1993)). First, a DNA encoding a TE is added to the 3' end of an ORFI of a Type I PKS, preferably the met ORF I (FIG. 6) as recently described by Cortes et al. (Science, 268, 1487 (1995) in the erythromycin system. To ensure that the DNA encoding the TE is completely active, DNA encoding a linker region separating a normal ACP-TE region in a PKS, for example the one found in met PKS ORF5 (FIG. 5), will be incorporated into the DNA. The resulting vector can be introduced into a host cell and the TE activity, rate of release of the CoA product, and identity of the fatty acid chain determined.

The acyl chain that is most likely to be released is the CoA ester, specifically the 3-hydroxy-4-methyl heptenoylCoA ester, since the fully elongated chain is presumably released in this form prior to macrolide cyclization. If the CoA form of the acyl chain is not observed, then a gene encoding a CoA ligase will be cloned and co-expressed in the host cell to catalyze formation of the desired intermediate.

There is clear precedent for release of the predicted premature termination products from mutant strains of macrolide-producing Streptomyces that produce intermediates in macrolide synthesis (Huber et al., Antimicrob. Agents Chemother., 34, 1535 (1990); Kinoshita et al., J. Chem. Soc. Chem. Comm., 14, 943 (1988)). The structure of these intermediates is consistent with the linear organization of functional domains in macrolide PKSs, particularly those related to eryA, tyl, and met. Other known PKS gene clusters include, but are not limited to, the gene cluster encoding 6-methysalicylic acid synthase (Beck et al., Eur. J. Biochem., 192, 487 (1990)), soraphen A (Schupp et al., J. Bacteriol., 177, 3673 (1995), and sterigmatocystin (Yu et al., J. Bacteriol., 177, 4792 (1995)).

Figure 1:
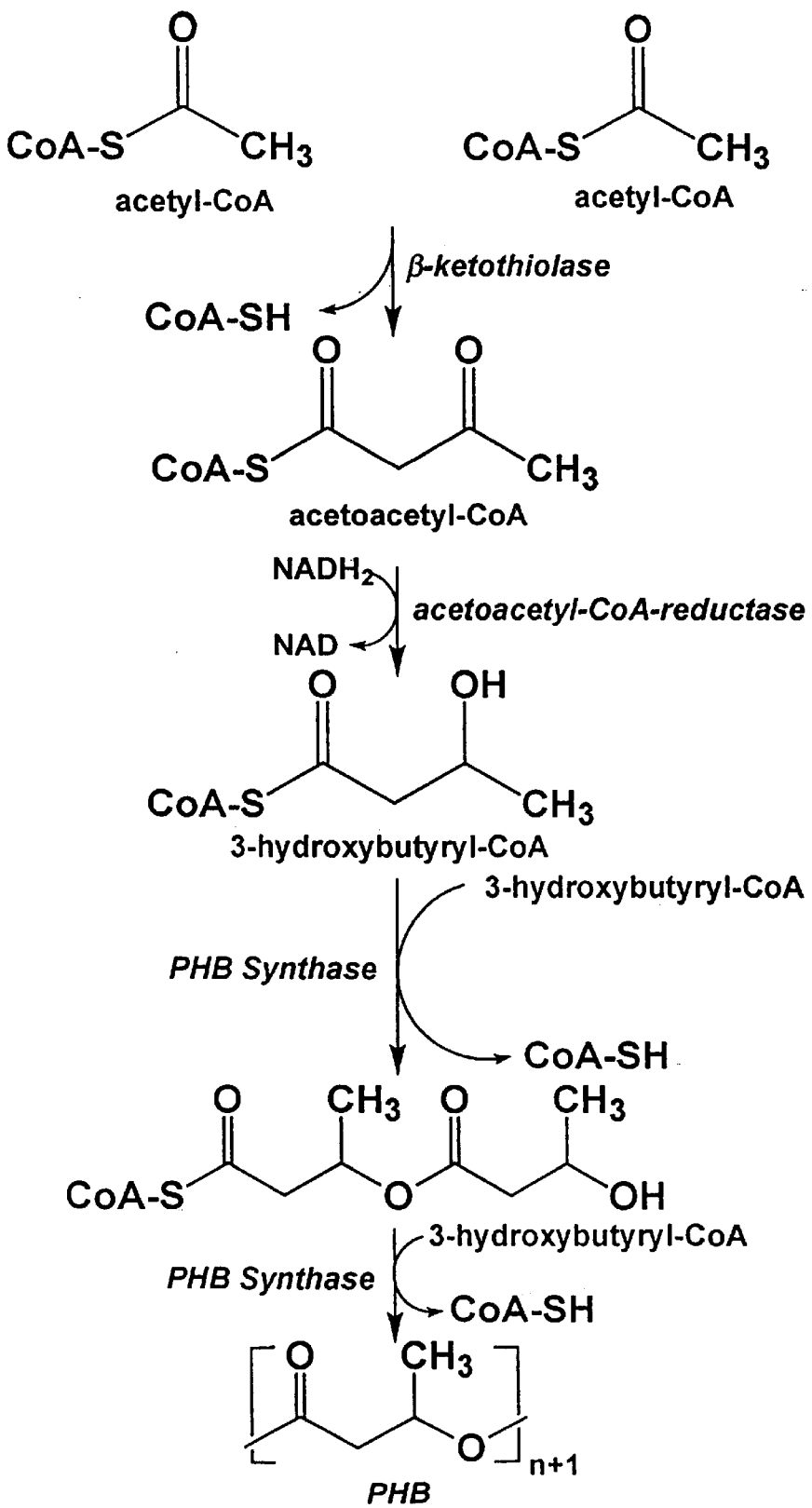
FIG. 1: The PHB biosynthetic pathway in A. eutrophus.
Figure 3:
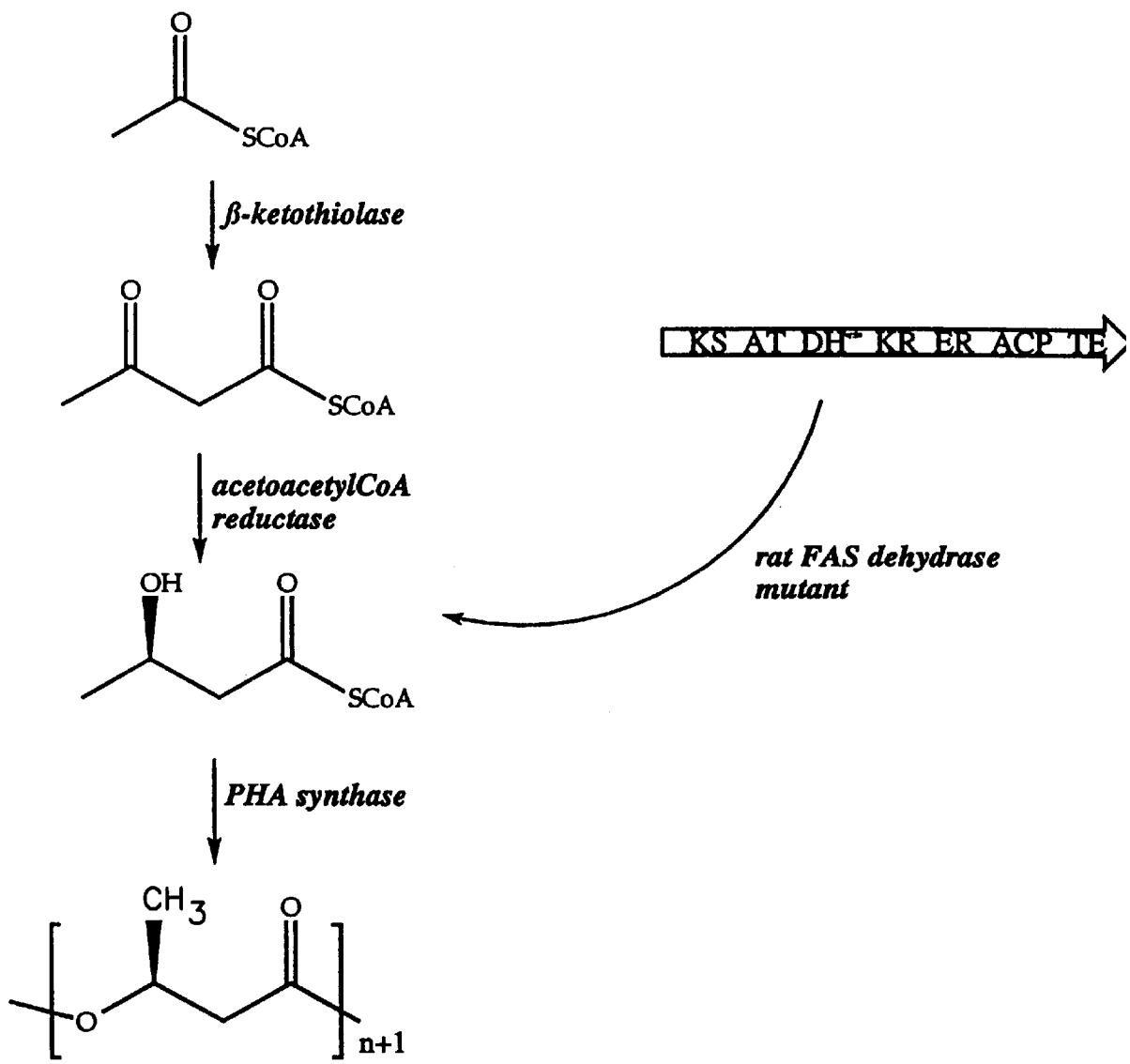
FIG. 3: Comparison of the natural and recombinant pathways for PHB synthesis. The three enzymatic steps of PHB synthesis in bacteria involving 3-ketothiolase, acetoacetyl-CoA reductase, and PHB synthase are shown on the left. The two enzymatic steps involved in PHB synthesis in the pathway in Sf21 cells containing a rat fatty acid synthase with an inactivated dehydrase domain (ratFAS206) are shown on the right.
Figure 4:
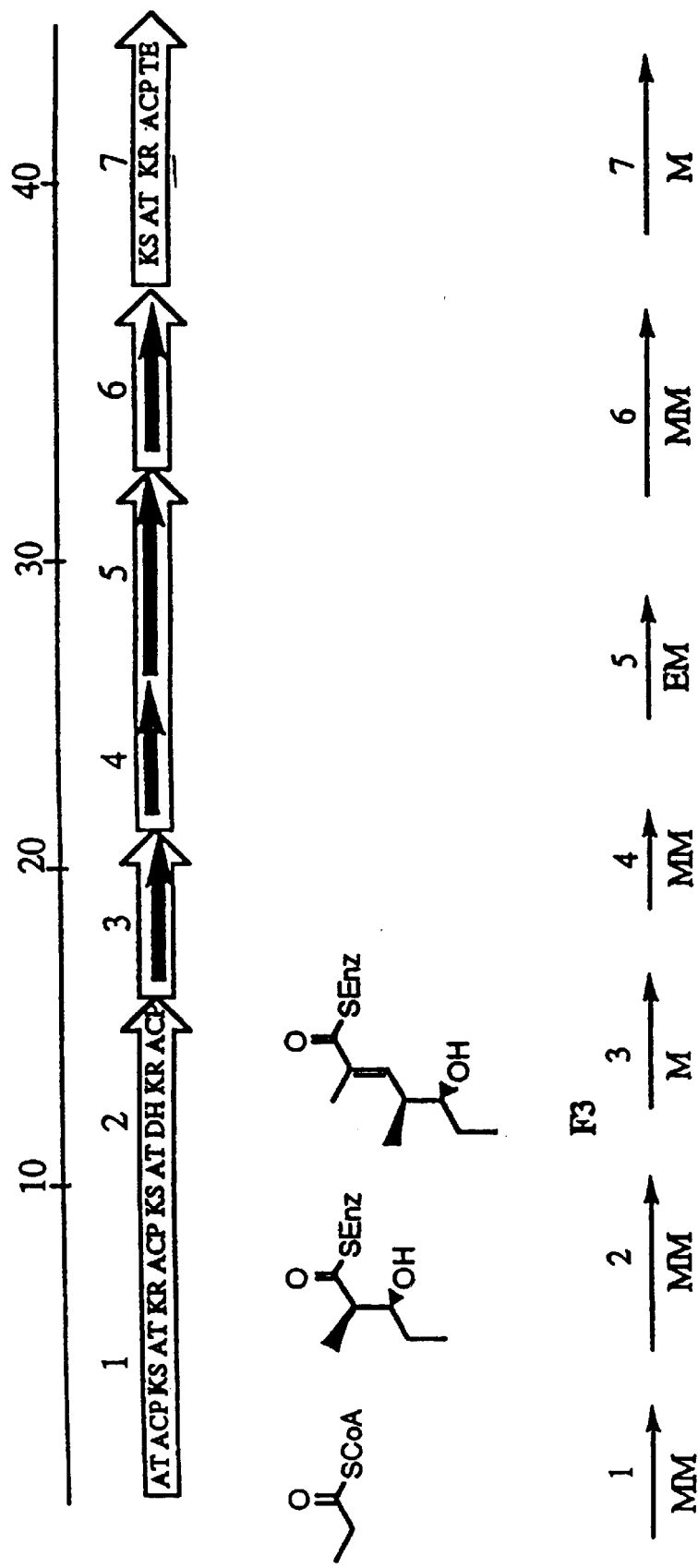
FIG. 4: Schematic diagram of the molecular organization of the tyl polyketide synthase (PKS) gene cluster. Open arrows correspond to individual open reading frames (ORFs) and numbers above an ORF denote a multifunctional module or synthase unit (SU). AT=acyltransferase; ACP=acyl carrier protein; KS=β-ketoacyl synthase; KR=ketoreductase; DH=dehydrase; ER=enoyl reductase; TE=thioesterase; MM=methylmalonylCoA; M=malonyl CoA; EM=ethylmalonyl CoA. Module 7 in tyl is also known as Module F.
Figure 5:
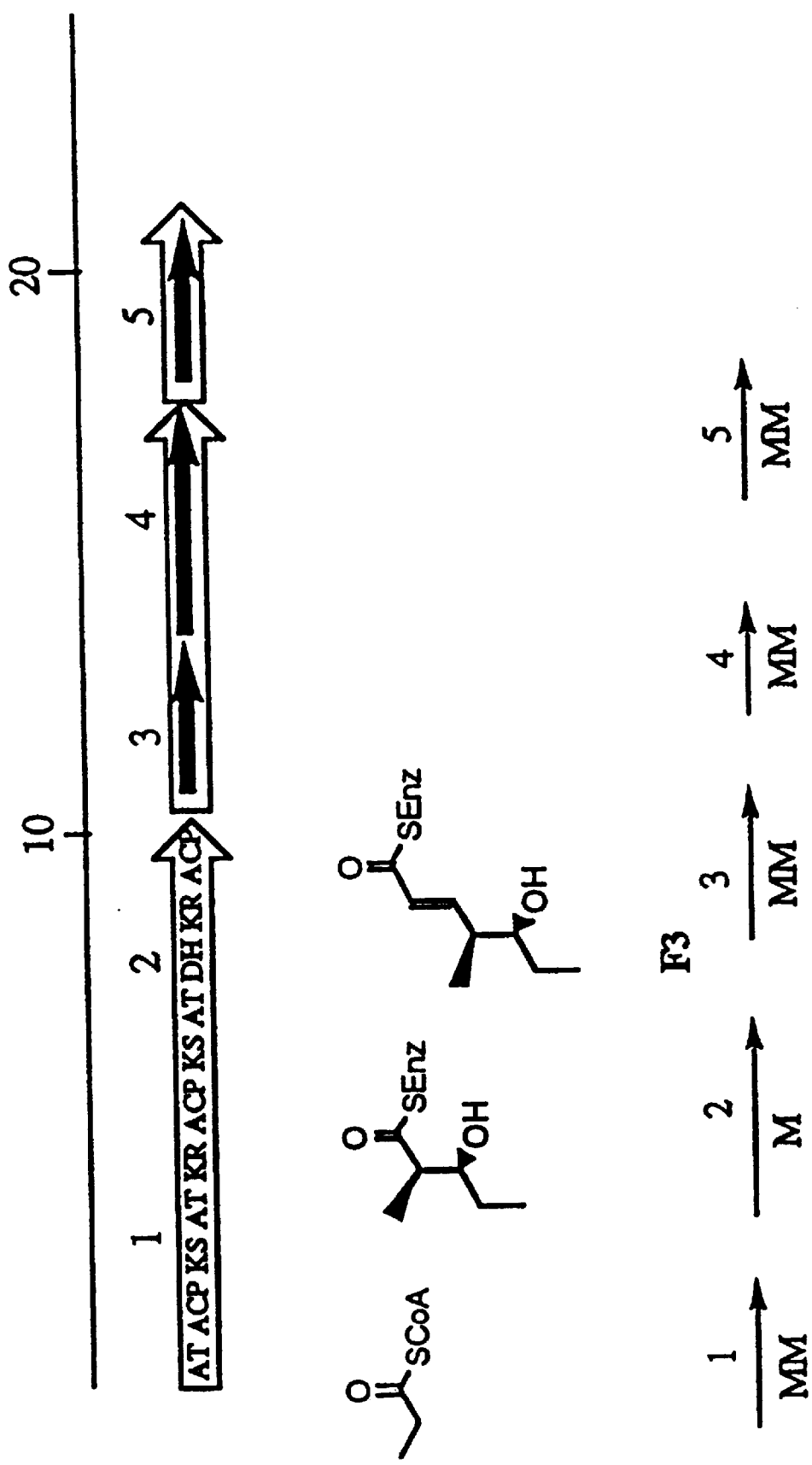
FIG. 5: Schematic diagram of the molecular organization of the met PKS gene cluster.

Once the release of the 3-hydroxy-4-methyl heptenoyl-CoA ester is established, DNA encoding the extender unit AT in met module 1 is replaced to change the specificity from methylmalonylCoA to malonylCoA (FIGS. 4–6). This change eliminates methyl group branching in the β-hydroxy acyl chain. While comparison of known AT amino acid sequences shows high overall amino acid sequence conservation, distinct regions are readily apparent where significant deletions or insertions have occurred. For example, comparison of malonyl and methylmalonyl amino acid sequences reveals a 37 amino acid deletion in the central region of the malonyltransferase. Thus, to change the specificity of the methylmalonyl transferase to malonyl transferase, the met ORFI DNA encoding the 37 amino acid sequence of MMT will be deleted, and the resulting gene will be tested in a host cell for production of the desmethyl species, 3-hydroxyheptenoylCoA. Alternatively, the DNA encoding the entire MMT can be replaced with a DNA encoding an intact MT to affect the desired chain construction.

After replacing MMT with MT, DNA encoding DH/ER will be introduced into DNA encoding met ORFI module 1. This modification results in a multifunctional protein that generates a methylene group at C-3 of the acyl chain (FIG. 6). The DNA encoding DH/ER will be PCR amplified from the available eryA or tyl PKS sequences, including the DNA encoding the required linker regions, employing a primer pair to conserved sequences 5' and 3' of the DNA encoding DH/ER. The PCR fragment will then be cloned into the met ORFI. The result is a DNA encoding a multifunctional protein (MT*DH/ER*TE*). This protein possesses the full complement of keto group processing steps and results in the production of heptenoylCoA.

The DNA encoding dehydrase in met module 2 is then inactivated, using site-directed mutagenesis in a scheme similar to that used to generate the rat FAS DH- described above (Joshi et al., J. Biol. Chem., 268, 22508 (1993)). This preserves the required (R)-3-hydroxy group which serves as the substrate for PHA synthases and results in a (R)-3-hydroxyheptanoylCoA species.

The final domain replacement will involve the DNA encoding the starter unit acyltransferase in met module 1 (FIG. 5), to change the specificity from propionyl CoA to acetyl CoA. This shortens the (R)-3-hydroxy acyl chain from heptanoyl to hexanoyl. The DNA encoding the catalytic domain will need to be generated based on a FAS or 6-methylsalicylic acid synthase model (Beck et al., Eur. J. Biochem., 192, 487 (1990)) or by using site-directed mutagenesis to alter the specificity of the resident met PKS propionyltransferase sequence. Limiting the initiator species to acetylCoA can result in the use of this starter unit by the monomer synthase. Previous work with macrolide synthases have shown that some are able to accept a wide range of starter unit carboxylic acids. This is particularly well documented for avermectin synthase, where over 60 new compounds have been produced by altering the starter unit substrate in precursor feeding studies (Dutton et al., J. Antibiotics, 44, 357 (1991)).

EXAMPLE 5

To provide a recombinant monomer synthase that synthesizes 3-hydroxyl-4-hexenoic acid, a precursor for polyhydoxyhexenoate, the DNA segment encoding the loading and the first module of the vep gene cluster was linked to the DNA segment encoding module 7 of the tyl gene cluster so as to yield a recombinant DNA molecule encoding a fusion polypeptide which has no amino acid diffences relative to the corresponding amino acid sequence of the parent modules. The fusion polypeptide catalyzes the synthesis of 3-hydroxyl-4-hexenoic acid. The recombinant DNA molecule was introduced into SCP2, a Streptomyces vector, under the control of the act promoter (pDHS502, FIG. 20). A polyhydroxyalkanoate polymerase gene, phaC1 from *Pseudomonas oleavorans,* was then introduced downstream of the recombinant PKS cluster (pDHS505; FIGS. 22 and 23). The DNA segment encoding the polyhydroxyalkanoate polymerase is linked to the DNA segment encoding the recombinant PKS synthase so as to yield a fusion polypeptide which synthesizes polyhydroxyhexenoate in Streptomyces. Polyhydroxyhexenoate, a biodegradable thermoplastic, is not naturally synthesized in Streptomyces, or as a major product in any other organism. Moreover, the unsaturated double bond in the side chain of polyhydroxyhexenoate may result in a polymer which has superior physical properties as a biodegradable thermoplastic over the known polyhydroxyalkanoates.

The complete disclosure of all patents, patent documents and publications cited herein are incorporated herein by reference as if individually incorporated. The foregoing detailed description and examples have been given for clarity of understanding only. No unnecessary limitations are to be understood therefrom. The invention is not limited to the exact details shown and described for variations obvious to one skilled in the art will be included within the invention defined by the claims.

What is claimed is:

1. An expression cassette comprising a nucleic acid molecule encoding a polyhydroxyalkanoate monomer synthase operably linked to a promoter functional in a host cell, wherein the nucleic acid molecule comprises a first DNA segment encoding a first module and a second DNA segment encoding a second module, wherein the first and second modules each comprise a ketoacyl synthase, an acyl transferase, a ketoreductase, and an acyl carrier protein, wherein the first module comprises a loading module at the N-terminus, wherein the second module comprises a thioesterase at the C-terminus, wherein the DNA segments together encode a recombinant polyhydroxyalkanoate monomer synthase, wherein the loading module contains at least one domain which binds a substrate of the polyhydroxyalkanoate monomer synthase, and wherein at least one DNA segment is from *Streptomyces venezuelae*.

2. A method of providing a polyhydroxyalkanoate polymer, comprising:
   (a) providing a eukaryotic cell comprising (i) a first expression cassette comprising a DNA segment encoding a fatty acid synthase operably linked to a promoter functional in the eukaryotic cell, wherein the fatty acid synthase comprises a ketoacyl synthase, an acyl transferase, an inactivated dehydrase, an enoyl reductase, a ketoreductase, an acyl carrier protein, and a thioesterase, (ii) a second expression cassette comprising a DNA segment encoding a polyhydroxyalkanoate synthase operably linked to a promoter functional in the eukaryotic cell, and (iii) a substrate for the fatty acid synthase, wherein the fatty acid synthase catalyzes the synthesis of a product from the substrate, wherein the product is a monomer substrate for the polyhydroxyalkanoate synthase; and
   (b) expressing the DNA segments in the cell so as to yield a fatty acid synthase which catalyzes the synthesis of the product and a polyhydroxyalkanoate synthase which catalyzes the synthesis of a polyhydroxyalkanoate polymer comprising the product.

3. The method of claim 2 wherein the dehydrase activity of the fatty acid synthase is inactivated by mutating the DNA segment of (a)(i) to encode an amino acid substitution at the active site of the dehydrase, wherein the active site corresponds to the histidine at position 878 in rat fatty acid synthase.

4. An isolated and purified DNA molecule comprising a first DNA segment encoding a first module and a second DNA segment encoding a second module, wherein the first and second modules each comprise a ketoacyl synthase, an acyl transferase, a ketoreductase, and an acyl carrier protein, wherein the first module comprises a loading module at the N-terminus, wherein the second module comprises a thioesterase at the C-terminus, wherein the DNA segments together encode a recombinant polyhydroxyalkanoate monomer synthase, wherein the loading module contains at least one domain which binds a substrate of the polyhydroxyalkanoate monomer synthase, and wherein at least one DNA segment is from *Streptomyces venezuelae*.

5. The isolated DNA molecule of claim 4 wherein the second DNA segment comprises a linker region located between the DNA encoding the acyl carrier protein and the DNA encoding the thioesterase.

6. The isolated DNA molecule of claim 4 wherein the first DNA segment comprises DNA encoding two acyl transferases, wherein the first acyl transferase is in the loading module.

7. The isolated DNA molecule of claim 6 wherein the second acyl transferase adds acyl groups to malonylCoA.

8. The isolated DNA molecule of claim 4 wherein the first DNA segment further comprises a DNA encoding a dehydrase or a DNA encoding a dehydrase and an enoyl reductase.

9. The isolated DNA molecule of claim 4 wherein the second DNA segment further comprises a DNA encoding an inactive dehydrase.

10. The isolated DNA molecule of claim 4 wherein the first DNA segment comprises a DNA encoding an acetyl, malonyl or methylmalonyl transferase.

11. The isolated DNA molecule of claim 6 wherein the acyl transferase in the loading module binds an acyl CoA substrate.

12. A method of providing a polyhydroxyalkanoate monomer, comprising:
  (a) providing a host cell comprising i) a DNA molecule comprising a promoter functional in the cell operably linked to a DNA sequence encoding a recombinant polyhydroxyalkanoate monomer synthase, wherein the DNA sequence comprises a first DNA segment encoding a first module and a second DNA segment encoding a second module, wherein the first and second modules each comprise a ketoacyl synthase, an acyl transferase, a ketoreductase, and an acyl carrier protein, wherein the first module comprises a loading module at the N-terminus, wherein the second module comprises a thioesterase at the C-terminus, and wherein the loading module contains at least one domain which binds a substrate of the polyhydroxyalkanoate monomer synthase, and ii) a substrate for the loading module-of the recombinant polyhydroxyalkanoate monomer synthase, wherein recombinant polyhydroxyalkanoate monomer synthase catalyzes the synthesis of a polyhydroxyalkanoate monomer from the substrate; and
  (b) expressing the DNA molecule in the host cell so as to yield recombinant polyhydroxyalkanoate monomer synthase which catalyzes the synthesis of the polyhydroxyalkanoate monomer.

13. A method of providing a polyhydroxyalkanoate polymer, comprising:
  (a) providing a host cell comprising i) a first DNA molecule comprising a promoter functional in the cell operably linked to a DNA sequence encoding a recombinant polyhydroxyalkanoate monomer synthase, wherein the DNA sequence comprises a first DNA segment encoding a first module and a second DNA segment encoding a second module, wherein the first and second modules each comprise a ketoacyl synthase, an acyl transferase, a ketoreductase, and an acyl carrier protein, wherein the first module comprises a loading module at the N-terminus, and wherein the second module comprises a thioesterase at the C-terminus, and wherein the loading module contains at least one domain which binds a substrate of the polyhydroxyalkanoate monomer synthase, ii) a second DNA molecule comprising a promoter functional in the host cell operably linked to a DNA segment encoding a polyhydroxyalkanoate synthase, and iii) a substrate for the loading module, wherein the recombinant polyhydroxyalkanoate monomer synthase catalyzes the synthesis of a polyhydroxyalkanoate monomer from the substrate, and wherein the polyhydroxyalkanoate monomer is a substrate for the polyhydroxyalkanoate synthase; and
  (b) expressing the DNA molecule in the host cell so as to yield recombinant polyhydroxyalkanoate monomer synthase which catalyzes the synthesis of the polyhydroxyalkanoate monomer and the polyhydroxyalkanoate synthase catalyzes the synthesis of the polyhydroxyalkanoate polymer comprising the polyhydroxyalkanoate monomer.

14. The method of claim 12 wherein the first DNA segment encodes the first module from the vep gene cluster and the second DNA segment encodes module 7 from the tyl P gene cluster.

15. The method of claim 13 wherein the first DNA segment encodes the first module from the vep gene cluster and the second DNA segment encodes module 7 from the tyl P gene cluster.

16. An isolated and purified DNA molecule comprising a first DNA segment encoding a fatty acid synthase and a second DNA segment encoding a module of a polyketide synthase, wherein the fatty acid synthase comprises a ketoacyl synthase, an acyl transferase, a dehydrase, a ketoreductase, an enoyl reductase and an acyl carrier protein, wherein the polyketide synthase module comprises a ketoacyl synthase, an acyl transferase, a ketoreductase, and an acyl carrier protein, and wherein the DNA segments together encode a recombinant polyhydroxyalkanoate monomer synthase.

17. The isolated DNA molecule of claim 16 wherein the second DNA segment is 3' to the DNA encoding the fatty acid synthase.

18. A method of providing a polyhydroxyalkanoate monomer, comprising:
  (a) providing a host cell comprising i) a DNA molecule comprising a first DNA segment encoding a fatty acid synthase and a second DNA segment encoding a module of a polyketide synthase, wherein the first DNA segment is 5' to the second DNA segment, wherein the first DNA segment is operably linked to a promoter functional in the host cell, wherein the first DNA segment is linked to the second DNA segment so that the linked DNA segments express a fusion protein, wherein the fatty acid synthase comprises a ketoacyl synthase, an acyl transferase, a dehydrase, a ketoreductase, an enoyl reductase, and an acyl carrier protein, and wherein the polyketide synthase module comprises a ketoacyl synthase, an acyl transferase; a ketoreductase, and an acyl carrier protein, and ii) a substrate for the fatty acid synthase, wherein the fusion protein catalyzes the synthesis of a polyhydroxyalkanoate monomer from the substrate; and
  (b) expressing the DNA molecule in the host cell so as to yield the fusion protein which catalyzes the synthesis of the polyhydroxyalkanoate monomer.

19. The method of claim 18 wherein the DNA encoding the polyketide synthase module is from DNA encoding the tyl module F.

20. The expression cassette of claim 1 further comprising a third DNA segment encoding a polyhydroxyalkanoate synthase.

21. The method of claim 12 wherein the DNA molecule further comprises a DNA segment encoding a polyhydroxyalkanoate synthase.

22. The isolated DNA molecule of claim 4 further comprising a DNA segment encoding a polyhydroxyalkanoate synthase.

23. The expression cassette of claim 1 wherein at least one DNA segment encodes a met module.

24. The expression cassette of claim 1 wherein at least one of the modules is a module of SEQ ID NO:2 or a module of SEQ ID NO:4.

25. The expression cassette of claim 1 wherein at least one module is encoded by SEQ ID NO:3.

26. The isolated and purified DNA molecule of claim 4 wherein at least one DNA segment encodes a met module.

27. The isolated and purified DNA molecule of claim 4 wherein at least one of the modules is a module of SEQ ID NO:2 or a module of SEQ ID NO:4.

28. The isolated and purified DNA molecule of claim 4 wherein at least one module is encoded by SEQ ID NO:3.

29. The method of claim 12 or 13 wherein at least one module is encoded by Streptomyces DNA.

30. The method of claim 12 or 13 wherein at least one module is encoded by *Streptomyces venezulae* DNA.

31. The method of claim 12 or 13 wherein at least one module is a met module.

32. The method of claim 12 or 13 wherein at least one of the modules is a module of SEQ ID NO:2 or a module of SEQ ID NO:4.

33. The method of claim 12 or 13 wherein at least one module is encoded by SEQ ID NO:3.

34. The isolated and purified DNA molecule of claim 16 wherein the module of the polyketide synthase is encoded by Streptomyces DNA.

35. The isolated and purified DNA molecule of claim 16 wherein the module of the polyketide synthase is encoded by *Streptomyces venezuelae* DNA.

36. The isolated and purified DNA molecule of claim 1 wherein the module of the polyketide synthase is a met module.

37. The isolated and purified DNA molecule of claim 16 wherein the module of the polyketide synthase is a module of SEQ ID NO:2 or a module of SEQ ID NO:4.

38. The isolated and purified DNA molecule of claim 16 wherein the module of the polyketide synthase is encoded by SEQ ID NO:3.

39. The expression cassette of claim 1 wherein at least one DNA segment encodes a tyl module.

40. The isolated DNA of claim 4 wherein at least one DNA segment encodes a tyl module.

41. The method of claim 12 or 13 wherein at least one DNA segment encodes a tyl module.

42. The method of claim 18 wherein the module of the polyketide synthase is encoded by *Streptomyces venezuelae* DNA.

43. The method of claim 18 wherein the module of the polyketide synthase is a met module.

44. The method of claim 18 wherein the module of the polyketide synthase is a module of SEQ ID NO:2 or a module of SEQ ID NO:4.

* * * * *

SEQUENCE LISTING

```
<160> NUMBER OF SEQ ID NOS: 4

<210> SEQ ID NO 1
<211> LENGTH: 15872
<212> TYPE: DNA
<213> ORGANISM: Streptomyces venezuelae
<220> FEATURE:
<221> NAME/KEY: CDS
<222> LOCATION: (20)...(13909)

<400> SEQUENCE: 1
ttaattaagg aggaccatc atg aac gag gcc atc gcc gtc gtc ggc atg tcc        52
                    Met Asn Glu Ala Ile Ala Val Val Gly Met Ser
                     1               5                  10 tgc cgc ctg ccg aag gcc tcg aac ccg gcc gcc ttc tgg gag ctg ctg       100
Cys Arg Leu Pro Lys Ala Ser Asn Pro Ala Ala Phe Trp Glu Leu Leu
             15                  20                  25 cgg aac ggg gag agc gcc gtc acc gac gtg ccc tcc ggc cgg tgg acg       148
Arg Asn Gly Glu Ser Ala Val Thr Asp Val Pro Ser Gly Arg Trp Thr
         30                  35                  40 tcg gtg ctc ggg gga gcg gac gcc gag gag ccg gcg gag tcc ggt gtc       196
Ser Val Leu Gly Gly Ala Asp Ala Glu Glu Pro Ala Glu Ser Gly Val
     45                  50                  55 cgc cgg ggc ggc ttc ctc gac tcc ctc gac ctc ttc gac gcg gcc ttc       244
Arg Arg Gly Gly Phe Leu Asp Ser Leu Asp Leu Phe Asp Ala Ala Phe
 60                  65                  70                  75 ttc gga atc tcg ccc cgt gag gcc gcc gcc atg gac ccg cag cag cga       292
Phe Gly Ile Ser Pro Arg Glu Ala Ala Ala Met Asp Pro Gln Gln Arg
                 80                  85                  90 ctg gtc ctc gaa ctc gcc tgg gag gcg ctg gag gac gcc gga atc gtc       340
Leu Val Leu Glu Leu Ala Trp Glu Ala Leu Glu Asp Ala Gly Ile Val
             95                 100                 105 ccc ggc acc ctc gcc gga agc cgc acc gcc gtc ttc gtc ggc acc ctg       388
Pro Gly Thr Leu Ala Gly Ser Arg Thr Ala Val Phe Val Gly Thr Leu
        110                 115                 120 cgg gac gac tac acg agc ctc ctc tac cag cac ggc gag cag gcc atc       436
Arg Asp Asp Tyr Thr Ser Leu Leu Tyr Gln His Gly Glu Gln Ala Ile
    125                 130                 135 acc cag cac acc atg gcg ggc gtg aac cgg ggc gtc atc gcc aac cgc       484
Thr Gln His Thr Met Ala Gly Val Asn Arg Gly Val Ile Ala Asn Arg
140                 145                 150                 155 gtc tcg tac cac ctc ggc ctg cag ggc ccg agc ctc acc gtc gac gcc       532
Val Ser Tyr His Leu Gly Leu Gln Gly Pro Ser Leu Thr Val Asp Ala
```

-continued

```
              160                 165                 170
gcg cag tcg tcc tcg ctc gtc gcc gtg cac ctg gcc tgc gag tcc ctg       580
Ala Gln Ser Ser Ser Leu Val Ala Val His Leu Ala Cys Glu Ser Leu
        175                 180                 185 cgc gcc ggg gag tcc acg acg gcg ctc gtc gcc ggc gtg aac ctc aac       628
Arg Ala Gly Glu Ser Thr Thr Ala Leu Val Ala Gly Val Asn Leu Asn
        190                 195                 200 atc ctc gcg gag agc gcc gtg acg gag gag cgc ttc ggt gga ctc tcc       676
Ile Leu Ala Glu Ser Ala Val Thr Glu Glu Arg Phe Gly Gly Leu Ser
        205                 210                 215 ccg gac ggc acc gcc tac acc ttc gac gcg cgg gcc aac gga ttc gtc       724
Pro Asp Gly Thr Ala Tyr Thr Phe Asp Ala Arg Ala Asn Gly Phe Val
220                 225                 230                 235 cgg ggc gag ggc ggc gga gtc gtc gta ctc aag ccg ctc tcc cgc gcc       772
Arg Gly Glu Gly Gly Gly Val Val Val Leu Lys Pro Leu Ser Arg Ala
                240                 245                 250 ctc gcc gac ggc gac cgt gtc cac ggc gtc atc cgc gcc agc gcc gtc       820
Leu Ala Asp Gly Asp Arg Val His Gly Val Ile Arg Ala Ser Ala Val
                255                 260                 265 aac aac gac gga gcc acc ccg ggt ctc acc gtg ccc agc agg gcc gcc       868
Asn Asn Asp Gly Ala Thr Pro Gly Leu Thr Val Pro Ser Arg Ala Ala
                270                 275                 280 cag gag aag gtg ctg cgc gag gcg tac cgg aag gcg gcc ctg gac ccg       916
Gln Glu Lys Val Leu Arg Glu Ala Tyr Arg Lys Ala Ala Leu Asp Pro
285                 290                 295 tcc gcc gtc cag tac gtc gaa ctc cac ggc acc gga acc ccc gtc ggc       964
Ser Ala Val Gln Tyr Val Glu Leu His Gly Thr Gly Thr Pro Val Gly
300                 305                 310                 315 gac ccc atc gag gcc gcc gcg ctc ggc gcc gtc ctc ggc tcg gcg cgc      1012
Asp Pro Ile Glu Ala Ala Ala Leu Gly Ala Val Leu Gly Ser Ala Arg
                320                 325                 330 ccc gcg gac gaa ccc ctg ctc gtc ggc tcg gcc aag acg aac gtc ggg      1060
Pro Ala Asp Glu Pro Leu Leu Val Gly Ser Ala Lys Thr Asn Val Gly
                335                 340                 345 cac ctc gaa ggc gcc gcc ggc atc gtc ggc ctc atc aag acg ctc ctc      1108
His Leu Glu Gly Ala Ala Gly Ile Val Gly Leu Ile Lys Thr Leu Leu
                350                 355                 360 gcg ctc ggc cgg cgc cgg atc ccg gcg agc ctc aac ttc cgt acg ccc      1156
Ala Leu Gly Arg Arg Arg Ile Pro Ala Ser Leu Asn Phe Arg Thr Pro
        365                 370                 375 cac ccg gac atc ccg ctc gac acc ctc ggg ctc gac gtg ccc gac ggc      1204
His Pro Asp Ile Pro Leu Asp Thr Leu Gly Leu Asp Val Pro Asp Gly
380                 385                 390                 395 ctg cgg gag tgg ccg cac ccg gac cgc gaa ctc ctc gcc ggc gtc agc      1252
Leu Arg Glu Trp Pro His Pro Asp Arg Glu Leu Leu Ala Gly Val Ser
                400                 405                 410 tcg ttc ggc atg ggc ggc acc aac gcc cac gtc gtc ctc agc gaa ggc      1300
Ser Phe Gly Met Gly Gly Thr Asn Ala His Val Val Leu Ser Glu Gly
        415                 420                 425 ccc gcc cag ggc ggc gag cag ccc ggc atc gat gag gag acc ccc gtc      1348
Pro Ala Gln Gly Gly Glu Gln Pro Gly Ile Asp Glu Glu Thr Pro Val
        430                 435                 440 gac agc ggg gcc gca ctg ccc ttc gtc gtc acc ggc cgc ggc ggc gag      1396
Asp Ser Gly Ala Ala Leu Pro Phe Val Val Thr Gly Arg Gly Gly Glu
        445                 450                 455 gcc ctg cgc gcc cag gcc cgg cgc ctg cac gag gcc gtc gaa gcg gac      1444
Ala Leu Arg Ala Gln Ala Arg Arg Leu His Glu Ala Val Glu Ala Asp
460                 465                 470                 475 ccg gag ctc gcg ccc gcc gca ctc gcc cgg tcg ctg gtc acc acc cgt      1492
```

```
                                                              -continued

Pro Glu Leu Ala Pro Ala Ala Leu Ala Arg Ser Leu Val Thr Thr Arg
            480                 485                 490 acg gtc ttc acg cac cgg tcg gtc gtc ctc gcc ccg gac cgc gcc cgc       1540
Thr Val Phe Thr His Arg Ser Val Val Leu Ala Pro Asp Arg Ala Arg
            495                 500                 505 ctc ctc gac ggc ctc ggc gcc ctc gcc gcc ggg acg ccc gcg ccc ggc       1588
Leu Leu Asp Gly Leu Gly Ala Leu Ala Ala Gly Thr Pro Ala Pro Gly
            510                 515                 520 gtg gtc acc ggc acc ccc gcc ccc ggg cgc ctc gcc gtc ctg ttc agc       1636
Val Val Thr Gly Thr Pro Ala Pro Gly Arg Leu Ala Val Leu Phe Ser
        525                 530                 535 ggc cag ggt gcc caa cgt acg ggc atg ggc atg gag ttg tac gcc gcc       1684
Gly Gln Gly Ala Gln Arg Thr Gly Met Gly Met Glu Leu Tyr Ala Ala
540                 545                 550                 555 cac ccc gcc ttc gcg acg gcc ttc gac gcc gtc gcc gcc gaa ctg gac       1732
His Pro Ala Phe Ala Thr Ala Phe Asp Ala Val Ala Ala Glu Leu Asp
                560                 565                 570 ccc ctc ctc gac cgg ccc ctc gcc gaa ctc gtc gcg gcg ggc gac acc       1780
Pro Leu Leu Asp Arg Pro Leu Ala Glu Leu Val Ala Ala Gly Asp Thr
            575                 580                 585 ctc gac cgc acc gtc cac aca cag ccc gcg ctc ttc gcc gtg gag gtc       1828
Leu Asp Arg Thr Val His Thr Gln Pro Ala Leu Phe Ala Val Glu Val
        590                 595                 600 gcc ctc cac cgc ctc gtc gag tcc tgg ggc gtc acg ccc gac ctg ctc       1876
Ala Leu His Arg Leu Val Glu Ser Trp Gly Val Thr Pro Asp Leu Leu
    605                 610                 615 gcc ggc cac tcc gtc ggc gag atc agc gcc gcc cac gtc gcc ggg gtc       1924
Ala Gly His Ser Val Gly Glu Ile Ser Ala Ala His Val Ala Gly Val
620                 625                 630                 635 ctg tcg ctg cgc gac gcc gcc cgc ctc gtc gcg gcg cgc ggc cgc ctc       1972
Leu Ser Leu Arg Asp Ala Ala Arg Leu Val Ala Ala Arg Gly Arg Leu
                640                 645                 650 atg cag gcg ctc ccc gag ggc ggc gcg atg gtc gcg gtc gag gcg agc       2020
Met Gln Ala Leu Pro Glu Gly Gly Ala Met Val Ala Val Glu Ala Ser
            655                 660                 665 gag gag gaa gtg ctt ccg cac ctc gcg gga cgc gag cgg gag ctc tcc       2068
Glu Glu Glu Val Leu Pro His Leu Ala Gly Arg Glu Arg Glu Leu Ser
        670                 675                 680 ctc gcg gcc gtg aac ggc ccc cgc gcg gtc gtc ctc gcg ggc gcc gag       2116
Leu Ala Ala Val Asn Gly Pro Arg Ala Val Val Leu Ala Gly Ala Glu
    685                 690                 695 cgc gcc gtc ctc gac gtc gcc gag ctg ctg cgc gaa cag ggc cgc cgg       2164
Arg Ala Val Leu Asp Val Ala Glu Leu Leu Arg Glu Gln Gly Arg Arg
700                 705                 710                 715 acg aag cgg ctc agc gtc tcg cac gcc ttc cac tcg ccg ctc atg gag       2212
Thr Lys Arg Leu Ser Val Ser His Ala Phe His Ser Pro Leu Met Glu
                720                 725                 730 ccg atg ctc gac gac ttc cgc cgg gtc gtc gaa gag ctg gac ttc cag       2260
Pro Met Leu Asp Asp Phe Arg Arg Val Val Glu Glu Leu Asp Phe Gln
            735                 740                 745 gag ccc cgc gtc gac gtc gtg tcc acg gtg acg ggc ctg cct gtc aca       2308
Glu Pro Arg Val Asp Val Val Ser Thr Val Thr Gly Leu Pro Val Thr
        750                 755                 760 gcg ggc caa tgg acc gat ccc gag tac tgg gtg gac cag gtc cgc agg       2356
Ala Gly Gln Trp Thr Asp Pro Glu Tyr Trp Val Asp Gln Val Arg Arg
    765                 770                 775 ccc gta cgc ttc ctc gac gcc gta cgc acc ctg gag gaa tcg ggc gcc       2404
Pro Val Arg Phe Leu Asp Ala Val Arg Thr Leu Glu Glu Ser Gly Ala
780                 785                 790                 795
```

-continued

| | |
|---|---|
| gac acc ttc ctg gag ctc ggt ccc gac ggg gtc tgc tcc gcg atg gcg<br>Asp Thr Phe Leu Glu Leu Gly Pro Asp Gly Val Cys Ser Ala Met Ala<br>800       805       810 | 2452 |
| gcg gac tcc gta cgc gac cag gag gcc gcc acg gcg gtc tcc gcc ctg<br>Ala Asp Ser Val Arg Asp Gln Glu Ala Ala Thr Ala Val Ser Ala Leu<br>815       820       825 | 2500 |
| cgc aag ggc cgc ccg gag ccc cag tcg ctc ctc gcc gca ctc acc acc<br>Arg Lys Gly Arg Pro Glu Pro Gln Ser Leu Leu Ala Ala Leu Thr Thr<br>830       835       840 | 2548 |
| gtc ttc gtc cgg ggc cac gac gtc gac tgg acc gcc gcg cac ggg agc<br>Val Phe Val Arg Gly His Asp Val Asp Trp Thr Ala Ala His Gly Ser<br>845       850       855 | 2596 |
| acc ggc acg gtc agg gtg ccc ctg ccg acc tac gcc ttc cag cgc gaa<br>Thr Gly Thr Val Arg Val Pro Leu Pro Thr Tyr Ala Phe Gln Arg Glu<br>860       865       870       875 | 2644 |
| cgc cac tgg ttc gac ggc gcc gcg cga acg gcg gcg ccg ctc acg gcg<br>Arg His Trp Phe Asp Gly Ala Ala Arg Thr Ala Ala Pro Leu Thr Ala<br>880       885       890 | 2692 |
| ggc cga tcg ggc acc ggt gcg ggc acc ggc ccg gcc gcg ggt gtg acg<br>Gly Arg Ser Gly Thr Gly Ala Gly Thr Gly Pro Ala Ala Gly Val Thr<br>895       900       905 | 2740 |
| tcg ggc gag ggc gag ggc gag ggc gag ggc gcg ggt gcg ggt ggc ggt<br>Ser Gly Glu Gly Glu Gly Glu Gly Glu Gly Ala Gly Ala Gly Gly Gly<br>910       915       920 | 2788 |
| gat cgg ccg gct cgc cac gag acg acc gag cgc gtg cgc gca cac gtc<br>Asp Arg Pro Ala Arg His Glu Thr Thr Glu Arg Val Arg Ala His Val<br>925       930       935 | 2836 |
| gcc gcc gtc ctc gag tac gac gac ccg acc cgc gtc gaa ctc ggc ctc<br>Ala Ala Val Leu Glu Tyr Asp Asp Pro Thr Arg Val Glu Leu Gly Leu<br>940       945       950       955 | 2884 |
| acc ttc aag gag ctg ggc ttc gac tcc ctc atg tcc gtc gag ctg cgg<br>Thr Phe Lys Glu Leu Gly Phe Asp Ser Leu Met Ser Val Glu Leu Arg<br>960       965       970 | 2932 |
| aac gcg ctc gtc gac gac acg gga ctg cgc ctg ccc agc gga ctg ctc<br>Asn Ala Leu Val Asp Asp Thr Gly Leu Arg Leu Pro Ser Gly Leu Leu<br>975       980       985 | 2980 |
| ttc gac cac ccg acg ccg cgc gcc ctc gcc gcc cac ctg ggc gac ctg<br>Phe Asp His Pro Thr Pro Arg Ala Leu Ala Ala His Leu Gly Asp Leu<br>990       995       1000 | 3028 |
| ctc acc ggc ggc agc ggc gag acc gga tcg gcc gac ggg ata ccg ccc<br>Leu Thr Gly Gly Ser Gly Glu Thr Gly Ser Ala Asp Gly Ile Pro Pro<br>1005       1010       1015 | 3076 |
| gcg acc ccg gcg gac acc acc gcc gag ccc atc gcg atc atc ggc atg<br>Ala Thr Pro Ala Asp Thr Thr Ala Glu Pro Ile Ala Ile Ile Gly Met<br>1020       1025       1030       1035 | 3124 |
| gcc tgc cgc tac ccc ggc ggc gtc acc tcc ccc gag gac ctg tgg cgg<br>Ala Cys Arg Tyr Pro Gly Gly Val Thr Ser Pro Glu Asp Leu Trp Arg<br>1040       1045       1050 | 3172 |
| ctc gtc gcc gag ggg cgc gac gcc gtc tcg ggg ctg ccc acc gac cgc<br>Leu Val Ala Glu Gly Arg Asp Ala Val Ser Gly Leu Pro Thr Asp Arg<br>1055       1060       1065 | 3220 |
| ggc tgg gac gag gac ctc ttc gac gcc gac ccc gac cgc agc ggc aag<br>Gly Trp Asp Glu Asp Leu Phe Asp Ala Asp Pro Asp Arg Ser Gly Lys<br>1070       1075       1080 | 3268 |
| agc tcg gtc cgc gag gga gga ttc ctg cac gac gcc gcc ctg ttc gac<br>Ser Ser Val Arg Glu Gly Gly Phe Leu His Asp Ala Ala Leu Phe Asp<br>1085       1090       1095 | 3316 |
| gcc ggc ttc ttc ggg ata tcg ccc cgc gag gcc ctc ggc atg gac ccg<br>Ala Gly Phe Phe Gly Ile Ser Pro Arg Glu Ala Leu Gly Met Asp Pro<br>1100       1105       1110       1115 | 3364 |

```
cag cag cgg ctg ctc ctg gag acg gca tgg gag gcc gtg gag cgc gca      3412
Gln Gln Arg Leu Leu Leu Glu Thr Ala Trp Glu Ala Val Glu Arg Ala
            1120                1125                1130 ggg ctc gac ccc gaa ggc ctc aag ggc agc cgg acg gcc gtc ttc gtc      3460
Gly Leu Asp Pro Glu Gly Leu Lys Gly Ser Arg Thr Ala Val Phe Val
                1135                1140                1145 ggc gcc acc gcc ctg gac tac ggc ccg cgc atg cac gac ggc gcc gag      3508
Gly Ala Thr Ala Leu Asp Tyr Gly Pro Arg Met His Asp Gly Ala Glu
            1150                1155                1160 ggc gtc gag ggc cac ctc ctg acc ggg acc acg ccc agc gtg atg tcg      3556
Gly Val Glu Gly His Leu Leu Thr Gly Thr Thr Pro Ser Val Met Ser
        1165                1170                1175 ggc cgc atc gcc tac cag ctc ggc ctc acc ggt cct gcg gtc acc gtc      3604
Gly Arg Ile Ala Tyr Gln Leu Gly Leu Thr Gly Pro Ala Val Thr Val
1180                1185                1190                1195 gac acg gcc tgc tcg tcc tcg ctc gtc gcg ctg cac ctg gcc gtc cgt      3652
Asp Thr Ala Cys Ser Ser Ser Leu Val Ala Leu His Leu Ala Val Arg
                1200                1205                1210 tcg ctg cgg cag ggc gag tcg agc ctc gcg ctc gcc ggc gga gcg acc      3700
Ser Leu Arg Gln Gly Glu Ser Ser Leu Ala Leu Ala Gly Gly Ala Thr
            1215                1220                1225 gtc atg tcg aca ccg ggc atg ttc gtc gag ttc tcg cgg cag cgc ggc      3748
Val Met Ser Thr Pro Gly Met Phe Val Glu Phe Ser Arg Gln Arg Gly
        1230                1235                1240 ctc gcc gcc gac ggc cgc tcc aag gcc ttc tcc gac tcc gcc gac ggc      3796
Leu Ala Ala Asp Gly Arg Ser Lys Ala Phe Ser Asp Ser Ala Asp Gly
            1245                1250                1255 acc tcc tgg gcc gag ggc gtc ggc ctc ctc gtc gtc gag cgg ctc tcg      3844
Thr Ser Trp Ala Glu Gly Val Gly Leu Leu Val Val Glu Arg Leu Ser
1260                1265                1270                1275 gac gcc gag cgc aac ggc cac ccc gtg ctc gcc gtg atc cgg ggc agc      3892
Asp Ala Glu Arg Asn Gly His Pro Val Leu Ala Val Ile Arg Gly Ser
                1280                1285                1290 gcg gtc aac cag gac ggc gcc tcc aac ggg ctc acc gcc ccc aac ggc      3940
Ala Val Asn Gln Asp Gly Ala Ser Asn Gly Leu Thr Ala Pro Asn Gly
            1295                1300                1305 ccg tcc cag cag cgc gtc atc cga cag gcc ctg gcc gac gcc ggg ctc      3988
Pro Ser Gln Gln Arg Val Ile Arg Gln Ala Leu Ala Asp Ala Gly Leu
        1310                1315                1320 acc ccg gcc gac gtc gac gcc gtc gag gcg cac ggt acg ggt acc cgg      4036
Thr Pro Ala Asp Val Asp Ala Val Glu Ala His Gly Thr Gly Thr Arg
1325                1330                1335 ctc ggc gac ccc atc gag gcc gag gcg atc ctc ggc acc tac ggc cgg      4084
Leu Gly Asp Pro Ile Glu Ala Glu Ala Ile Leu Gly Thr Tyr Gly Arg
1340                1345                1350                1355 gac cgg ggc gag ggc gct ccg ctc cag ctc ggc tcg ctg aag tcg aac      4132
Asp Arg Gly Glu Gly Ala Pro Leu Gln Leu Gly Ser Leu Lys Ser Asn
                1360                1365                1370 atc ggc cac gcg cag gcc gcc gcg ggc gtg ggc ggg ctc atc aag atg      4180
Ile Gly His Ala Gln Ala Ala Ala Gly Val Gly Gly Leu Ile Lys Met
            1375                1380                1385 gtc ctc gcg atg cgc cac ggc gtc ctg ccc agg acg ctc cac gtg gac      4228
Val Leu Ala Met Arg His Gly Val Leu Pro Arg Thr Leu His Val Asp
        1390                1395                1400 cgg ccc acc acc cgc gtc gac tgg gag gcc ggc ggc gtc gag ctc ctc      4276
Arg Pro Thr Thr Arg Val Asp Trp Glu Ala Gly Gly Val Glu Leu Leu
1405                1410                1415 acc gag gag cgg gag tgg ccg gag acg ggc cgc ccg cgc cgc gcg gcg      4324
Thr Glu Glu Arg Glu Trp Pro Glu Thr Gly Arg Pro Arg Arg Ala Ala
```

-continued

```
         1420                1425                1430                1435
atc tcc tcc ttc ggc atc agc ggc acc aac gcc cac atc gtg gtc gaa       4372
Ile Ser Ser Phe Gly Ile Ser Gly Thr Asn Ala His Ile Val Val Glu
                     1440                1445                1450 cag gcc ccg gaa gcc ggg gag gcg gcg gtc acc acc acc gcc ccg gaa       4420
Gln Ala Pro Glu Ala Gly Glu Ala Ala Val Thr Thr Thr Ala Pro Glu
         1455                1460                1465 gca ggg gaa gcc ggg gaa gcg gcg gac acc acc gcc acc acg acg ccg       4468
Ala Gly Glu Ala Gly Glu Ala Ala Asp Thr Thr Ala Thr Thr Thr Pro
         1470                1475                1480 gcc gcg gtc ggc gtc ccc gaa ccc gta cgc gcc ccc gtc gtg gtc tcc       4516
Ala Ala Val Gly Val Pro Glu Pro Val Arg Ala Pro Val Val Val Ser
         1485                1490                1495 gcg cgg gac gcc gcc gcc ctg cgc gcc cag gcc gtt cgg ctg cgg acc       4564
Ala Arg Asp Ala Ala Ala Leu Arg Ala Gln Ala Val Arg Leu Arg Thr
1500                1505                1510                1515 ttc ctc gac ggc cga ccg gac gtc acc gtc gcc gac ctc gga cgc tcg       4612
Phe Leu Asp Gly Arg Pro Asp Val Thr Val Ala Asp Leu Gly Arg Ser
                     1520                1525                1530 ctg gcc gcc cgt acc gcc ttc gag cac aag gcc gcc ctc acc acc gcc       4660
Leu Ala Ala Arg Thr Ala Phe Glu His Lys Ala Ala Leu Thr Thr Ala
         1535                1540                1545 acc agg gac gag ctg ctc gcc ggg ctc gac gcc ctc ggc cgc ggg gag       4708
Thr Arg Asp Glu Leu Leu Ala Gly Leu Asp Ala Leu Gly Arg Gly Glu
         1550                1555                1560 caa gcc acg ggc ctg gtc acc ggc gaa ccg gcc agg gcc gga cgc acg       4756
Gln Ala Thr Gly Leu Val Thr Gly Glu Pro Ala Arg Ala Gly Arg Thr
         1565                1570                1575 gcc ttc ctg ttc acc ggc cag gga gcg cag cgc gtc gcc atg ggc gag       4804
Ala Phe Leu Phe Thr Gly Gln Gly Ala Gln Arg Val Ala Met Gly Glu
1580                1585                1590                1595 gaa ctg cgc gcc gcg cac ccc gtg ttc gcc gcc gcc ctc gac acc gtg       4852
Glu Leu Arg Ala Ala His Pro Val Phe Ala Ala Ala Leu Asp Thr Val
                     1600                1605                1610 tac gcg gcc ctc gac cgt cac ctc gac cgg ccg ctg cgg gag atc gtc       4900
Tyr Ala Ala Leu Asp Arg His Leu Asp Arg Pro Leu Arg Glu Ile Val
         1615                1620                1625 gcc gcc ggg gag gag ctg gac ctc acc gcg tac acc cag ccc gcc ctc       4948
Ala Ala Gly Glu Glu Leu Asp Leu Thr Ala Tyr Thr Gln Pro Ala Leu
         1630                1635                1640 ttc gcc ttc gag gtg gcg ctg ttc cgc ctc ctc gaa cac cac ggc ctc       4996
Phe Ala Phe Glu Val Ala Leu Phe Arg Leu Leu Glu His His Gly Leu
         1645                1650                1655 gtc ccc gac ctg ctc acc ggc cac tcc gtc ggc gag atc gcc gcc gcg       5044
Val Pro Asp Leu Leu Thr Gly His Ser Val Gly Glu Ile Ala Ala Ala
1660                1665                1670                1675 cac gtc gcc ggt gtc ctc tcc ctc gac gac gcc gca cgt ctc gtc acc       5092
His Val Ala Gly Val Leu Ser Leu Asp Asp Ala Ala Arg Leu Val Thr
                     1680                1685                1690 gcc cgc ggc cgg ctc atg cag tcg gcc cgc gag ggc ggc gcg atg atc       5140
Ala Arg Gly Arg Leu Met Gln Ser Ala Arg Glu Gly Gly Ala Met Ile
         1695                1700                1705 gcc gtg cag gcg ggc gag gcc gag gtc gtc gag tcc ctg aag ggc tac       5188
Ala Val Gln Ala Gly Glu Ala Glu Val Val Glu Ser Leu Lys Gly Tyr
         1710                1715                1720 gag ggc agg gtc gcc gtc gcc gcc gtc aac gga ccc acc gcc gtg gtc       5236
Glu Gly Arg Val Ala Val Ala Ala Val Asn Gly Pro Thr Ala Val Val
         1725                1730                1735 gtc tcc ggc gac gcg gac gcc gcc gag gag atc cgc gcc gta tgg gcg       5284
```

-continued

| | | |
|---|---|---|
| Val Ser Gly Asp Ala Asp Ala Glu Glu Ile Arg Ala Val Trp Ala<br>1740                 1745                 1750                 1755 | | |
| gga cgc ggc cgg cgc acc cgc agg ctg cgc gtc agc cac gcc ttc cac<br>Gly Arg Gly Arg Arg Thr Arg Arg Leu Arg Val Ser His Ala Phe His<br>                1760                 1765                 1770 | | 5332 |
| tcc ccg cac atg gac gac gtc ctc gac gag ttc ctc cgg gtc gcc gag<br>Ser Pro His Met Asp Asp Val Leu Asp Glu Phe Leu Arg Val Ala Glu<br>             1775                 1780                 1785 | | 5380 |
| ggc ctg acc ttc gag gag ccg cgg atc ccc gtc gtc tcc acg gtc acc<br>Gly Leu Thr Phe Glu Glu Pro Arg Ile Pro Val Val Ser Thr Val Thr<br>          1790                 1795                 1800 | | 5428 |
| ggc gcg ctc gtc acg tcc ggc gag ctc acc tcg ccc gcg tac tgg gtc<br>Gly Ala Leu Val Thr Ser Gly Glu Leu Thr Ser Pro Ala Tyr Trp Val<br>      1805                 1810                 1815 | | 5476 |
| gac cag atc cgg cgg ccc gtg cgc ttc ctg gac gcc gtc cgc acc ctg<br>Asp Gln Ile Arg Arg Pro Val Arg Phe Leu Asp Ala Val Arg Thr Leu<br>1820                 1825                 1830                 1835 | | 5524 |
| gcc gcc cag gac gcg acc gtc ctc gtc gag atc ggc ccc gac gcc gtc<br>Ala Ala Gln Asp Ala Thr Val Leu Val Glu Ile Gly Pro Asp Ala Val<br>             1840                 1845                 1850 | | 5572 |
| ctc acg gca ctc gcc gag gag gct ctc gcg ccc ggc acg gac gcc ccg<br>Leu Thr Ala Leu Ala Glu Glu Ala Leu Ala Pro Gly Thr Asp Ala Pro<br>          1855                 1860                 1865 | | 5620 |
| gac gcc cgg gac gtc acg gtc gtc ccg ctg ctg cgc gcg ggg cgc ccc<br>Asp Ala Arg Asp Val Thr Val Val Pro Leu Leu Arg Ala Gly Arg Pro<br>      1870                 1875                 1880 | | 5668 |
| gag ccc gag acc ctc gcc gcc ggt ctc gcg acc gcc cat gtc cac ggc<br>Glu Pro Glu Thr Leu Ala Ala Gly Leu Ala Thr Ala His Val His Gly<br>          1885                 1890                 1895 | | 5716 |
| gca ccc ttg gac cgg gcg tcg ttc ttc ccg gac ggg cgc cgc acg gac<br>Ala Pro Leu Asp Arg Ala Ser Phe Phe Pro Asp Gly Arg Arg Thr Asp<br>1900                 1905                 1910                 1915 | | 5764 |
| ctg ccc acg tac gcc ttc cgg cgc gag cac tac tgg ctg acg ccc gag<br>Leu Pro Thr Tyr Ala Phe Arg Arg Glu His Tyr Trp Leu Thr Pro Glu<br>             1920                 1925                 1930 | | 5812 |
| gcc cgt acg gac gcc cgc gca ctc ggc ttc gac ccg gcg cgg cac ccg<br>Ala Arg Thr Asp Ala Arg Ala Leu Gly Phe Asp Pro Ala Arg His Pro<br>          1935                 1940                 1945 | | 5860 |
| ctg ctg acg acc acg gtc gag gtc gcc ggc ggc gac ggc gtc ctg ctg<br>Leu Leu Thr Thr Thr Val Glu Val Ala Gly Gly Asp Gly Val Leu Leu<br>      1950                 1955                 1960 | | 5908 |
| acc ggc cgt ctc tcc ctg acc gac cag ccc tgg ctg gcc gac cac atg<br>Thr Gly Arg Leu Ser Leu Thr Asp Gln Pro Trp Leu Ala Asp His Met<br>          1965                 1970                 1975 | | 5956 |
| gtc aac ggc gcc gtc ctg ttg ccg gcc acc gcc ttc ctg gag ctc gcc<br>Val Asn Gly Ala Val Leu Leu Pro Ala Thr Ala Phe Leu Glu Leu Ala<br>1980                 1985                 1990                 1995 | | 6004 |
| ctc gcg gcg ggc gac cac gtc ggg gcg gtc cgg gtg gag gaa ctc acc<br>Leu Ala Ala Gly Asp His Val Gly Ala Val Arg Val Glu Glu Leu Thr<br>             2000                 2005                 2010 | | 6052 |
| ctc gaa gcg ccg ctc gtc ctg ccc gag cgg ggc gcc gtc cgc atc cag<br>Leu Glu Ala Pro Leu Val Leu Pro Glu Arg Gly Ala Val Arg Ile Gln<br>          2015                 2020                 2025 | | 6100 |
| gtc ggc gtg agc ggc gac ggc gag tcg ccg gcc ggg cgc acc ttc ggt<br>Val Gly Val Ser Gly Asp Gly Glu Ser Pro Ala Gly Arg Thr Phe Gly<br>             2030                 2035                 2040 | | 6148 |
| gtg tac agc acc ccc gac tcc ggc gac acc ggt gac gac gcg ccc cgg<br>Val Tyr Ser Thr Pro Asp Ser Gly Asp Thr Gly Asp Asp Ala Pro Arg<br>          2045                 2050                 2055 | | 6196 |

```
                                                           -continued gag tgg acc cgc cat gtc tcc ggc gta ctc ggc gaa ggg gac ccg gcc    6244
Glu Trp Thr Arg His Val Ser Gly Val Leu Gly Glu Gly Asp Pro Ala
2060                2065                2070                2075 acg gag tcg gac cac ccc ggc acc gac ggg gac ggt tca gcg gcc tgg    6292
Thr Glu Ser Asp His Pro Gly Thr Asp Gly Asp Gly Ser Ala Ala Trp
            2080                2085                2090 ccg cct gcg gcg gcg acc gcc aca ccc ctc gac ggc gtc tac gac cgg    6340
Pro Pro Ala Ala Ala Thr Ala Thr Pro Leu Asp Gly Val Tyr Asp Arg
        2095                2100                2105 ctc gcg gag ctc ggc tac gga tac ggt ccg gcc ttc cag ggc ctg acg    6388
Leu Ala Glu Leu Gly Tyr Gly Tyr Gly Pro Ala Phe Gln Gly Leu Thr
    2110                2115                2120 ggg ctg tgg cgc gac ggc gcc gac acg ctc gcc gag atc cgg ctg ccc    6436
Gly Leu Trp Arg Asp Gly Ala Asp Thr Leu Ala Glu Ile Arg Leu Pro
2125                2130                2135 gcg gcg cag cac gag agc gcg ggg ctc ttc ggc gta cac ccg gcg ctg    6484
Ala Ala Gln His Glu Ser Ala Gly Leu Phe Gly Val His Pro Ala Leu
2140                2145                2150                2155 ctc gac gcg gcg ctc cac ccg atc gtc ctg gag ggc aac tca gct gcc    6532
Leu Asp Ala Ala Leu His Pro Ile Val Leu Glu Gly Asn Ser Ala Ala
                2160                2165                2170 ggt gcc tgt gac gcc gat acc gac gcg acc gac cgg atc cgg ctg ccg    6580
Gly Ala Cys Asp Ala Asp Thr Asp Ala Thr Asp Arg Ile Arg Leu Pro
            2175                2180                2185 ttc gcg tgg gcg ggg gtg acc ctc cac gcc gaa ggg gcc acc gcg ctc    6628
Phe Ala Trp Ala Gly Val Thr Leu His Ala Glu Gly Ala Thr Ala Leu
        2190                2195                2200 cgc gta cgg atc aca ccc acc ggc ccg gac acg gtc acg ctc cgc ctc    6676
Arg Val Arg Ile Thr Pro Thr Gly Pro Asp Thr Val Thr Leu Arg Leu
    2205                2210                2215 acc gac acc acc ggt gcg ccc gtg gcc acc gtg gag tcc ctg acc ctg    6724
Thr Asp Thr Thr Gly Ala Pro Val Ala Thr Val Glu Ser Leu Thr Leu
2220                2225                2230                2235 cgc gcg gtg gcg aag gac cgg ctg ggc acc acc gcc ggg cgc gtc gac    6772
Arg Ala Val Ala Lys Asp Arg Leu Gly Thr Thr Ala Gly Arg Val Asp
                2240                2245                2250 gac gcc ctg ttc acg gtc gtg tgg acg gag acc ggc aca ccg gaa ccc    6820
Asp Ala Leu Phe Thr Val Val Trp Thr Glu Thr Gly Thr Pro Glu Pro
            2255                2260                2265 gca ggg cgc gga gcc gtg gag gtc gag gaa ctc gtc gac ctc gcc ggc    6868
Ala Gly Arg Gly Ala Val Glu Val Glu Glu Leu Val Asp Leu Ala Gly
        2270                2275                2280 ctc ggc gac ctc gtg gag ctc ggc gcc gcg gac gtc gtc ctc cgg gcc    6916
Leu Gly Asp Leu Val Glu Leu Gly Ala Ala Asp Val Val Leu Arg Ala
    2285                2290                2295 gac cgc tgg acg ctc gac ggg gac ccg tcc gcc gcc gcg cgc aca gcc    6964
Asp Arg Trp Thr Leu Asp Gly Asp Pro Ser Ala Ala Ala Arg Thr Ala
2300                2305                2310                2315 gtc cgg cgc acc ctc gcc atc gtc cag gag ttc ctg tcc gag ccg cgc    7012
Val Arg Arg Thr Leu Ala Ile Val Gln Glu Phe Leu Ser Glu Pro Arg
                2320                2325                2330 ttc gac ggc tcg cga ctg gtg tgc gtc acc agg ggc gcg gtc gcc gca    7060
Phe Asp Gly Ser Arg Leu Val Cys Val Thr Arg Gly Ala Val Ala Ala
            2335                2340                2345 ctc ccc ggc gag gac gtc acc tcc ctc gcc acc ggc ccc ctc tgg ggc    7108
Leu Pro Gly Glu Asp Val Thr Ser Leu Ala Thr Gly Pro Leu Trp Gly
        2350                2355                2360 ctc gtc cgc tcc gcc cag tcc gag aac ccg gga cgc ctg ttc ctc ctg    7156
Leu Val Arg Ser Ala Gln Ser Glu Asn Pro Gly Arg Leu Phe Leu Leu
    2365                2370                2375
```

```
gac ctg ggt gaa ggc gaa ggc gag cgc gac gga gcc gag gag ctg atc      7204
Asp Leu Gly Glu Gly Glu Gly Glu Arg Asp Gly Ala Glu Glu Leu Ile
2380            2385                2390                2395 cgc gcg gcc acg gcc ggg gac gag ccg cag ctc gcg gca cgg gac ggc      7252
Arg Ala Ala Thr Ala Gly Asp Glu Pro Gln Leu Ala Ala Arg Asp Gly
                2400                2405                2410 cga ctg ctc gcg ccg agg ctg gcc cgt acc gcc gcc ctt tcg agt gag      7300
Arg Leu Leu Ala Pro Arg Leu Ala Arg Thr Ala Ala Leu Ser Ser Glu
        2415                2420                2425 gac acc gcc ggc ggc gcc gac cgt ttc ggc ccc gac ggc acc gtc ctc      7348
Asp Thr Ala Gly Gly Ala Asp Arg Phe Gly Pro Asp Gly Thr Val Leu
2430                2435                2440 gtc acc ggg ggc acc gga ggc ctc gga gcg ctc ctc gcc cgc cac ctc      7396
Val Thr Gly Gly Thr Gly Gly Leu Gly Ala Leu Leu Ala Arg His Leu
    2445                2450                2455 gtg gag cgt cac ggg gtg cgc cgg ctg ctg ctg gtg agc cgc cgc ggg      7444
Val Glu Arg His Gly Val Arg Arg Leu Leu Leu Val Ser Arg Arg Gly
2460                2465                2470                2475 gcc gac gcc ccc ggc gcg gcc gac ctg ggc gag gac ctc gcg ggc ctc      7492
Ala Asp Ala Pro Gly Ala Ala Asp Leu Gly Glu Asp Leu Ala Gly Leu
                2480                2485                2490 ggc gcg gag gtg gcg ttc gcc gcc gcc gac gcc gcc gac cgc gag agc      7540
Gly Ala Glu Val Ala Phe Ala Ala Ala Asp Ala Ala Asp Arg Glu Ser
        2495                2500                2505 ctg gcg cgg gcg atc gcc acc gtg ccc gcc gag cat ccg ctg acg gcc      7588
Leu Ala Arg Ala Ile Ala Thr Val Pro Ala Glu His Pro Leu Thr Ala
2510                2515                2520 gtc gtg cac acg gcg gga gtc gtc gac gac gcg acg gtg gag gcg ctc      7636
Val Val His Thr Ala Gly Val Val Asp Asp Ala Thr Val Glu Ala Leu
    2525                2530                2535 aca ccg gaa cgg ctg gac gcg gta ctg cgc ccg aag gtc gac gcc gcg      7684
Thr Pro Glu Arg Leu Asp Ala Val Leu Arg Pro Lys Val Asp Ala Ala
2540                2545                2550                2555 tgg aac ctg cac gag ctc acc aag gac ctg cgg ctc gac gcc ttc gtc      7732
Trp Asn Leu His Glu Leu Thr Lys Asp Leu Arg Leu Asp Ala Phe Val
                2560                2565                2570 ctc ttc tcc tcc gtc tcc ggc atc gtc ggc acc gcc ggc cag gcc aac      7780
Leu Phe Ser Ser Val Ser Gly Ile Val Gly Thr Ala Gly Gln Ala Asn
        2575                2580                2585 tac gcg gcg gcc aac acg ggc ctc gac gcc ctc gcc gcc cac cgc gcc      7828
Tyr Ala Ala Ala Asn Thr Gly Leu Asp Ala Leu Ala Ala His Arg Ala
2590                2595                2600 gcc acg ggc ctg gcc gcc acg tcg ctg gcc tgg ggc ctc tgg gac ggc      7876
Ala Thr Gly Leu Ala Ala Thr Ser Leu Ala Trp Gly Leu Trp Asp Gly
    2605                2610                2615 acg cac ggc atg ggc ggc acg ctc ggc gcc gcc gac ctc gcc cgc tgg      7924
Thr His Gly Met Gly Gly Thr Leu Gly Ala Ala Asp Leu Ala Arg Trp
2620                2625                2630                2635 agc cgg gcc gga atc acc ccg ctc acc ccg ctg cag ggc ctc gcg ctc      7972
Ser Arg Ala Gly Ile Thr Pro Leu Thr Pro Leu Gln Gly Leu Ala Leu
                2640                2645                2650 ttc gac gcc gcg gtc gcc agg gac gac gcc ctc ctc gta ccc gcc ggg      8020
Phe Asp Ala Ala Val Ala Arg Asp Asp Ala Leu Leu Val Pro Ala Gly
        2655                2660                2665 ctc cgt ccc acc gcc cac cgg ggc acg gac gga cag cct cct gcg ctg      8068
Leu Arg Pro Thr Ala His Arg Gly Thr Asp Gly Gln Pro Pro Ala Leu
2670                2675                2680 tgg cgc ggc ctc gtc cgg gcg cgc ccg cgc cgt gcc gcg cgg acg gcc      8116
Trp Arg Gly Leu Val Arg Ala Arg Pro Arg Arg Ala Ala Arg Thr Ala
```

```
                    2685                  2690                  2695
gcc gag gcg gcg gac acg acc ggc ggc tgg ctg agc ggg ctc gcc gca     8164
Ala Glu Ala Ala Asp Thr Thr Gly Gly Trp Leu Ser Gly Leu Ala Ala
2700                2705                  2710                  2715 cag tcc ccc gag gag cgg cgc agc aca gcc gtc acg ctc gtg acg ggt     8212
Gln Ser Pro Glu Glu Arg Arg Ser Thr Ala Val Thr Leu Val Thr Gly
            2720                  2725                  2730 gtc gtc gcg gac gtc ctc ggg cac gcc gac tcc gcc gcg gtc ggg gcg     8260
Val Val Ala Asp Val Leu Gly His Ala Asp Ser Ala Ala Val Gly Ala
        2735                  2740                  2745 gag cgg tcc ttc aag gac ctc ggc ttc gac tcc ctg gcc ggg gtg gag     8308
Glu Arg Ser Phe Lys Asp Leu Gly Phe Asp Ser Leu Ala Gly Val Glu
    2750                  2755                  2760 ctc cgc aac cgg ctg aac gcc gcc acc ggc ctg cgg ctc ccc gcg acc     8356
Leu Arg Asn Arg Leu Asn Ala Ala Thr Gly Leu Arg Leu Pro Ala Thr
2765                  2770                  2775 acg gtc ttc gac cat ccc tcg ccg gcc gcg ctc gcg tcc cat ctc ctc     8404
Thr Val Phe Asp His Pro Ser Pro Ala Ala Leu Ala Ser His Leu Leu
2780                  2785                  2790                  2795 gcc cag gtg ccc ggg ttg aag gag ggg acg gcg gcg acc gcg acc gtc     8452
Ala Gln Val Pro Gly Leu Lys Glu Gly Thr Ala Ala Thr Ala Thr Val
            2800                  2805                  2810 gtg gcc gag cgg ggc gct tcc ttc ggt gac cgt gcg acc gac gac gat     8500
Val Ala Glu Arg Gly Ala Ser Phe Gly Asp Arg Ala Thr Asp Asp Asp
        2815                  2820                  2825 ccg atc gcg atc gtg ggc atg gca tgc cgc tat ccg ggt ggt gtg tcg     8548
Pro Ile Ala Ile Val Gly Met Ala Cys Arg Tyr Pro Gly Gly Val Ser
    2830                  2835                  2840 tcg ccg gag gac ctg tgg cgg ctg gtg gcc gag ggg acg gac gcg atc     8596
Ser Pro Glu Asp Leu Trp Arg Leu Val Ala Glu Gly Thr Asp Ala Ile
2845                  2850                  2855 agc gag ttc ccc gtc aac cgc ggc tgg gac ctg gag agc ctc tac gac     8644
Ser Glu Phe Pro Val Asn Arg Gly Trp Asp Leu Glu Ser Leu Tyr Asp
2860                  2865                  2870                  2875 ccg gat ccc gag tcg aag ggc acc acg tac tgc cgg gag ggc ggg ttc     8692
Pro Asp Pro Glu Ser Lys Gly Thr Thr Tyr Cys Arg Glu Gly Gly Phe
            2880                  2885                  2890 ctg gaa ggc gcc ggt gac ttc gac gcc gcc ttc ttc ggc atc tcg ccg     8740
Leu Glu Gly Ala Gly Asp Phe Asp Ala Ala Phe Phe Gly Ile Ser Pro
        2895                  2900                  2905 cgc gag gcc ctg gtg atg gac ccg cag cag cgg ctg ctg ctg gag gtg     8788
Arg Glu Ala Leu Val Met Asp Pro Gln Gln Arg Leu Leu Leu Glu Val
    2910                  2915                  2920 tcc tgg gag gcg ctg gaa cgc gcg ggc atc gac ccg tcc tcg ctg cgc     8836
Ser Trp Glu Ala Leu Glu Arg Ala Gly Ile Asp Pro Ser Ser Leu Arg
2925                  2930                  2935 ggc agc cgc ggt ggt gtc tac gtg ggc gcc gcg cac ggc tcg tac gcc     8884
Gly Ser Arg Gly Gly Val Tyr Val Gly Ala Ala His Gly Ser Tyr Ala
2940                  2945                  2950                  2955 tcc gat ccc cgg ctg gtg ccc gag ggc tcg gag ggc tat ctg ctg acc     8932
Ser Asp Pro Arg Leu Val Pro Glu Gly Ser Glu Gly Tyr Leu Leu Thr
            2960                  2965                  2970 ggc agc gcc gac gcg gtg atg tcc ggc cgc atc tcc tac gcg ctc ggt     8980
Gly Ser Ala Asp Ala Val Met Ser Gly Arg Ile Ser Tyr Ala Leu Gly
        2975                  2980                  2985 ctc gaa gga ccg tcc atg acg gtg gag acg gcc tgc tcc tcc tcg ctg     9028
Leu Glu Gly Pro Ser Met Thr Val Glu Thr Ala Cys Ser Ser Ser Leu
    2990                  2995                  3000 gtg gcg ctg cat ctg gcg gta cgg gcg ctg cgg cac ggc gag tgc ggg     9076
```

-continued

| | |
|---|---|
| Val Ala Leu His Leu Ala Val Arg Ala Leu Arg His Gly Glu Cys Gly<br>3005                3010                3015 | |
| ctc gcg ctg gcg ggc ggg gtg gcg gtg atg gcc gat ccg gcg gcg ttc<br>Leu Ala Leu Ala Gly Gly Val Ala Val Met Ala Asp Pro Ala Ala Phe<br>3020                3025                3030                3035 | 9124 |
| gtg gag ttc tcc cgg cag aag ggg ctg gcc gcc gac ggc cgc tgc aag<br>Val Glu Phe Ser Arg Gln Lys Gly Leu Ala Ala Asp Gly Arg Cys Lys<br>3040                3045                3050 | 9172 |
| gcg ttc tcg gcc gcc gcc gac ggc acc ggc tgg gcc gag ggc gtc ggc<br>Ala Phe Ser Ala Ala Ala Asp Gly Thr Gly Trp Ala Glu Gly Val Gly<br>3055                3060                3065 | 9220 |
| gtg ctc gtc ctg gag cgg ctg tcg gac gcg cgc cgc gcg ggg cac acg<br>Val Leu Val Leu Glu Arg Leu Ser Asp Ala Arg Arg Ala Gly His Thr<br>3070                3075                3080 | 9268 |
| gtc ctc ggc ctg gtc acc ggc acc gcg gtc aac cag gac ggt gcc tcc<br>Val Leu Gly Leu Val Thr Gly Thr Ala Val Asn Gln Asp Gly Ala Ser<br>3085                3090                3095 | 9316 |
| aac ggg ctg acc gcg ccc aac ggc cca gcc cag caa cgc gtc atc gcc<br>Asn Gly Leu Thr Ala Pro Asn Gly Pro Ala Gln Gln Arg Val Ile Ala<br>3100                3105                3110                3115 | 9364 |
| gag gcg ctc gcc gac gcc ggg ctg tcc ccg gag gac gtg gac gcg gtc<br>Glu Ala Leu Ala Asp Ala Gly Leu Ser Pro Glu Asp Val Asp Ala Val<br>3120                3125                3130 | 9412 |
| gag gcg cac ggc acc ggc acc cgg ctc ggc gac ccc atc gag gcc ggg<br>Glu Ala His Gly Thr Gly Thr Arg Leu Gly Asp Pro Ile Glu Ala Gly<br>3135                3140                3145 | 9460 |
| gcg ctc ctc gcc gcc tcc gga cgg aac cgt tcc ggc gac cac ccg ctg<br>Ala Leu Leu Ala Ala Ser Gly Arg Asn Arg Ser Gly Asp His Pro Leu<br>3150                3155                3160 | 9508 |
| tgg ctc ggc tcg ctg aag tcc aac atc ggg cat gcc cag gcc gcc gcc<br>Trp Leu Gly Ser Leu Lys Ser Asn Ile Gly His Ala Gln Ala Ala Ala<br>3165                3170                3175 | 9556 |
| ggt gtc ggc ggc gtc atc aag atg ctc cag gcg ctg cgg cac ggc ttg<br>Gly Val Gly Gly Val Ile Lys Met Leu Gln Ala Leu Arg His Gly Leu<br>3180                3185                3190                3195 | 9604 |
| ctg ccc cgc acc ctc cac gcc gac gag ccg acc ccg cat gcc gac tgg<br>Leu Pro Arg Thr Leu His Ala Asp Glu Pro Thr Pro His Ala Asp Trp<br>3200                3205                3210 | 9652 |
| agc tcc ggc cgg gta cgg ctg ctc acc tcc gag gtg ccg tgg cag cgg<br>Ser Ser Gly Arg Val Arg Leu Leu Thr Ser Glu Val Pro Trp Gln Arg<br>3215                3220                3225 | 9700 |
| acc ggc cgg ccc cgg cgg acc ggg gtg tcc gcc ttc ggc gtc ggc ggc<br>Thr Gly Arg Pro Arg Arg Thr Gly Val Ser Ala Phe Gly Val Gly Gly<br>3230                3235                3240 | 9748 |
| acc aat gcc cat gtc gtc ctc gaa gag gca ccc gcc ccg ccc gcg ccg<br>Thr Asn Ala His Val Val Leu Glu Glu Ala Pro Ala Pro Pro Ala Pro<br>3245                3250                3255 | 9796 |
| gaa ccg gcc ggg gag gcc ccc ggc ggc tcc cgc gcc gca gaa ggg gcg<br>Glu Pro Ala Gly Glu Ala Pro Gly Gly Ser Arg Ala Ala Glu Gly Ala<br>3260                3265                3270                3275 | 9844 |
| gaa ggg ccc ctg gcc tgg gtg gtc tcc gga cgc gac gag ccg gcc ctg<br>Glu Gly Pro Leu Ala Trp Val Val Ser Gly Arg Asp Glu Pro Ala Leu<br>3280                3285                3290 | 9892 |
| cgg tcc cag gcc cgg cgg ctc cgc gac cac ctc tcc cgc acc ccc ggg<br>Arg Ser Gln Ala Arg Arg Leu Arg Asp His Leu Ser Arg Thr Pro Gly<br>3295                3300                3305 | 9940 |
| gcc cgc ccg cgt gac atc gcc ttc tcc ctc gcc gcc acg cgc gca gcc<br>Ala Arg Pro Arg Asp Ile Ala Phe Ser Leu Ala Ala Thr Arg Ala Ala<br>3310                3315                3320 | 9988 |

-continued

| | |
|---|---|
| ttt gac cac cgc gcc gtg ctg atc ggc tcg gac ggg gcc gaa ctc gcc<br>Phe Asp His Arg Ala Val Leu Ile Gly Ser Asp Gly Ala Glu Leu Ala<br>    3325                            3330                        3335 | 10036 |
| gcc gcc ctg gac gcg ttg gcc gaa gga cgc gac ggt ccg gcg gtg gtg<br>Ala Ala Leu Asp Ala Leu Ala Glu Gly Arg Asp Gly Pro Ala Val Val<br>3340                      3345                      3350                      3355 | 10084 |
| cgc gga gtc cgc gac cgg gac ggc agg atg gcc ttc ctc ttc acc ggg<br>Arg Gly Val Arg Asp Arg Asp Gly Arg Met Ala Phe Leu Phe Thr Gly<br>    3360                            3365                        3370 | 10132 |
| cag ggc agc cag cgc gcc ggg atg gcc cac gac ctg cat gcc gcc cat<br>Gln Gly Ser Gln Arg Ala Gly Met Ala His Asp Leu His Ala Ala His<br>        3375                          3380                        3385 | 10180 |
| acc ttc ttc gcg tcc gcc ctc gac gag gtg acg gac cgt ctc gac ccg<br>Thr Phe Phe Ala Ser Ala Leu Asp Glu Val Thr Asp Arg Leu Asp Pro<br>    3390                            3395                        3400 | 10228 |
| ctg ctc ggc cgg ccg ctc ggc gcg ctg ctg gac gcc cga ccc ggc tcg<br>Leu Leu Gly Arg Pro Leu Gly Ala Leu Leu Asp Ala Arg Pro Gly Ser<br>3405                      3410                      3415 | 10276 |
| ccc gaa gcg gca ctc ctg gac cgg acc gag tac acc cag ccg gcg ctc<br>Pro Glu Ala Ala Leu Leu Asp Arg Thr Glu Tyr Thr Gln Pro Ala Leu<br>3420                      3425                      3430                      3435 | 10324 |
| ttc gcc gtc gag gtg gcg ctc cac cgg ctg ctg gag cac tgg ggg atg<br>Phe Ala Val Glu Val Ala Leu His Arg Leu Leu Glu His Trp Gly Met<br>            3440                      3445                      3450 | 10372 |
| cgc ccc gac ctg ctg ctg ggg cac tcg gtg ggc gaa ctg gcg gcc gcc<br>Arg Pro Asp Leu Leu Leu Gly His Ser Val Gly Glu Leu Ala Ala Ala<br>                3455                      3460                      3465 | 10420 |
| cac gtc gcg ggt gtg ctc gat ctc gac gac gcc tgc gcg ctg gtg gcc<br>His Val Ala Gly Val Leu Asp Leu Asp Asp Ala Cys Ala Leu Val Ala<br>            3470                      3475                      3480 | 10468 |
| gcc cgc ggc agg ctg atg cag cgc ctg ccg ccc ggc ggc gcg atg gtc<br>Ala Arg Gly Arg Leu Met Gln Arg Leu Pro Pro Gly Gly Ala Met Val<br>3485                      3490                      3495 | 10516 |
| tcc gtg cgg gcc ggc gag gac gag gtc cgc gca ctg ctg gcc ggc cgc<br>Ser Val Arg Ala Gly Glu Asp Glu Val Arg Ala Leu Leu Ala Gly Arg<br>3500                      3505                      3510                      3515 | 10564 |
| gag gac gcc gtc tgc gtc gcc gcg gtg aac ggc ccc cgg tcg gtg gtg<br>Glu Asp Ala Val Cys Val Ala Ala Val Asn Gly Pro Arg Ser Val Val<br>                3520                      3525                      3530 | 10612 |
| atc tcc ggc gcg gag gaa gcg gtg gcc gag gcg gcg gcg cag ctc gcc<br>Ile Ser Gly Ala Glu Glu Ala Val Ala Glu Ala Ala Ala Gln Leu Ala<br>            3535                      3540                      3545 | 10660 |
| gga cga ggc cgc cgc acc agg cgg ctc cgc gtc gcg cac gcc ttc cac<br>Gly Arg Gly Arg Arg Thr Arg Arg Leu Arg Val Ala His Ala Phe His<br>    3550                            3555                        3560 | 10708 |
| tca ccc ctg atg gac ggc atg ctc gcc gga ttc cgg gag gtc gcc gcc<br>Ser Pro Leu Met Asp Gly Met Leu Ala Gly Phe Arg Glu Val Ala Ala<br>        3565                          3570                      3575 | 10756 |
| ggc ctg cgc tac cgg gaa ccg gag ctg acg gtc gtc tcc acg gtc acg<br>Gly Leu Arg Tyr Arg Glu Pro Glu Leu Thr Val Val Ser Thr Val Thr<br>3580                      3585                      3590                      3595 | 10804 |
| ggg cgg ccc gcc cgc ccc ggt gaa ctc acc ggc ccc gac tac tgg gtg<br>Gly Arg Pro Ala Arg Pro Gly Glu Leu Thr Gly Pro Asp Tyr Trp Val<br>                3600                      3605                      3610 | 10852 |
| gcc cag gtc cgt gag ccc gtg cgc ttc gcg gac gcg gtc cgc acg gca<br>Ala Gln Val Arg Glu Pro Val Arg Phe Ala Asp Ala Val Arg Thr Ala<br>            3615                      3620                      3625 | 10900 |
| cac cgc ctc gga gcc cgc acc ttc ctg gag acc ggc ccg gac ggc gtg<br>His Arg Leu Gly Ala Arg Thr Phe Leu Glu Thr Gly Pro Asp Gly Val<br>            3630                      3635                      3640 | 10948 |

-continued

| | |
|---|---|
| ctg tgc ggc atg gca gag gag tgc ctg gag gac gac acc gtg gcc ctg<br>Leu Cys Gly Met Ala Glu Glu Cys Leu Glu Asp Asp Thr Val Ala Leu<br>3645                                  3650                                  3655 | 10996 |
| ctg ccg gcg atc cac aag ccc ggc acc gcg ccg cac ggt ccg gcg gct<br>Leu Pro Ala Ile His Lys Pro Gly Thr Ala Pro His Gly Pro Ala Ala<br>3660                                    3665                                  3670                                  3675 | 11044 |
| ccc ggc gcg ctg cgg gcg gcc gcc gcc gcg tac ggc cgg ggc gcc cgg<br>Pro Gly Ala Leu Arg Ala Ala Ala Ala Ala Tyr Gly Arg Gly Ala Arg<br>3680                                    3685                                  3690 | 11092 |
| gtg gac tgg gcc ggg atg cac gcc gac ggc ccc gag ggg ccg gcc cgc<br>Val Asp Trp Ala Gly Met His Ala Asp Gly Pro Glu Gly Pro Ala Arg<br>3695                                    3700                                  3705 | 11140 |
| cgc gtc gaa ctg ccc gtc cac gcc ttc cgg cac cgc cgc tac tgg ctc<br>Arg Val Glu Leu Pro Val His Ala Phe Arg His Arg Arg Tyr Trp Leu<br>3710                                    3715                                  3720 | 11188 |
| gcc ccg ggc cgc gcg gcg gac acc gac gac tgg atg tac cgg atc ggc<br>Ala Pro Gly Arg Ala Ala Asp Thr Asp Asp Trp Met Tyr Arg Ile Gly<br>3725                                    3730                                  3735 | 11236 |
| tgg gac cgg ctg ccg gct gtg acc ggc ggg gcc cgg acc gcc ggc cgc<br>Trp Asp Arg Leu Pro Ala Val Thr Gly Gly Ala Arg Thr Ala Gly Arg<br>3740                                    3745                                  3750                                  3755 | 11284 |
| tgg ctg gtg atc cac ccc gac agc ccg cgc tgc cgg gag ctg tcc ggc<br>Trp Leu Val Ile His Pro Asp Ser Pro Arg Cys Arg Glu Leu Ser Gly<br>3760                                    3765                                  3770 | 11332 |
| cac gcc gaa cgc gcg ctg cgc gcc gcg ggc gcg agc ccc gta ccg ctg<br>His Ala Glu Arg Ala Leu Arg Ala Ala Gly Ala Ser Pro Val Pro Leu<br>3775                                    3780                                  3785 | 11380 |
| ccc gtg gac gct ccg gcc gcc gac cgg gcg tcc ttc gcg gca ctg ctg<br>Pro Val Asp Ala Pro Ala Ala Asp Arg Ala Ser Phe Ala Ala Leu Leu<br>3790                                    3795                                  3800 | 11428 |
| cgc tcc gcc acc gga cct gac aca cga ggt gac aca gcc gcg ccc gtg<br>Arg Ser Ala Thr Gly Pro Asp Thr Arg Gly Asp Thr Ala Ala Pro Val<br>3805                                    3810                                  3815 | 11476 |
| gcc ggt gtg ctg tcg ctg ctg tcc gag gag gat cgg ccc cat cgc cag<br>Ala Gly Val Leu Ser Leu Leu Ser Glu Glu Asp Arg Pro His Arg Gln<br>3820                                    3825                                  3830                                  3835 | 11524 |
| cac gcc ccg gta ccc gcc ggg gtc ctg gcg acg ctg tcc ctg atg cag<br>His Ala Pro Val Pro Ala Gly Val Leu Ala Thr Leu Ser Leu Met Gln<br>3840                                    3845                                  3850 | 11572 |
| gct atg gag gag gag gcg gtg gag gct cgc gtg tgg tgc gtc tcc cgc<br>Ala Met Glu Glu Glu Ala Val Glu Ala Arg Val Trp Cys Val Ser Arg<br>3855                                    3860                                  3865 | 11620 |
| gcc gcg gtc gcc gcc gcc gac cgg gaa cgg ccc gtc ggc gcg ggc gcc<br>Ala Ala Val Ala Ala Ala Asp Arg Glu Arg Pro Val Gly Ala Gly Ala<br>3870                                    3875                                  3880 | 11668 |
| gcc ctg tgg ggg ctg ggg cgg gtg gcc gcc ctg gaa cgc ccc acc cgg<br>Ala Leu Trp Gly Leu Gly Arg Val Ala Ala Leu Glu Arg Pro Thr Arg<br>3885                                    3890                                  3895 | 11716 |
| tgg ggc ggt ctc gtg gac ctg ccc gcc tcg ccc ggt gcg gcg cac tgg<br>Trp Gly Gly Leu Val Asp Leu Pro Ala Ser Pro Gly Ala Ala His Trp<br>3900                                    3905                                  3910                                  3915 | 11764 |
| gcg gcc gcc gtg gaa cgg ctc gcc ggt ccc gag gac cag atc gcc gtg<br>Ala Ala Ala Val Glu Arg Leu Ala Gly Pro Glu Asp Gln Ile Ala Val<br>3920                                    3925                                  3930 | 11812 |
| cgc gcg tcc ggc agt tgg ggc cgg cgc ctc acc agg ctg ccg cgc gac<br>Arg Ala Ser Gly Ser Trp Gly Arg Arg Leu Thr Arg Leu Pro Arg Asp<br>3935                                    3940                                  3945 | 11860 |
| ggc ggc ggc cgg acg gcc gca ccc gcg tac cgg ccg cgc ggc acg gtg<br>Gly Gly Gly Arg Thr Ala Ala Pro Ala Tyr Arg Pro Arg Gly Thr Val | 11908 |

-continued

| | | |
|---|---|---|
| ctc gtc acc ggt ggc acc ggc gcg ctc ggc ggg cat ctc gcc cgc tgg<br>Leu Val Thr Gly Gly Thr Gly Ala Leu Gly Gly His Leu Ala Arg Trp<br>3965                               3970                                 3975 | 11956 |
| ctc gcc gcg gcg ggc gcc gaa cac ctg gcg ctc acc agc cgc cgg ggc<br>Leu Ala Ala Ala Gly Ala Glu His Leu Ala Leu Thr Ser Arg Arg Gly<br>3980                          3985                        3990                        3995 | 12004 |
| ccg gac gcg ccc ggc gcc gcc gga ctc gag gcc gaa ctc ctc ctc ctg<br>Pro Asp Ala Pro Gly Ala Ala Gly Leu Glu Ala Glu Leu Leu Leu Leu<br>                4000                        4005                        4010 | 12052 |
| ggc gcc aag gtg acg ttc gcc gcc tgc gac acc gcc gac cgc gac ggc<br>Gly Ala Lys Val Thr Phe Ala Ala Cys Asp Thr Ala Asp Arg Asp Gly<br>                4015                        4020                        4025 | 12100 |
| ctc gcc cgg gtc ctg cgg gcg ata ccg gag gac acc ccg ctc acc gcg<br>Leu Ala Arg Val Leu Arg Ala Ile Pro Glu Asp Thr Pro Leu Thr Ala<br>                4030                        4035                        4040 | 12148 |
| gtg ttc cac gcc gcg ggc gta ccg cag gtc acg ccg ctg tcc cgt acc<br>Val Phe His Ala Ala Gly Val Pro Gln Val Thr Pro Leu Ser Arg Thr<br>                4045                        4050                        4055 | 12196 |
| tcg ccc gag cac ttc gcc gac gtg tac gcg ggc aag gcg gcg ggc gcc<br>Ser Pro Glu His Phe Ala Asp Val Tyr Ala Gly Lys Ala Ala Gly Ala<br>4060                          4065                        4070                        4075 | 12244 |
| gcg cac ctg gac gaa ctg acc cgc gaa ctc ggc gcc gga ctc gac gcg<br>Ala His Leu Asp Glu Leu Thr Arg Glu Leu Gly Ala Gly Leu Asp Ala<br>                4080                        4085                        4090 | 12292 |
| ttc gtc ctc tac tcc tcc ggc gcc ggc gtc tgg ggc agc gcc ggc cag<br>Phe Val Leu Tyr Ser Ser Gly Ala Gly Val Trp Gly Ser Ala Gly Gln<br>                4095                        4100                        4105 | 12340 |
| ggt gcc tac gcc gcc gcc aac gcc gcc ctg gac gcg ctc gcc cgg cgc<br>Gly Ala Tyr Ala Ala Ala Asn Ala Ala Leu Asp Ala Leu Ala Arg Arg<br>                4110                        4115                        4120 | 12388 |
| cgt gcg gcg gac gga ctc ccc gcc acc tcc atc gcc tgg ggc gtg tgg<br>Arg Ala Ala Asp Gly Leu Pro Ala Thr Ser Ile Ala Trp Gly Val Trp<br>            4125                        4130                        4135 | 12436 |
| ggc ggc ggc ggt atg ggg gcc gac gag gcg ggc gcg gag tat ctg ggc<br>Gly Gly Gly Gly Met Gly Ala Asp Glu Ala Gly Ala Glu Tyr Leu Gly<br>4140                          4145                        4150                        4155 | 12484 |
| cgg cgc ggt atg cgc ccc atg gca ccg gtc tcc gcg ctc cgg gcg atg<br>Arg Arg Gly Met Arg Pro Met Ala Pro Val Ser Ala Leu Arg Ala Met<br>                4160                        4165                        4170 | 12532 |
| gcc acc gcc atc gcc tcc ggg gaa ccc tgc ccc acc gtc acc cac acc<br>Ala Thr Ala Ile Ala Ser Gly Glu Pro Cys Pro Thr Val Thr His Thr<br>                4175                        4180                        4185 | 12580 |
| gac tgg gag cgc ttc ggc gag ggc ttc acc gcc ttc cgg ccc agc cct<br>Asp Trp Glu Arg Phe Gly Glu Gly Phe Thr Ala Phe Arg Pro Ser Pro<br>            4190                        4195                        4200 | 12628 |
| ctg atc gcg ggg ctc ggc acg ccg ggc ggc cgg gcg gcg gag acc<br>Leu Ile Ala Gly Leu Gly Thr Pro Gly Gly Arg Ala Ala Glu Thr<br>4205                          4210                        4215 | 12676 |
| ccc gag gag ggg aac gcc acc gct gcg gcg gac ctc acc gcc ctg ccg<br>Pro Glu Glu Gly Asn Ala Thr Ala Ala Ala Asp Leu Thr Ala Leu Pro<br>4220                          4225                        4230                        4235 | 12724 |
| ccc gcc gaa ctc cgc acc gcg ctg cgc gag ctg gtg cga gcc cgg acc<br>Pro Ala Glu Leu Arg Thr Ala Leu Arg Glu Leu Val Arg Ala Arg Thr<br>                4240                        4245                        4250 | 12772 |
| gcc gcg gcg ctc ggc ctc gac gac ccg gcc gag gtc gcc gag ggc gaa<br>Ala Ala Ala Leu Gly Leu Asp Asp Pro Ala Glu Val Ala Glu Gly Glu<br>                4255                        4260                        4265 | 12820 |
| cgg ttc ccc gcc atg ggc ttc gac tcc ctg gcc acc gta cgg ctg cgc | 12868 |

```
                Arg Phe Pro Ala Met Gly Phe Asp Ser Leu Ala Thr Val Arg Leu Arg
                    4270            4275                4280 cgc gga ctc gcc tcg gcc acg ggc ctc gac ctg ccc ccc gat ctg ctc      12916
Arg Gly Leu Ala Ser Ala Thr Gly Leu Asp Leu Pro Pro Asp Leu Leu
        4285            4290            4295 ttc gac cgg gac acc ccg gcc gcg ctc gcc gcc cac ctg gcc gaa ctg      12964
Phe Asp Arg Asp Thr Pro Ala Ala Leu Ala Ala His Leu Ala Glu Leu
4300            4305            4310            4315 ctc gcc acc gca cgg gac cac gga ccc ggc ggc ccc ggg acc ggt gcc      13012
Leu Ala Thr Ala Arg Asp His Gly Pro Gly Gly Pro Gly Thr Gly Ala
            4320            4325            4330 gcg ccg gcc gat gcc gga agc ggc ctg ccg gcc ctc tac cgg gag gcc      13060
Ala Pro Ala Asp Ala Gly Ser Gly Leu Pro Ala Leu Tyr Arg Glu Ala
                4335            4340            4345 gtc cgc acc ggc cgg gcc gcg gaa atg gcc gaa ctg ctc gcc gcc gct      13108
Val Arg Thr Gly Arg Ala Ala Glu Met Ala Glu Leu Leu Ala Ala Ala
        4350            4355            4360 tcc cgg ttc cgc ccc gcc ttc ggg acg gcg gac cgg cag ccg gtg gcc      13156
Ser Arg Phe Arg Pro Ala Phe Gly Thr Ala Asp Arg Gln Pro Val Ala
        4365            4370            4375 ctc gtg ccg ctg gcc gac ggc gcg gag gac acc ggg ctc ccg ctg ctc      13204
Leu Val Pro Leu Ala Asp Gly Ala Glu Asp Thr Gly Leu Pro Leu Leu
4380            4385            4390            4395 gtg ggc tgc gcc ggg acg gcg gtg gcc tcc ggc ccg gtg gag ttc acc      13252
Val Gly Cys Ala Gly Thr Ala Val Ala Ser Gly Pro Val Glu Phe Thr
                4400            4405            4410 gcc ttc gcc gga gcg ctg gcg gac ctc ccg gcg gcg gcc ccg atg gcc      13300
Ala Phe Ala Gly Ala Leu Ala Asp Leu Pro Ala Ala Ala Pro Met Ala
            4415            4420            4425 gcg ctg ccg cag ccc ggc ttt ctg ccg gga gaa cga gtc ccg gcc acc      13348
Ala Leu Pro Gln Pro Gly Phe Leu Pro Gly Glu Arg Val Pro Ala Thr
        4430            4435            4440 ccg gag gca ttg ttc gag gcc cag gcg gaa gcg ctg ctg cgc tac gcg      13396
Pro Glu Ala Leu Phe Glu Ala Gln Ala Glu Ala Leu Leu Arg Tyr Ala
        4445            4450            4455 gcc ggc cgg ccc ttc gtg ctg ctg ggg cac tcc gcc ggc gcc aac atg      13444
Ala Gly Arg Pro Phe Val Leu Leu Gly His Ser Ala Gly Ala Asn Met
4460            4465            4470            4475 gcc cac gcc ctg acc cgt cat ctg gag gcg aac ggt ggc ggc ccc gca      13492
Ala His Ala Leu Thr Arg His Leu Glu Ala Asn Gly Gly Gly Pro Ala
                4480            4485            4490 ggg ctg gtg ctc atg gac atc tac acc ccc gcc gac ccc ggc gcg atg      13540
Gly Leu Val Leu Met Asp Ile Tyr Thr Pro Ala Asp Pro Gly Ala Met
            4495            4500            4505 ggc gtc tgg cgg aac gac atg ttc cag tgg gtc tgg cgg cgc tcg gac      13588
Gly Val Trp Arg Asn Asp Met Phe Gln Trp Val Trp Arg Arg Ser Asp
        4510            4515            4520 atc ccc ccg gac gac cac cgc ctc acg gcc atg ggc gcc tac cac cgg      13636
Ile Pro Pro Asp Asp His Arg Leu Thr Ala Met Gly Ala Tyr His Arg
        4525            4530            4535 ctg ctt ctc gac tgg tcg ccc acc ccc gtc cgc gcc ccc gta ctg cat      13684
Leu Leu Leu Asp Trp Ser Pro Thr Pro Val Arg Ala Pro Val Leu His
4540            4545            4550            4555 ctg cgc gcc gcg gaa ccc atg ggc gac tgg cca ccc ggg gac acc ggc      13732
Leu Arg Ala Ala Glu Pro Met Gly Asp Trp Pro Pro Gly Asp Thr Gly
                4560            4565            4570 tgg cag tcc cac tgg gac ggc gcg cac acc acc gcc ggc atc ccc gga      13780
Trp Gln Ser His Trp Asp Gly Ala His Thr Thr Ala Gly Ile Pro Gly
            4575            4580            4585
```

| | | |
|---|---|---|
| aac cac ttc acg atg atg acc gaa cac gcc tcc gcc gcc gcc cgg ctc<br>Asn His Phe Thr Met Met Thr Glu His Ala Ser Ala Ala Ala Arg Leu<br>          4590                      4595                  4600 | 13828 |
| gtg cac ggc tgg ctc gcg gaa cgg acc ccg tcc ggg cag ggc ggg tca<br>Val His Gly Trp Leu Ala Glu Arg Thr Pro Ser Gly Gln Gly Gly Ser<br>          4605                      4610                  4615 | 13876 |
| ccg tcc cgc gcg gcg ggg aga gag gag agg ccg tgaacacggc agccggcccg<br>Pro Ser Arg Ala Ala Gly Arg Glu Glu Arg Pro<br>4620                      4625                  4630 | 13929 |
| accggcaccg ccgccggcgg caccaccgcc ccggcggcgg cacacgacct gtcccgcgcc | 13989 |
| ggacgcaggc tccaactcac ccgggccgca cagtggttcg ccggcaacca gggagacccc | 14049 |
| tacgggatga tcctgcgcgc cggcaccgcc gacccggcac cgtacgagga agagatcccc | 14109 |
| gggtaccgag ctcgaattct taattaagga ggtcgtagat gagtaacaag aacaacgatg | 14169 |
| agctgcagcg gcaggcctcg gaaaacaccc tggggctgaa cccggtcatc ggtatccgcc | 14229 |
| gcaaagacct gttgagctcg gcacgcaccg tgctgcgcca ggccgtgcgc caaccgctgc | 14289 |
| acagcgccaa gcatgtggcc cactttggcc tggagctgaa gaacgtgctg ctgggcaagt | 14349 |
| ccagccttgc cccggaaagc gacgaccgtc gcttcaatga cccggcatgg agcaacaacc | 14409 |
| cactttaccg ccgctacctg caaacctatc tggcctggcg caaggagctg caggactgga | 14469 |
| tcggcaacag cgacctgtcg ccccaggaca tcagccgcgg ccagttcgtc atcaacctga | 14529 |
| tgaccgaagc catggctccg accaacaccc tgtccaaccc ggcagcagtc aaacgcttct | 14589 |
| tcgaaaccgg cggcaagagc ctgctcgatg gcctgtccaa cctggccaag gacctggtca | 14649 |
| acaacggtgg catgcccagc caggtgaaca tggacgcctt cgaggtgggc aagaacctgg | 14709 |
| gcaccagtga aggcgccgtg gtgtaccgca acgatgtgct ggagctgatc cagtacaagc | 14769 |
| ccatcaccga gcaggtgcat gcccgcccgc tgctggtggt gccgccgcag atcaacaagt | 14829 |
| tctacgtatt cgacctgagc ccggaaaaga gcctggcacg ctactgcctg cgctcgcagc | 14889 |
| agcagacctt catcatcagc tggcgcaacc cgaccaaagc ccagcgcgaa tggggcctgt | 14949 |
| ccacctacat cgacgcgctc aaggaggcgg tcgacgcggt gctggcgatt accggcagca | 15009 |
| aggacctgaa catgctcggt gcctgctccg gcggcatcac ctgcacggca ttggtcggcc | 15069 |
| actatgccgc cctcggcgaa aacaaggtca atgcccctgac cctgctggtc agcgtgctgg | 15129 |
| acaccaccat ggacaaccag gtcgccctgt tcgtcgacga gcagactttg gaggccgcca | 15189 |
| agcgccactc ctaccaggcc ggtgtgctcg aaggcagcga gatggccaag gtgttcgcct | 15249 |
| ggatgcgccc caacgacctg atctggaact actgggtcaa caactacctg ctcggcaacg | 15309 |
| agccgccggt gttcgacatc ctgttctgga caacgacac cacgcgcctg ccggccgcct | 15369 |
| tccacggcga cctgatcgaa atgttcaaga gcaacccgct gacccgcccg gacgccctgg | 15429 |
| aggtttgcgg cactccgatc gacctgaaac aggtcaaatg cgacatctac agccttgccg | 15489 |
| gcaccaacga ccacatcacc ccgtggcagt catgctaccg ctcggcgcac ctgttcggcg | 15549 |
| gcaagatcga gttcgtgctg tccaacagcg gccacatcca gagcatcctc aacccgccag | 15609 |
| gcaaccccaa ggcgcgcttc atgaccggtg ccgatcgccc gggtgacccg gtggcctggc | 15669 |
| aggaaaacgc caccaagcat gccgactcct ggtggctgca ctggcaaagc tggctgggcg | 15729 |
| agcgtgccgg cgagctggaa aaggcgccga cccgcctggg caaccgtgcc tatgccgctg | 15789 |
| gcgaggcatc cccgggcacc tacgttcacg agcgttgagc tgcagcgccg tggccacctg | 15849 |
| cgggacgcca cggtgttgaa ttc | 15872 |

```
<210> SEQ ID NO 2
<211> LENGTH: 4630
<212> TYPE: PRT
<213> ORGANISM: Streptomyces venezuelae

<400> SEQUENCE: 2

Met Asn Glu Ala Ile Ala Val Val Gly Met Ser Cys Arg Leu Pro Lys
 1               5                  10                  15

Ala Ser Asn Pro Ala Ala Phe Trp Glu Leu Leu Arg Asn Gly Glu Ser
            20                  25                  30

Ala Val Thr Asp Val Pro Ser Gly Arg Trp Thr Ser Val Leu Gly Gly
        35                  40                  45

Ala Asp Ala Glu Glu Pro Ala Glu Ser Gly Val Arg Arg Gly Gly Phe
    50                  55                  60

Leu Asp Ser Leu Asp Leu Phe Asp Ala Ala Phe Phe Gly Ile Ser Pro
65                  70                  75                  80

Arg Glu Ala Ala Ala Met Asp Pro Gln Gln Arg Leu Val Leu Glu Leu
                85                  90                  95

Ala Trp Glu Ala Leu Glu Asp Ala Gly Ile Val Pro Gly Thr Leu Ala
            100                 105                 110

Gly Ser Arg Thr Ala Val Phe Val Gly Thr Leu Arg Asp Asp Tyr Thr
        115                 120                 125

Ser Leu Leu Tyr Gln His Gly Glu Gln Ala Ile Thr Gln His Thr Met
    130                 135                 140

Ala Gly Val Asn Arg Gly Val Ile Ala Asn Arg Val Ser Tyr His Leu
145                 150                 155                 160

Gly Leu Gln Gly Pro Ser Leu Thr Val Asp Ala Ala Gln Ser Ser Ser
                165                 170                 175

Leu Val Ala Val His Leu Ala Cys Glu Ser Leu Arg Ala Gly Glu Ser
            180                 185                 190

Thr Thr Ala Leu Val Ala Gly Val Asn Leu Asn Ile Leu Ala Glu Ser
        195                 200                 205

Ala Val Thr Glu Glu Arg Phe Gly Gly Leu Ser Pro Asp Gly Thr Ala
    210                 215                 220

Tyr Thr Phe Asp Ala Arg Ala Asn Gly Phe Val Arg Gly Glu Gly Gly
225                 230                 235                 240

Gly Val Val Leu Lys Pro Leu Ser Arg Ala Leu Ala Asp Gly Asp
                245                 250                 255

Arg Val His Gly Val Ile Arg Ala Ser Ala Val Asn Asn Asp Gly Ala
            260                 265                 270

Thr Pro Gly Leu Thr Val Pro Ser Arg Ala Ala Gln Glu Lys Val Leu
        275                 280                 285

Arg Glu Ala Tyr Arg Lys Ala Ala Leu Asp Pro Ser Ala Val Gln Tyr
    290                 295                 300

Val Glu Leu His Gly Thr Gly Thr Pro Val Gly Asp Pro Ile Glu Ala
305                 310                 315                 320

Ala Ala Leu Gly Ala Val Leu Gly Ser Ala Arg Pro Ala Asp Glu Pro
                325                 330                 335

Leu Leu Val Gly Ser Ala Lys Thr Asn Val Gly His Leu Glu Gly Ala
            340                 345                 350

Ala Gly Ile Val Gly Leu Ile Lys Thr Leu Leu Ala Leu Gly Arg Arg
        355                 360                 365

Arg Ile Pro Ala Ser Leu Asn Phe Arg Thr Pro His Pro Asp Ile Pro
    370                 375                 380
```

```
Leu Asp Thr Leu Gly Leu Asp Val Pro Asp Gly Leu Arg Glu Trp Pro
385                 390                 395                 400

His Pro Asp Arg Glu Leu Leu Ala Gly Val Ser Ser Phe Gly Met Gly
                405                 410                 415

Gly Thr Asn Ala His Val Val Leu Ser Glu Gly Pro Ala Gln Gly Gly
            420                 425                 430

Glu Gln Pro Gly Ile Asp Glu Glu Thr Pro Val Asp Ser Gly Ala Ala
                435                 440                 445

Leu Pro Phe Val Val Thr Gly Arg Gly Gly Glu Ala Leu Arg Ala Gln
        450                 455                 460

Ala Arg Arg Leu His Glu Ala Val Glu Ala Asp Pro Glu Leu Ala Pro
465                 470                 475                 480

Ala Ala Leu Ala Arg Ser Leu Val Thr Thr Arg Thr Val Phe Thr His
                485                 490                 495

Arg Ser Val Val Leu Ala Pro Asp Arg Ala Arg Leu Leu Asp Gly Leu
                500                 505                 510

Gly Ala Leu Ala Ala Gly Thr Pro Ala Pro Gly Val Val Thr Gly Thr
            515                 520                 525

Pro Ala Pro Gly Arg Leu Ala Val Leu Phe Ser Gly Gln Gly Ala Gln
        530                 535                 540

Arg Thr Gly Met Gly Met Glu Leu Tyr Ala Ala His Pro Ala Phe Ala
545                 550                 555                 560

Thr Ala Phe Asp Ala Val Ala Ala Glu Leu Asp Pro Leu Leu Asp Arg
                565                 570                 575

Pro Leu Ala Glu Leu Val Ala Ala Gly Asp Thr Leu Asp Arg Thr Val
            580                 585                 590

His Thr Gln Pro Ala Leu Phe Ala Val Glu Val Ala Leu His Arg Leu
        595                 600                 605

Val Glu Ser Trp Gly Val Thr Pro Asp Leu Leu Ala Gly His Ser Val
            610                 615                 620

Gly Glu Ile Ser Ala Ala His Val Ala Gly Val Leu Ser Leu Arg Asp
625                 630                 635                 640

Ala Ala Arg Leu Val Ala Ala Arg Gly Arg Leu Met Gln Ala Leu Pro
                645                 650                 655

Glu Gly Gly Ala Met Val Ala Val Glu Ala Ser Glu Glu Glu Val Leu
            660                 665                 670

Pro His Leu Ala Gly Arg Glu Arg Glu Leu Ser Leu Ala Ala Val Asn
        675                 680                 685

Gly Pro Arg Ala Val Val Leu Ala Gly Ala Glu Arg Ala Val Leu Asp
    690                 695                 700

Val Ala Glu Leu Leu Arg Glu Gln Gly Arg Arg Thr Lys Arg Leu Ser
705                 710                 715                 720

Val Ser His Ala Phe His Ser Pro Leu Met Glu Pro Met Leu Asp Asp
                725                 730                 735

Phe Arg Arg Val Val Glu Glu Leu Asp Phe Gln Glu Pro Arg Val Asp
            740                 745                 750

Val Val Ser Thr Val Thr Gly Leu Pro Val Thr Ala Gly Gln Trp Thr
        755                 760                 765

Asp Pro Glu Tyr Trp Val Asp Gln Val Arg Arg Pro Val Arg Phe Leu
    770                 775                 780

Asp Ala Val Arg Thr Leu Glu Glu Ser Gly Ala Asp Thr Phe Leu Glu
785                 790                 795                 800

Leu Gly Pro Asp Gly Val Cys Ser Ala Met Ala Ala Asp Ser Val Arg
```

-continued

```
                805                 810                 815
Asp Gln Glu Ala Ala Thr Ala Val Ser Ala Leu Arg Lys Gly Arg Pro
                820                 825                 830
Glu Pro Gln Ser Leu Leu Ala Ala Leu Thr Thr Val Phe Val Arg Gly
                835                 840                 845
His Asp Val Asp Trp Thr Ala Ala His Gly Ser Thr Gly Thr Val Arg
                850                 855                 860
Val Pro Leu Pro Thr Tyr Ala Phe Gln Arg Glu Arg His Trp Phe Asp
865                 870                 875                 880
Gly Ala Ala Arg Thr Ala Ala Pro Leu Thr Ala Gly Arg Ser Gly Thr
                885                 890                 895
Gly Ala Gly Thr Gly Pro Ala Ala Gly Val Thr Ser Gly Glu Gly Glu
                900                 905                 910
Gly Glu Gly Glu Gly Ala Gly Ala Gly Gly Asp Arg Pro Ala Arg
                915                 920                 925
His Glu Thr Thr Glu Arg Val Arg Ala His Val Ala Ala Val Leu Glu
                930                 935                 940
Tyr Asp Asp Pro Thr Arg Val Glu Leu Gly Leu Thr Phe Lys Glu Leu
945                 950                 955                 960
Gly Phe Asp Ser Leu Met Ser Val Glu Leu Arg Asn Ala Leu Val Asp
                965                 970                 975
Asp Thr Gly Leu Arg Leu Pro Ser Gly Leu Leu Phe Asp His Pro Thr
                980                 985                 990
Pro Arg Ala Leu Ala Ala His Leu Gly Asp Leu Leu Thr Gly Gly Ser
                995                 1000                1005
Gly Glu Thr Gly Ser Ala Asp Gly Ile Pro Pro Ala Thr Pro Ala Asp
        1010                1015                1020
Thr Thr Ala Glu Pro Ile Ala Ile Gly Met Ala Cys Arg Tyr Pro
1025                1030                1035                1040
Gly Gly Val Thr Ser Pro Glu Asp Leu Trp Arg Leu Val Ala Glu Gly
                1045                1050                1055
Arg Asp Ala Val Ser Gly Leu Pro Thr Asp Arg Gly Trp Asp Glu Asp
                1060                1065                1070
Leu Phe Asp Ala Asp Pro Asp Arg Ser Gly Lys Ser Ser Val Arg Glu
                1075                1080                1085
Gly Gly Phe Leu His Asp Ala Ala Leu Phe Asp Ala Gly Phe Phe Gly
        1090                1095                1100
Ile Ser Pro Arg Glu Ala Leu Gly Met Asp Pro Gln Gln Arg Leu Leu
1105                1110                1115                1120
Leu Glu Thr Ala Trp Glu Ala Val Glu Arg Ala Gly Leu Asp Pro Glu
                1125                1130                1135
Gly Leu Lys Gly Ser Arg Thr Ala Val Phe Val Gly Ala Thr Ala Leu
                1140                1145                1150
Asp Tyr Gly Pro Arg Met His Asp Gly Ala Glu Gly Val Glu Gly His
                1155                1160                1165
Leu Leu Thr Gly Thr Thr Pro Ser Val Met Ser Gly Arg Ile Ala Tyr
        1170                1175                1180
Gln Leu Gly Leu Thr Gly Pro Ala Val Thr Val Asp Thr Ala Cys Ser
1185                1190                1195                1200
Ser Ser Leu Val Ala Leu His Leu Ala Val Arg Ser Leu Arg Gln Gly
                1205                1210                1215
Glu Ser Ser Leu Ala Leu Ala Gly Gly Ala Thr Val Met Ser Thr Pro
                1220                1225                1230
```

-continued

```
Gly Met Phe Val Glu Phe Ser Arg Gln Arg Gly Leu Ala Ala Asp Gly
        1235                1240                1245

Arg Ser Lys Ala Phe Ser Asp Ser Ala Asp Gly Thr Ser Trp Ala Glu
        1250                1255                1260

Gly Val Gly Leu Leu Val Val Glu Arg Leu Ser Asp Ala Glu Arg Asn
1265            1270                1275                    1280

Gly His Pro Val Leu Ala Val Ile Arg Gly Ser Ala Val Asn Gln Asp
                1285                1290                1295

Gly Ala Ser Asn Gly Leu Thr Ala Pro Asn Gly Pro Ser Gln Gln Arg
            1300                1305                1310

Val Ile Arg Gln Ala Leu Ala Asp Ala Gly Leu Thr Pro Ala Asp Val
        1315                1320                1325

Asp Ala Val Glu Ala His Gly Thr Gly Thr Arg Leu Gly Asp Pro Ile
        1330                1335                1340

Glu Ala Glu Ala Ile Leu Gly Thr Tyr Gly Arg Asp Arg Gly Glu Gly
1345            1350                1355                    1360

Ala Pro Leu Gln Leu Gly Ser Leu Lys Ser Asn Ile Gly His Ala Gln
                1365                1370                1375

Ala Ala Ala Gly Val Gly Gly Leu Ile Lys Met Val Leu Ala Met Arg
            1380                1385                1390

His Gly Val Leu Pro Arg Thr Leu His Val Asp Arg Pro Thr Thr Arg
        1395                1400                1405

Val Asp Trp Glu Ala Gly Gly Val Glu Leu Leu Thr Glu Glu Arg Glu
        1410                1415                1420

Trp Pro Glu Thr Gly Arg Pro Arg Arg Ala Ala Ile Ser Ser Phe Gly
1425            1430                1435                    1440

Ile Ser Gly Thr Asn Ala His Ile Val Val Glu Gln Ala Pro Glu Ala
                1445                1450                1455

Gly Glu Ala Ala Val Thr Thr Thr Ala Pro Glu Ala Gly Glu Ala Gly
            1460                1465                1470

Glu Ala Ala Asp Thr Thr Ala Thr Thr Thr Pro Ala Ala Val Gly Val
        1475                1480                1485

Pro Glu Pro Val Arg Ala Pro Val Val Ser Ala Arg Asp Ala Ala
        1490                1495                1500

Ala Leu Arg Ala Gln Ala Val Arg Leu Arg Thr Phe Leu Asp Gly Arg
1505            1510                1515                    1520

Pro Asp Val Thr Val Ala Asp Leu Gly Arg Ser Leu Ala Ala Arg Thr
                1525                1530                1535

Ala Phe Glu His Lys Ala Ala Leu Thr Thr Ala Thr Arg Asp Glu Leu
            1540                1545                1550

Leu Ala Gly Leu Asp Ala Leu Gly Arg Gly Glu Gln Ala Thr Gly Leu
        1555                1560                1565

Val Thr Gly Glu Pro Ala Arg Ala Gly Arg Thr Ala Phe Leu Phe Thr
        1570                1575                1580

Gly Gln Gly Ala Gln Arg Val Ala Met Gly Glu Glu Leu Arg Ala Ala
1585            1590                1595                    1600

His Pro Val Phe Ala Ala Ala Leu Asp Thr Val Tyr Ala Ala Leu Asp
                1605                1610                1615

Arg His Leu Asp Arg Pro Leu Arg Glu Ile Val Ala Ala Gly Glu Glu
            1620                1625                1630

Leu Asp Leu Thr Ala Tyr Thr Gln Pro Ala Leu Phe Ala Phe Glu Val
        1635                1640                1645
```

```
Ala Leu Phe Arg Leu Leu Glu His His Gly Leu Val Pro Asp Leu Leu
        1650                1655                1660

Thr Gly His Ser Val Gly Glu Ile Ala Ala His Val Ala Gly Val
1665            1670                1675                1680

Leu Ser Leu Asp Asp Ala Ala Arg Leu Val Thr Ala Arg Gly Arg Leu
                1685                1690                1695

Met Gln Ser Ala Arg Glu Gly Gly Ala Met Ile Ala Val Gln Ala Gly
            1700                1705                1710

Glu Ala Glu Val Val Glu Ser Leu Lys Gly Tyr Glu Gly Arg Val Ala
            1715                1720                1725

Val Ala Ala Val Asn Gly Pro Thr Ala Val Val Ser Gly Asp Ala
        1730                1735                1740

Asp Ala Ala Glu Glu Ile Arg Ala Val Trp Ala Gly Arg Gly Arg Arg
1745                1750                1755                1760

Thr Arg Arg Leu Arg Val Ser His Ala Phe His Ser Pro His Met Asp
                1765                1770                1775

Asp Val Leu Asp Glu Phe Leu Arg Val Ala Glu Gly Leu Thr Phe Glu
                1780                1785                1790

Glu Pro Arg Ile Pro Val Val Ser Thr Val Thr Gly Ala Leu Val Thr
        1795                1800                1805

Ser Gly Glu Leu Thr Ser Pro Ala Tyr Trp Val Asp Gln Ile Arg Arg
        1810                1815                1820

Pro Val Arg Phe Leu Asp Ala Val Arg Thr Leu Ala Ala Gln Asp Ala
1825                1830                1835                1840

Thr Val Leu Val Glu Ile Gly Pro Asp Ala Val Leu Thr Ala Leu Ala
                1845                1850                1855

Glu Glu Ala Leu Ala Pro Gly Thr Asp Ala Pro Asp Ala Arg Asp Val
            1860                1865                1870

Thr Val Val Pro Leu Leu Arg Ala Gly Arg Pro Glu Pro Glu Thr Leu
        1875                1880                1885

Ala Ala Gly Leu Ala Thr Ala His Val His Gly Ala Pro Leu Asp Arg
        1890                1895                1900

Ala Ser Phe Phe Pro Asp Gly Arg Arg Thr Asp Leu Pro Thr Tyr Ala
1905                1910                1915                1920

Phe Arg Arg Glu His Tyr Trp Leu Thr Pro Glu Ala Arg Thr Asp Ala
                1925                1930                1935

Arg Ala Leu Gly Phe Asp Pro Ala Arg His Pro Leu Leu Thr Thr Thr
                1940                1945                1950

Val Glu Val Ala Gly Gly Asp Gly Val Leu Leu Thr Gly Arg Leu Ser
            1955                1960                1965

Leu Thr Asp Gln Pro Trp Leu Ala Asp His Met Val Asn Gly Ala Val
        1970                1975                1980

Leu Leu Pro Ala Thr Ala Phe Leu Glu Leu Ala Leu Ala Ala Gly Asp
1985                1990                1995                2000

His Val Gly Ala Val Arg Val Glu Glu Leu Thr Leu Glu Ala Pro Leu
                2005                2010                2015

Val Leu Pro Glu Arg Gly Ala Val Arg Ile Gln Val Gly Val Ser Gly
        2020                2025                2030

Asp Gly Glu Ser Pro Ala Gly Arg Thr Phe Gly Val Tyr Ser Thr Pro
        2035                2040                2045

Asp Ser Gly Asp Thr Gly Asp Asp Ala Pro Arg Glu Trp Thr Arg His
        2050                2055                2060

Val Ser Gly Val Leu Gly Glu Gly Asp Pro Ala Thr Glu Ser Asp His
```

-continued

```
         2065                2070                2075                2080
Pro Gly Thr Asp Gly Asp Gly Ser Ala Ala Trp Pro Ala Ala Ala
                     2085                2090                2095

Thr Ala Thr Pro Leu Asp Gly Val Tyr Asp Arg Leu Ala Glu Leu Gly
            2100                2105                2110

Tyr Gly Tyr Gly Pro Ala Phe Gln Gly Leu Thr Gly Leu Trp Arg Asp
        2115                2120                2125

Gly Ala Asp Thr Leu Ala Glu Ile Arg Leu Pro Ala Ala Gln His Glu
    2130                2135                2140

Ser Ala Gly Leu Phe Gly Val His Pro Ala Leu Leu Asp Ala Ala Leu
2145                2150                2155                2160

His Pro Ile Val Leu Glu Gly Asn Ser Ala Ala Gly Ala Cys Asp Ala
            2165                2170                2175

Asp Thr Asp Ala Thr Asp Arg Ile Arg Leu Pro Phe Ala Trp Ala Gly
        2180                2185                2190

Val Thr Leu His Ala Glu Gly Ala Thr Ala Leu Arg Val Arg Ile Thr
    2195                2200                2205

Pro Thr Gly Pro Asp Thr Val Thr Leu Arg Leu Thr Asp Thr Thr Gly
    2210                2215                2220

Ala Pro Val Ala Thr Val Glu Ser Leu Thr Leu Arg Ala Val Ala Lys
2225                2230                2235                2240

Asp Arg Leu Gly Thr Thr Ala Gly Arg Val Asp Asp Ala Leu Phe Thr
            2245                2250                2255

Val Val Trp Thr Glu Thr Gly Thr Pro Glu Pro Ala Gly Arg Gly Ala
        2260                2265                2270

Val Glu Val Glu Glu Leu Val Asp Leu Ala Gly Leu Gly Asp Leu Val
    2275                2280                2285

Glu Leu Gly Ala Ala Asp Val Val Leu Arg Ala Asp Arg Trp Thr Leu
    2290                2295                2300

Asp Gly Asp Pro Ser Ala Ala Arg Thr Ala Val Arg Arg Thr Leu
2305                2310                2315                2320

Ala Ile Val Gln Glu Phe Leu Ser Glu Pro Arg Phe Asp Gly Ser Arg
            2325                2330                2335

Leu Val Cys Val Thr Arg Gly Ala Val Ala Ala Leu Pro Gly Glu Asp
        2340                2345                2350

Val Thr Ser Leu Ala Thr Gly Pro Leu Trp Gly Leu Val Arg Ser Ala
    2355                2360                2365

Gln Ser Glu Asn Pro Gly Arg Leu Phe Leu Leu Asp Leu Gly Glu Gly
    2370                2375                2380

Glu Gly Glu Arg Asp Gly Ala Glu Glu Leu Ile Arg Ala Ala Thr Ala
2385                2390                2395                2400

Gly Asp Glu Pro Gln Leu Ala Ala Arg Asp Gly Arg Leu Leu Ala Pro
            2405                2410                2415

Arg Leu Ala Arg Thr Ala Ala Leu Ser Ser Glu Asp Thr Ala Gly Gly
        2420                2425                2430

Ala Asp Arg Phe Gly Pro Asp Gly Thr Val Leu Val Thr Gly Gly Thr
    2435                2440                2445

Gly Gly Leu Gly Ala Leu Leu Ala Arg His Leu Val Glu Arg His Gly
    2450                2455                2460

Val Arg Arg Leu Leu Leu Val Ser Arg Arg Gly Ala Asp Ala Pro Gly
2465                2470                2475                2480

Ala Ala Asp Leu Gly Glu Asp Leu Ala Gly Leu Gly Ala Glu Val Ala
            2485                2490                2495
```

```
Phe Ala Ala Ala Asp Ala Ala Asp Arg Glu Ser Leu Ala Arg Ala Ile
            2500                2505                2510
Ala Thr Val Pro Ala Glu His Pro Leu Thr Ala Val His Thr Ala
        2515                2520                2525
Gly Val Val Asp Asp Ala Thr Val Glu Ala Leu Thr Pro Glu Arg Leu
    2530                2535                2540
Asp Ala Val Leu Arg Pro Lys Val Asp Ala Ala Trp Asn Leu His Glu
2545                2550                2555                2560
Leu Thr Lys Asp Leu Arg Leu Asp Ala Phe Val Leu Phe Ser Ser Val
                2565                2570                2575
Ser Gly Ile Val Gly Thr Ala Gly Gln Ala Asn Tyr Ala Ala Ala Asn
            2580                2585                2590
Thr Gly Leu Asp Ala Leu Ala Ala His Arg Ala Ala Thr Gly Leu Ala
        2595                2600                2605
Ala Thr Ser Leu Ala Trp Gly Leu Trp Asp Gly Thr His Gly Met Gly
    2610                2615                2620
Gly Thr Leu Gly Ala Ala Asp Leu Ala Arg Trp Ser Arg Ala Gly Ile
2625                2630                2635                2640
Thr Pro Leu Thr Pro Leu Gln Gly Leu Ala Leu Phe Asp Ala Ala Val
                2645                2650                2655
Ala Arg Asp Asp Ala Leu Leu Val Pro Ala Gly Leu Arg Pro Thr Ala
            2660                2665                2670
His Arg Gly Thr Asp Gly Gln Pro Pro Ala Leu Trp Arg Gly Leu Val
        2675                2680                2685
Arg Ala Arg Pro Arg Arg Ala Ala Arg Thr Ala Ala Glu Ala Ala Asp
    2690                2695                2700
Thr Thr Gly Gly Trp Leu Ser Gly Leu Ala Ala Gln Ser Pro Glu Glu
2705                2710                2715                2720
Arg Arg Ser Thr Ala Val Thr Leu Val Thr Gly Val Val Ala Asp Val
                2725                2730                2735
Leu Gly His Ala Asp Ser Ala Ala Val Gly Ala Glu Arg Ser Phe Lys
            2740                2745                2750
Asp Leu Gly Phe Asp Ser Leu Ala Gly Val Glu Leu Arg Asn Arg Leu
        2755                2760                2765
Asn Ala Ala Thr Gly Leu Arg Leu Pro Ala Thr Thr Val Phe Asp His
    2770                2775                2780
Pro Ser Pro Ala Ala Leu Ala Ser His Leu Leu Ala Gln Val Pro Gly
2785                2790                2795                2800
Leu Lys Glu Gly Thr Ala Ala Thr Ala Thr Val Val Ala Glu Arg Gly
                2805                2810                2815
Ala Ser Phe Gly Asp Arg Ala Thr Asp Asp Pro Ile Ala Ile Val
            2820                2825                2830
Gly Met Ala Cys Arg Tyr Pro Gly Gly Val Ser Ser Pro Glu Asp Leu
        2835                2840                2845
Trp Arg Leu Val Ala Glu Gly Thr Asp Ala Ile Ser Glu Phe Pro Val
    2850                2855                2860
Asn Arg Gly Trp Asp Leu Glu Ser Leu Tyr Asp Pro Asp Pro Glu Ser
2865                2870                2875                2880
Lys Gly Thr Thr Tyr Cys Arg Glu Gly Gly Phe Leu Glu Gly Ala Gly
                2885                2890                2895
Asp Phe Asp Ala Ala Phe Phe Gly Ile Ser Pro Arg Glu Ala Leu Val
            2900                2905                2910
```

-continued

```
Met Asp Pro Gln Gln Arg Leu Leu Leu Glu Val Ser Trp Glu Ala Leu
            2915                2920                2925

Glu Arg Ala Gly Ile Asp Pro Ser Ser Leu Arg Gly Ser Arg Gly Gly
            2930                2935                2940

Val Tyr Val Gly Ala Ala His Gly Ser Tyr Ala Ser Asp Pro Arg Leu
2945                2950                2955                2960

Val Pro Glu Gly Ser Glu Gly Tyr Leu Leu Thr Gly Ser Ala Asp Ala
            2965                2970                2975

Val Met Ser Gly Arg Ile Ser Tyr Ala Leu Gly Leu Glu Gly Pro Ser
            2980                2985                2990

Met Thr Val Glu Thr Ala Cys Ser Ser Leu Val Ala Leu His Leu
            2995                3000                3005

Ala Val Arg Ala Leu Arg His Gly Glu Cys Gly Leu Ala Leu Ala Gly
            3010                3015                3020

Gly Val Ala Val Met Ala Asp Pro Ala Ala Phe Val Glu Phe Ser Arg
3025                3030                3035                3040

Gln Lys Gly Leu Ala Ala Asp Gly Arg Cys Lys Ala Phe Ser Ala Ala
            3045                3050                3055

Ala Asp Gly Thr Gly Trp Ala Glu Gly Val Gly Val Leu Val Leu Glu
            3060                3065                3070

Arg Leu Ser Asp Ala Arg Arg Ala Gly His Thr Val Leu Gly Leu Val
            3075                3080                3085

Thr Gly Thr Ala Val Asn Gln Asp Gly Ala Ser Asn Gly Leu Thr Ala
            3090                3095                3100

Pro Asn Gly Pro Ala Gln Gln Arg Val Ile Ala Glu Ala Leu Ala Asp
3105                3110                3115                3120

Ala Gly Leu Ser Pro Glu Asp Val Asp Ala Val Glu Ala His Gly Thr
            3125                3130                3135

Gly Thr Arg Leu Gly Asp Pro Ile Glu Ala Gly Ala Leu Leu Ala Ala
            3140                3145                3150

Ser Gly Arg Asn Arg Ser Gly Asp His Pro Leu Trp Leu Gly Ser Leu
            3155                3160                3165

Lys Ser Asn Ile Gly His Ala Gln Ala Ala Gly Val Gly Gly Val
            3170                3175                3180

Ile Lys Met Leu Gln Ala Leu Arg His Gly Leu Leu Pro Arg Thr Leu
3185                3190                3195                3200

His Ala Asp Glu Pro Thr Pro His Ala Asp Trp Ser Ser Gly Arg Val
            3205                3210                3215

Arg Leu Leu Thr Ser Glu Val Pro Trp Gln Arg Thr Gly Arg Pro Arg
            3220                3225                3230

Arg Thr Gly Val Ser Ala Phe Gly Val Gly Gly Thr Asn Ala His Val
            3235                3240                3245

Val Leu Glu Glu Ala Pro Ala Pro Pro Ala Pro Glu Pro Ala Gly Glu
            3250                3255                3260

Ala Pro Gly Gly Ser Arg Ala Ala Glu Gly Ala Glu Gly Pro Leu Ala
3265                3270                3275                3280

Trp Val Val Ser Gly Arg Asp Glu Pro Ala Leu Arg Ser Gln Ala Arg
            3285                3290                3295

Arg Leu Arg Asp His Leu Ser Arg Thr Pro Gly Ala Arg Pro Arg Asp
            3300                3305                3310

Ile Ala Phe Ser Leu Ala Ala Thr Arg Ala Ala Phe Asp His Arg Ala
            3315                3320                3325

Val Leu Ile Gly Ser Asp Gly Ala Glu Leu Ala Ala Ala Leu Asp Ala
```

-continued

```
          3330                3335                3340
Leu Ala Glu Gly Arg Asp Gly Pro Ala Val Val Arg Gly Val Arg Asp
3345                3350                3355                3360
Arg Asp Gly Arg Met Ala Phe Leu Phe Thr Gly Gln Gly Ser Gln Arg
                3365                3370                3375
Ala Gly Met Ala His Asp Leu His Ala Ala His Thr Phe Phe Ala Ser
            3380                3385                3390
Ala Leu Asp Glu Val Thr Asp Arg Leu Asp Pro Leu Leu Gly Arg Pro
        3395                3400                3405
Leu Gly Ala Leu Leu Asp Ala Arg Pro Gly Ser Pro Glu Ala Ala Leu
    3410                3415                3420
Leu Asp Arg Thr Glu Tyr Thr Gln Pro Ala Leu Phe Ala Val Glu Val
3425                3430                3435                3440
Ala Leu His Arg Leu Leu Glu His Trp Gly Met Arg Pro Asp Leu Leu
                3445                3450                3455
Leu Gly His Ser Val Gly Glu Leu Ala Ala Ala His Val Ala Gly Val
            3460                3465                3470
Leu Asp Leu Asp Asp Ala Cys Ala Leu Val Ala Ala Arg Gly Arg Leu
        3475                3480                3485
Met Gln Arg Leu Pro Pro Gly Gly Ala Met Val Ser Val Arg Ala Gly
    3490                3495                3500
Glu Asp Glu Val Arg Ala Leu Leu Ala Gly Arg Glu Asp Ala Val Cys
3505                3510                3515                3520
Val Ala Ala Val Asn Gly Pro Arg Ser Val Val Ile Ser Gly Ala Glu
                3525                3530                3535
Glu Ala Val Ala Glu Ala Ala Gln Leu Ala Gly Arg Gly Arg Arg
            3540                3545                3550
Thr Arg Arg Leu Arg Val Ala His Ala Phe His Ser Pro Leu Met Asp
        3555                3560                3565
Gly Met Leu Ala Gly Phe Arg Glu Val Ala Ala Gly Leu Arg Tyr Arg
    3570                3575                3580
Glu Pro Glu Leu Thr Val Val Ser Thr Val Thr Gly Arg Pro Ala Arg
3585                3590                3595                3600
Pro Gly Glu Leu Thr Gly Pro Asp Tyr Trp Val Ala Gln Val Arg Glu
                3605                3610                3615
Pro Val Arg Phe Ala Asp Ala Val Arg Thr Ala His Arg Leu Gly Ala
            3620                3625                3630
Arg Thr Phe Leu Glu Thr Gly Pro Asp Gly Val Leu Cys Gly Met Ala
        3635                3640                3645
Glu Glu Cys Leu Glu Asp Thr Val Ala Leu Leu Pro Ala Ile His
    3650                3655                3660
Lys Pro Gly Thr Ala Pro His Gly Pro Ala Ala Pro Gly Ala Leu Arg
3665                3670                3675                3680
Ala Ala Ala Ala Ala Tyr Gly Arg Gly Ala Arg Val Asp Trp Ala Gly
                3685                3690                3695
Met His Ala Asp Gly Pro Glu Gly Pro Ala Arg Arg Val Glu Leu Pro
            3700                3705                3710
Val His Ala Phe Arg His Arg Arg Tyr Trp Leu Ala Pro Gly Arg Ala
        3715                3720                3725
Ala Asp Thr Asp Asp Trp Met Tyr Arg Ile Gly Trp Asp Arg Leu Pro
    3730                3735                3740
Ala Val Thr Gly Gly Ala Arg Thr Ala Gly Arg Trp Leu Val Ile His
3745                3750                3755                3760
```

-continued

```
Pro Asp Ser Pro Arg Cys Arg Glu Leu Ser Gly His Ala Glu Arg Ala
            3765                3770                3775
Leu Arg Ala Ala Gly Ala Ser Pro Val Pro Leu Pro Val Asp Ala Pro
            3780                3785                3790
Ala Ala Asp Arg Ala Ser Phe Ala Ala Leu Leu Arg Ser Ala Thr Gly
            3795                3800                3805
Pro Asp Thr Arg Gly Asp Thr Ala Ala Pro Val Ala Gly Val Leu Ser
            3810                3815                3820
Leu Leu Ser Glu Glu Asp Arg Pro His Arg Gln His Ala Pro Val Pro
3825                3830                3835                3840
Ala Gly Val Leu Ala Thr Leu Ser Leu Met Gln Ala Met Glu Glu Glu
            3845                3850                3855
Ala Val Glu Ala Arg Val Trp Cys Val Ser Arg Ala Ala Val Ala Ala
            3860                3865                3870
Ala Asp Arg Glu Arg Pro Val Gly Ala Gly Ala Ala Leu Trp Gly Leu
            3875                3880                3885
Gly Arg Val Ala Ala Leu Glu Arg Pro Thr Arg Trp Gly Gly Leu Val
            3890                3895                3900
Asp Leu Pro Ala Ser Pro Gly Ala Ala His Trp Ala Ala Ala Val Glu
3905                3910                3915                3920
Arg Leu Ala Gly Pro Glu Asp Gln Ile Ala Val Arg Ala Ser Gly Ser
            3925                3930                3935
Trp Gly Arg Arg Leu Thr Arg Leu Pro Arg Asp Gly Gly Gly Arg Thr
            3940                3945                3950
Ala Ala Pro Ala Tyr Arg Pro Arg Gly Thr Val Leu Val Thr Gly Gly
            3955                3960                3965
Thr Gly Ala Leu Gly Gly His Leu Ala Arg Trp Leu Ala Ala Ala Gly
            3970                3975                3980
Ala Glu His Leu Ala Leu Thr Ser Arg Arg Gly Pro Asp Ala Pro Gly
3985                3990                3995                4000
Ala Ala Gly Leu Glu Ala Glu Leu Leu Leu Leu Gly Ala Lys Val Thr
            4005                4010                4015
Phe Ala Ala Cys Asp Thr Ala Asp Arg Asp Gly Leu Ala Arg Val Leu
            4020                4025                4030
Arg Ala Ile Pro Glu Asp Thr Pro Leu Thr Ala Val Phe His Ala Ala
            4035                4040                4045
Gly Val Pro Gln Val Thr Pro Leu Ser Arg Thr Ser Pro Glu His Phe
            4050                4055                4060
Ala Asp Val Tyr Ala Gly Lys Ala Ala Gly Ala Ala His Leu Asp Glu
4065                4070                4075                4080
Leu Thr Arg Glu Leu Gly Ala Gly Leu Asp Ala Phe Val Leu Tyr Ser
            4085                4090                4095
Ser Gly Ala Gly Val Trp Gly Ser Ala Gly Gln Gly Ala Tyr Ala Ala
            4100                4105                4110
Ala Asn Ala Ala Leu Asp Ala Leu Ala Arg Arg Arg Ala Ala Asp Gly
            4115                4120                4125
Leu Pro Ala Thr Ser Ile Ala Trp Gly Val Trp Gly Gly Gly Gly Met
            4130                4135                4140
Gly Ala Asp Glu Ala Gly Ala Glu Tyr Leu Gly Arg Arg Gly Met Arg
4145                4150                4155                4160
Pro Met Ala Pro Val Ser Ala Leu Arg Ala Met Ala Thr Ala Ile Ala
            4165                4170                4175
```

-continued

```
Ser Gly Glu Pro Cys Pro Thr Val Thr His Thr Asp Trp Glu Arg Phe
            4180                4185                4190
Gly Glu Gly Phe Thr Ala Phe Arg Pro Ser Pro Leu Ile Ala Gly Leu
            4195                4200                4205
Gly Thr Pro Gly Gly Gly Arg Ala Ala Glu Thr Pro Glu Glu Gly Asn
            4210                4215                4220
Ala Thr Ala Ala Ala Asp Leu Thr Ala Leu Pro Pro Ala Glu Leu Arg
4225                4230                4235                4240
Thr Ala Leu Arg Glu Leu Val Arg Ala Arg Thr Ala Ala Leu Gly
            4245                4250                4255
Leu Asp Asp Pro Ala Glu Val Ala Glu Gly Glu Arg Phe Pro Ala Met
            4260                4265                4270
Gly Phe Asp Ser Leu Ala Thr Val Arg Leu Arg Arg Gly Leu Ala Ser
            4275                4280                4285
Ala Thr Gly Leu Asp Leu Pro Pro Asp Leu Leu Phe Asp Arg Asp Thr
            4290                4295                4300
Pro Ala Ala Leu Ala Ala His Leu Ala Glu Leu Leu Ala Thr Ala Arg
4305                4310                4315                4320
Asp His Gly Pro Gly Gly Pro Gly Thr Gly Ala Ala Pro Ala Asp Ala
            4325                4330                4335
Gly Ser Gly Leu Pro Ala Leu Tyr Arg Glu Ala Val Arg Thr Gly Arg
            4340                4345                4350
Ala Ala Glu Met Ala Glu Leu Leu Ala Ala Ala Ser Arg Phe Arg Pro
            4355                4360                4365
Ala Phe Gly Thr Ala Asp Arg Gln Pro Val Ala Leu Val Pro Leu Ala
            4370                4375                4380
Asp Gly Ala Glu Asp Thr Gly Leu Pro Leu Leu Val Gly Cys Ala Gly
4385                4390                4395                4400
Thr Ala Val Ala Ser Gly Pro Val Glu Phe Thr Ala Phe Ala Gly Ala
            4405                4410                4415
Leu Ala Asp Leu Pro Ala Ala Pro Met Ala Ala Leu Pro Gln Pro
            4420                4425                4430
Gly Phe Leu Pro Gly Glu Arg Val Pro Ala Thr Pro Glu Ala Leu Phe
            4435                4440                4445
Glu Ala Gln Ala Glu Ala Leu Leu Arg Tyr Ala Ala Gly Arg Pro Phe
            4450                4455                4460
Val Leu Leu Gly His Ser Ala Gly Ala Asn Met Ala His Ala Leu Thr
4465                4470                4475                4480
Arg His Leu Glu Ala Asn Gly Gly Pro Ala Gly Leu Val Leu Met
            4485                4490                4495
Asp Ile Tyr Thr Pro Ala Asp Pro Gly Ala Met Gly Val Trp Arg Asn
            4500                4505                4510
Asp Met Phe Gln Trp Val Trp Arg Arg Ser Asp Ile Pro Pro Asp Asp
            4515                4520                4525
His Arg Leu Thr Ala Met Gly Ala Tyr His Arg Leu Leu Asp Trp
            4530                4535                4540
Ser Pro Thr Pro Val Arg Ala Pro Val Leu His Leu Arg Ala Ala Glu
4545                4550                4555                4560
Pro Met Gly Asp Trp Pro Pro Gly Asp Thr Gly Trp Gln Ser His Trp
            4565                4570                4575
Asp Gly Ala His Thr Thr Ala Gly Ile Pro Gly Asn His Phe Thr Met
            4580                4585                4590
Met Thr Glu His Ala Ser Ala Ala Ala Arg Leu Val His Gly Trp Leu
```

-continued

```
                4595                4600                4605
Ala Glu Arg Thr Pro Ser Gly Gln Gly Gly Ser Pro Ser Arg Ala Ala
        4610                4615                4620
Gly Arg Glu Glu Arg Pro
4625            4630

<210> SEQ ID NO 3
<211> LENGTH: 15872
<212> TYPE: DNA
<213> ORGANISM: Streptomyces venezuelae
<220> FEATURE:
<221> NAME/KEY: CDS
<222> LOCATION: (14148)...(15824)

<400> SEQUENCE: 3
ttaattaagg aggaccatca tgaacgaggc catcgccgtc gtcggcatgt cctgccgcct      60
gccgaaggcc tcgaacccgg ccgccttctg ggagctgctg cggaacgggg agagcgccgt    120
caccgacgtg ccctccggcc ggtggacgtc ggtgctcggg ggagcggacg ccgaggagcc    180
ggcggagtcc ggtgtccgcc ggggcggctt cctcgactcc ctcgacctct cgacgcgggc    240
cttcttcgga atctcgcccc gtgaggccgc cgccatggac ccgcagcagc gactggtcct    300
cgaactcgcc tgggaggcgc tggaggacgc cggaatcgtc cccggcaccc tcgccggaag    360
ccgcaccgcc gtcttcgtcg gcaccctgcg ggacgactac acgagcctcc tctaccagca    420
cggcgagcag gccatcaccc agcacaccat ggcgggcgtg aaccggggcg tcatcgccaa    480
ccgcgtctcg taccacctcg gcctgcaggg cccgagcctc accgtcgacg ccgcgcagtc    540
gtcctcgctc gtcgccgtgc acctggcctg cgagtccctg cgcgccgggg agtccacgac    600
ggcgctcgtc gccggcgtga acctcaacat cctcgcggag agcgccgtga cggaggagcg    660
cttcggtgga ctctccccgg acggcaccgc ctacaccttc gacgcgcggg ccaacggatt    720
cgtccggggc gagggcggcg gagtcgtcgt actcaagccg ctctcccgcg ccctcgccga    780
cggcgaccgt gtccacggcg tcatccgcgc cagcgccgtc aacaacgacg gagccacccc    840
gggtctcacc gtgcccagca gggccgccca ggagaaggtg ctgcgcgagg cgtaccggaa    900
ggcggccctg gacccgtccg ccgtccagta cgtcgaactc cacggcaccg gaacccccgt    960
cggcgacccc atcgaggccg ccgcgctcgg cgccgtcctc ggctcggcgc gccccgcgga   1020
cgaaccctg ctcgtcggct cggccaagac gaacgtcggg cacctcgaag gcgccgccgg   1080
catcgtcggc ctcatcaaga cgctcctcgc gctcggccgg cgccggatcc cggcgagcct   1140
caacttccgt acgccccacc cggacatccc gctcgacacc ctcggcgtcg acgtgcccga   1200
cggcctgcgg gagtggccgc acccggaccg cgaactcctc gccggcgtca gctcgttcgg   1260
catgggcggc accaacgccc acgtcgtcct cagcgaaggc cccgcccagg gcggcgagca   1320
gcccggcatc gatgaggaga cccccgtcga cagcggggcc gcactgccct tcgtcgtcac   1380
cggccgcggc ggcgaggccc tgcgcgccca ggcccggcgc ctgcacgagg ccgtcgaagc   1440
ggacccggag ctcgcgcccg ccgcactcgc ccggtcgctg gtcaccaccc gtacggtctt   1500
cacgcaccgg tcggtcgtcc tcgccccgga ccgcgcccgc ctcctcgacg gcctcggcgc   1560
cctcgccgcc gggacgcccg cgcccggcgt ggtcaccggc accccgccc ccgggcgcct   1620
cgccgtcctg ttcagcggcc agggtgccca acgtacgggc atgggcatgg agttgtacgc   1680
cgcccacccc gccttcgcga cggccttcga cgccgtcgcc gccgaactgg accccctcct   1740
cgaccggccc ctcgccgaac tcgtcgcggc gggcgacacc ctcgaccgca ccgtccacac   1800
```

-continued

| | |
|---|---|
| acagcccgcg ctcttcgccg tggaggtcgc cctccaccgc ctcgtcgagt cctgggcgt | 1860 |
| cacgcccgac ctgctcgccg gccactccgt cggcgagatc agcgccgccc acgtcgccgg | 1920 |
| ggtcctgtcg ctgcgcgacg ccgcccgcct cgtcgcggcg cgcggccgcc tcatgcaggc | 1980 |
| gctccccgag ggcggcgcga tggtcgcggt cgaggcgagc gaggaggaag tgcttccgca | 2040 |
| cctcgcggga cgcgagcggg agctctccct cgcggccgtg aacggccccc gcgcggtcgt | 2100 |
| cctcgcgggc gccgagcgcg ccgtcctcga cgtcgccgag ctgctgcgcg aacagggccg | 2160 |
| ccggacgaag cggctcagcg tctcgcacgc cttccactcg ccgctcatgg agccgatgct | 2220 |
| cgacgacttc cgccgggtcg tcgaagagct ggacttccag gagccccgcg tcgacgtcgt | 2280 |
| gtccacggtg acgggcctgc ctgtcacagc gggccaatgg accgatcccg agtactgggt | 2340 |
| ggaccaggtc cgcaggcccg tacgcttcct cgacgccgta cgcaccctgg aggaatcggg | 2400 |
| cgccgacacc ttcctggagc tcggtcccga cggggtctgc tccgcgatgg cggcggactc | 2460 |
| cgtacgcgac caggaggccg ccacggcggt ctccgccctg cgcaagggcc gcccggagcc | 2520 |
| ccagtcgctg ctcgccgcac tcaccaccgt cttcgtccgg ggccacgacg tcgactggac | 2580 |
| cgccgcgcac gggagcaccg gcacggtcag ggtgcccctg ccgacctacg ccttccagcg | 2640 |
| cgaacgccac tggttcgacg cgccgcgcg aacggcggcg ccgctcacgg cgggccgatc | 2700 |
| gggcaccggt gcggcaccg gcccggccgc gggtgtgacg tcgggcgagg gcgagggcga | 2760 |
| gggcgagggc gcggtgcgg gtggcggtga tcggccggct cgccacgaga cgaccgagcg | 2820 |
| cgtgcgcgca cacgtcgccg ccgtcctcga gtacgacgac ccgacccgcg tcgaactcgg | 2880 |
| cctcaccttc aaggagctgg gcttcgactc cctcatgtcc gtcgagctgc ggaacgcgct | 2940 |
| cgtcgacgac acgggactgc gcctgcccag cggactgctc ttcgaccacc cgacgccgcg | 3000 |
| cgccctcgcc gcccacctgg gcgacctgct caccggcggc agcggcgaga ccggatcggc | 3060 |
| cgacgggata ccgccgcga ccccggcgga caccaccgcc gagcccatcg cgatcatcgg | 3120 |
| catggcctgc cgctacccg gcggcgtcac ctcccccgag acctgtggc ggctcgtcgc | 3180 |
| cgaggggcgc gacgccgtct cggggctgcc caccgaccgc ggctgggacg aggacctctt | 3240 |
| cgacgccgac cccgaccgca gcggcaagag ctcggtccgc gagggcggat tcctgcacga | 3300 |
| cgccgccctg ttcgacgccg gcttcttcgg gatatcgccc cgcgaggccc tcggcatgga | 3360 |
| cccgcagcag cggctgctcc tggagacggc atgggaggcc gtggagcgcg cagggctcga | 3420 |
| ccccgaaggc ctcaagggca gccggacggc cgtcttcgtc ggcgccaccg ccctggacta | 3480 |
| cggcccgcgc atgcacgacg gcgccgaggg cgtcgagggc cacctcctga ccgggaccac | 3540 |
| gcccagcgtg atgtcgggcc gcatcgccta ccagctcggc ctcaccggtc ctgcggtcac | 3600 |
| cgtcgacacg gcctgctcgt cctcgctcgt cgcgctgcac ctggccgtcc gttcgctgcg | 3660 |
| gcagggcgag tcgagcctcg cgctcgccgg cggagcgacc gtcatgtcga caccgggcat | 3720 |
| gttcgtcgag ttctcgcggc agcgcggcct cgccgccgac ggccgctcca aggccttctc | 3780 |
| cgactccgcc gacggcacct cctgggccga gggcgtcggc ctcctcgtcg tcgagcggct | 3840 |
| ctcggacgcc gagcgcaacg gccacccgt gctcgccgtg atccggggca gcgcggtcaa | 3900 |
| ccaggacggc gcctccaacg ggctcaccgc ccccaacggc ccgtcccagc agcgcgtcat | 3960 |
| ccgacaggcc ctggccgacg ccgggctcac cccgccgac gtcgacgccg tcgaggcgca | 4020 |
| cggtacgggt acccggctcg cgacccccat cgaggccgag cgatcctcg cacctacgg | 4080 |
| ccgggaccgg ggcgagggcg ctccgctcca gctcggctcg ctgaagtcga acatcggcca | 4140 |
| cgcgcaggcc gccgcgggcg tgggcgggct catcaagatg gtcctcgcga tgcgccacgg | 4200 |

-continued

```
cgtcctgccc aggacgctcc acgtggaccg gcccaccacc cgcgtcgact gggaggccgg    4260
cggcgtcgag ctcctcaccg aggagcggga gtggccggag acgggccgcc cgcgccgcgc    4320
ggcgatctcc tccttcggca tcagcggcac caacgcccac atcgtggtcg aacaggcccc    4380
ggaagccggg gaggcggcgg tcaccaccac cgcccggaa gcaggggaag ccggggaagc     4440
ggcggacacc accgccacca cgacgccggc cgcggtcggc gtccccgaac ccgtacgcgc    4500
ccccgtcgtg gtctccgcgc gggacgccgc cgccctgcgc gccaggccg ttcggctgcg     4560 gaccttcctc gacggccgac cggacgtcac cgtcgccgac ctcggacgct cgctggccgc    4620
ccgtaccgcc ttcgagcaca aggccgccct caccaccgcc accagggacg agctgctcgc    4680
cgggctcgac gccctcggcc gcggggagca agccacgggc ctggtcaccg gcgaaccggc    4740
cagggccgga cgcacggcct tcctgttcac cggccaggga gcgcagcgcg tcgccatggg    4800
cgaggaactg cgcgccgcgc accccgtgtt cgccgccgcc ctcgacaccg tgtacgcggc    4860
cctcgaccgt cacctcgacc ggccgctgcg ggagatcgtc gccgccgggg aggagctgga    4920
cctcaccgcg tacacccagc ccgccctctt cgccttcgag gtggcgctgt tccgcctcct    4980
cgaacaccac ggcctcgtcc ccgacctgct caccggccac tccgtcggcg agatcgccgc    5040
cgcgcacgtc gccggtgtcc tctccctcga cgacgccgca cgtctcgtca ccgcccgcgg    5100
ccggctcatg cagtcggccc gcgagggcgg cgcgatgatc gccgtgcagg cgggcgaggc    5160
cgaggtcgtc gagtccctga agggctacga gggcagggtc gccgtcgccg ccgtcaacgg    5220
acccaccgcc gtggtcgtct ccggcgacgc ggacgccgcc gaggagatcc gcgccgtatg    5280
ggcgggacgg ggccggcgca cccgcaggct gcgcgtcagc cacgccttcc actccccgca    5340
catggacgac gtcctcgacg agttcctccg ggtcgccgag ggcctgacct cgaggagcc     5400 gcggatcccc gtcgtctcca cggtcaccgg cgcgctcgtc acgtccggcg agctcacctc    5460
gcccgcgtac tgggtcgacc agatccggcg gcccgtgcgc ttcctggacg ccgtccgcac    5520
cctggccgcc caggacgcga ccgtcctcgt cgagatcggc cccgacgccg tcctcacggc    5580
actcgccgag gaggctctcg cgcccggcac ggacgccccg gacgcccggg acgtcacggt    5640
cgtcccgctg ctgcgcgcgg ggcgcccga gcccgagacc ctcgccgccg gtctcgcgac     5700
cgcccatgtc cacggcgcac ccttggaccg ggcgtcgttc ttcccggacg ggcgccgcac    5760
ggacctgccc acgtacgcct tccggcgcga gcactactgg ctgacgcccg aggcccgtac    5820
ggacgcccgc gcactcggct tcgacccggc gcggcacccg ctgctgacga ccacggtcga    5880
ggtcgccggc ggcgacggcg tcctgctgac cggccgtctc tccctgaccg accagccctg    5940
gctggccgac cacatggtca acggcgccgt cctgttgccg gccaccgcct tcctggagct    6000
cgccctcgcg gcgggcgacc acgtcggggc ggtccgggtg gaggaactca ccctcgaagc    6060
gccgctcgtc ctgcccgagc ggggcgccgt ccgcatccag gtcggcgtga gcggcgacgg    6120
cgagtcgccg gccgggcgca ccttcggtgt gtacagcacc cccgactccg gcgacaccgg    6180
tgacgacgcg ccccggggagt ggaccgccg tgtctccggc gtactcggcg aaggggaccc    6240
ggccacggag tcgaccacc ccggcaccga cggggacggt tcagcggcct ggccgcctgc     6300
ggcggcgacc gccacacccc tcgacggcgt ctacgaccgg ctcgcggagc tcggctacgg    6360
atacggtccg gccttccagg gctgacgggg ctgtggcgc gacggcgccg acacgctcgc     6420
cgagatccgg ctgcccgcgg cgcagcacga gagcgcgggg ctcttcggcg tacacccggc    6480
gctgctcgac gcggcgctcc acccgatcgt cctggagggc aactcagctg ccggtgcctg    6540
```

-continued

```
tgacgccgat accgacgcga ccgaccggat ccggctgccg ttcgcgtggg cggggtgac      6600 cctccacgcc gaaggggcca ccgcgctccg cgtacggatc acacccaccg gcccggacac    6660
ggtcacgctc cgcctcaccg acaccaccgg tgcgcccgtg gccaccgtgg agtccctgac    6720
cctgcgcgcg gtggcgaagg accggctggg caccaccgcc gggcgcgtcg acgacgccct    6780
gttcacggtc gtgtggacgg agaccggcac accggaaccc gcaggcgcg gagccgtgga    6840 ggtcgaggaa ctcgtcgacc tcgccggcct cggcgacctc gtggagctcg cgccgcgga    6900 cgtcgtcctc cgggccgacc gctggacgct cgacggggac ccgtccgccg ccgcgcgcac    6960
agccgtccgg cgcaccctcg ccatcgtcca ggagttcctg tccgagccgc gcttcgacgg    7020
ctcgcgactg gtgtgcgtca ccaggggcgc ggtcgccgca ctccccggcg aggacgtcac    7080
ctccctcgcc accggccccc tctggggcct cgtccgctcc gcccagtccg agaacccggg    7140
acgcctgttc ctcctggacc tgggtgaagg cgaaggcgag cgcgacgag ccgaggagct    7200 gatccgcgcg ccacggccg gggacgagcc gcagctcgcg cacgggacg ccgactgct    7260 cgcgccgagg ctggcccgta ccgccgccct ttcgagtgag acaccgccg gcggcgccga    7320 ccgtttcggc cccgacggca ccgtcctcgt caccgggggc accggaggcc tcggagcgct    7380
cctcgcccgc cacctcgtgg agcgtcacgg ggtgcgccgg ctgctgctgg tgagccgccg    7440
cggggccgac gcccccggcg cggccgacct gggcgaggac ctcgcgggcc tcggcgcgga    7500
ggtggcgttc gccgccgccg acgccgccga ccgcgagagc ctggcgcggg cgatcgccac    7560
cgtgcccgcc gagcatccgc tgacggccgt cgtgcacacg gcgggagtcg tcgacgacgc    7620
gacggtggag gcgctcacac cggaacggct ggacgcggta ctgcgcccga aggtcgacgc    7680
cgcgtggaac ctgcacagagc tcaccaagga cctgcgcctc gacgccttcg tcctcttctc    7740
ctccgtctcc ggcatcgtcg gcaccgccgg ccaggccaac tacgcggcgg ccaacacggg    7800
cctcgacgcc ctcgccgccc accgcgccgc cacgggcctg gccgccacgt cgctggcctg    7860
gggcctctgg gacggcacgc acggcatggg cggcacgctc ggcgccgccg acctcgcccg    7920
ctggagccgg gccggaatca ccccgctcac cccgctgcag gcctcgcgc tcttcgacgc    7980 cgcggtcgcc agggacgacg ccctcctcgt acccgccggg ctccgtccca ccgcccaccg    8040
gggcacggac ggacagcctc ctgcgctgtg gcgcggcctc gtccgggcgc gcccgcgccg    8100
tgccgcgcgg acggccgccg aggcggcgga cacgaccggc ggctggctga gcgggctcgc    8160
cgcacagtcc cccgaggagc ggcgcagcac agccgtcacg ctcgtgacgg gtgtcgtcgc    8220
ggacgtcctc gggcacgccg actccgccgc ggtcggggcg gagcggtcct tcaaggacct    8280
cggcttcgac tccctggccg gggtggagct ccgcaaccgg ctgaacgccg ccaccggcct    8340
gcggctcccc gcgaccacgg tcttcgacca tccctcgccg gccgcgctcg cgtcccatct    8400
cctcgcccag gtgcccgggt tgaaggaggg gacggcggcg accgcgaccg tcgtggccga    8460
gcggggcgct tccttcggtg accgtgcgac cgacgacgat ccgatcgcga tcgtgggcat    8520
ggcatgccgc tatccgggtg gtgtgtcgtc gccggaggac ctgtggcggc tggtggccga    8580
ggggacggac gcgatcagcg agttccccgt caaccgcggc tgggacctgg agagcctcta    8640
cgacccggat cccgagtcga agggcaccac gtactgccgg gagggcgggt tcctggaagg    8700
cgccggtgac ttcgacgccg ccttcttcgg catctcgccg cgcgaggccc tggtgatgga    8760
cccgcagcag cggctgctgc tggaggtgtc ctgggaggcg ctggaacgcg cgggcatcga    8820
cccgtcctcg ctgcgcggca gccgcggtgg tgtctacgtg ggcgccgcgc acggctcgta    8880
cgcctccgat ccccggctgg tgcccgaggg ctcggagggc tatctgctga ccggcagcgc    8940
```

-continued

```
cgacgcggtg atgtccggcc gcatctccta cgcgctcggt ctcgaaggac cgtccatgac   9000
ggtggagacg gcctgctcct cctcgctggt ggcgctgcat ctggcggtac gggcgctgcg   9060
gcacggcgag tgcgggctcg cgctggcggg cggggtggcg gtgatggccg atccggcggc   9120
gttcgtggag ttctccccgg cagaagggggct ggccgccgac ggccgctgca aggcgttctc   9180
ggccgccgcc gacggcaccg gctgggccga gggcgtcggc gtgctcgtcc tggagcggct   9240
gtcggacgcg cgccgcgcgg ggcacacggt cctcggcctg gtcaccggca ccgcggtcaa   9300
ccaggacggt gcctccaacg ggctgaccgc gcccaacggc ccagcccagc aacgcgtcat   9360
cgccgaggcg ctcgccgacg ccgggctgtc cccggaggac gtggacgcgg tcgaggcgca   9420
cggcaccggc acccggctcg cgacccccat cgaggccggg gcgctgctcg ccgcctccgg   9480
acggaaccgt tccggcgacc acccgctgtg gctcggctcg ctgaagtcca acatcgggca   9540
tgcccaggcc gccgccggtg tcggcggcgt catcaagatg ctccaggcgc tgcggcacgg   9600
cttgctgccc cgcaccctcc acgccgacga gccgaccccg catgccgact ggagctccgg   9660
ccgggtacgg ctgctcacct ccgaggtgcc gtggcagcgg accggccggc cccggcggac   9720
cggggtgtcc gccttcggcg tcggcggcac caatgcccat gtcgtcctcg aagaggcacc   9780
cgccccgccc gcgccggaac cggccgggga gccccccggc ggctcccgcg ccgcagaagg   9840
ggcggaaggg cccctggcct gggtggtctc cggacgcgac gagccggccc tgcggtccca   9900
ggcccggcgg ctccgcgacc acctctcccg cacccccggg gcccgccgc gtgacatcgc   9960 cttctccctc gccgccacgc gcgcagcctt tgaccaccgc gccgtgctga tcggctcgga  10020
cggggccgaa ctcgccgccg ccctggacgc gttggccgaa ggacgcgacg gtccggcggt  10080
ggtgcgcgga gtccgcgacc gggacggcag gatggccttc ctcttcaccg gcagggcag  10140 ccagcgcgcc gggatggccc acgacctgca tgccgcccat accttcttcg cgtccgccct  10200
cgacgaggtg acggaccgtc tcgacccgct gctcggccgg ccgctcggcg cgctgctgga  10260
cgcccgaccc ggctcgcccg aagcggcact cctggaccgg accgagtaca cccagccggc  10320
gctcttcgcc gtcgaggtgg cgctccaccg gctgctggag cactggggga tgcgccccga  10380
cctgctgctg gggcactcgg tgggcgaact ggcggccgcc cacgtcgcgg gtgtgctcga  10440
tctcgacgac gcctgcgcgc tggtggccgc ccgcggcagg ctgatgcagc gcctgccgcc  10500
cggcggcgcg atggtctccg tgcgggccgg cgaggacgag gtccgcgcac tgctggccgg  10560
ccgcgaggac gccgtctgcg tcgccgcggt gaacggcccc cggtcggtgg tgatctccgg  10620
cgcggaggaa gcggtggccg aggcggcggc gcagctcgcc ggacgaggcc gccgcaccag  10680
gcggctccgc gtcgcgcacg ccttccactc accccctgatg gacggcatgc tcgccggatt  10740
ccgggaggtc gccgccggcc tgcgctaccg ggaaccggag ctgacggtcg tctccacggt  10800
cacggggcgg ccgcccgcc ccggtgaact caccggcccc gactactggg tggcccaggt  10860
ccgtgagccc gtgcgcttcg cggacgcggt ccgcacggca caccgcctcg agcccgcac  10920 cttcctggag accggcccgg acggcgtgct gtgcggcatg gcagaggagt gcctggagga  10980
cgacaccgtg gccctgctgc cggcgatcca caagcccggc accgcgccgc acggtccggc  11040 ggctccggc gcgctgcggg cggccgccgc gcgtacggc cggggcgccc gggtggactg  11100
ggccgggatg cacgccgacg gccccgaggg gccggcccgc gcgtcgaac tgcccgtcca  11160 cgccttccgg caccgccgct actggctcgc cccgggccgg cgggcggaca ccgacgactg  11220
gatgtaccgg atcggctggg accggctgcc ggctgtgacc ggcgggcccc ggaccgccgg  11280
```

```
ccgctggctg gtgatccacc ccgacagccc gcgctgccgg gagctgtccg gccacgccga   11340
acgcgcgctg cgcgccgcgg gcgcgagccc cgtaccgctg cccgtggacg ctccggccgc   11400
cgaccgggcg tccttcgcgg cactgctgcg ctccgccacc ggacctgaca cacgaggtga   11460
cacagccgcg cccgtggccg gtgtgctgtc gctgctgtcc gaggaggatc ggccccatcg   11520
ccagcacgcc ccggtacccg ccggggtcct ggcgacgctg tccctgatgc aggctatgga   11580
ggaggaggcg gtggaggctc gcgtgtggtg cgtctcccgc gccgcggtcg ccgccgccga   11640
ccgggaacgg cccgtcggcg cgggcgccgc cctgtggggg ctgggcgggg tggccgccct   11700
ggaacgcccc acccggtggg gcggtctcgt ggacctgccc gcctcgcccg gtgcggcgca   11760
ctgggcggcc gccgtggaac ggctcgccgg tcccgaggac cagatcgccg tgcgcgcgtc   11820
cggcagttgg ggccggcgcc tcaccaggct gccgcgcgac ggcggcggcc ggacggccgc   11880
acccgcgtac cggccgcgcg cacggtgctc cgtcaccggt ggcaccggcg cgctcggcgg   11940
gcatctcgcc cgctggctcg ccgcggcggg cgccgaacac ctggcgctca ccagccgccg   12000
gggcccggac gcgcccggcg ccgccggact cgaggccgaa ctcctcctcc tgggcgccaa   12060
ggtgacgttc gccgcctgcg acaccgccga ccgcgacggc ctcgcccggg tcctgcgggc   12120
gataccggag gacaccccgc tcaccgcggt gttccacgcc gcgggcgtac cgcaggtcac   12180
gccgctgtcc cgtacctcgc ccgagcactt cgccgacgtg tacgcgggca aggcggcggg   12240
cgccgcgcac ctggacgaac tgacccgcga actcggcgcc ggactcgacg cgttcgtcct   12300
ctactcctcc ggcgccggcg tctggggcag cgccggccag ggtgcctacg ccgccgccaa   12360
cgccgccctg gacgcgctcg cccggcgccg tgcggcggac ggactccccg ccacctccat   12420
cgcctggggc gtgtggggcg gcggcggtat ggggccgac gaggcgggcg cggagtatct   12480
gggccggcgc ggtatgcgcc ccatggcacc ggtctccgcg ctccgggcga tggccaccgc   12540
catcgcctcc ggggaacccct gccccaccgt cacccacacc gactgggagc gcttcggcga   12600
gggcttcacc gccttccggc ccagccctct gatcgcgggg ctcggcacgc cggcggcgg   12660
ccgggcggcg gagaccccg aggagggaa cgccaccgct gcggcggacc tcaccgcccc   12720
gccgccgcc gaactccgca ccgcgctgcg cgagctggtg cgagcccgga ccgccgcggc   12780
gctcggcctc gacgacccgg ccgaggtcgc gagggcgaa cggttccccg ccatgggctt   12840
cgactccctg gccaccgtac ggctgcgccg cggactcgcc tcgccacgg gcctcgacct   12900
gccccccgat ctgctcttcg accgggacac cccggccgcg ctcgccgccc acctggccga   12960
actgctcgcc accgcacggg accacggacc cggcggcccc gggaccggtg ccgcgccggc   13020
cgatgccgga agcggcctgc cggccctcta ccggagggcc gtccgcaccg gccgggcgc   13080
ggaaatggcc gaactgctcg ccgccgcttc ccggttccgc cccgccttcg ggacggcgga   13140
ccggcagccg gtgccctcg tgccgctggc gacggcgcg gaggacaccg ggctcccgct   13200
gctcgtgggc tgcgccggga cggcggtggc ctccggcccg gtggagttca ccgccttcgc   13260
cggagcgctg gcgacctcc ggcggcgg cccgatggcc gcgctgccgc agcccggctt   13320
tctgccggga gaacgagtcc cggccacccc ggaggcattg ttcgaggccc aggcggaagc   13380
gctgctgcgc tacgcggccg ccggccctt cgtgctgctg ggcactccg ccggcgccaa   13440
catggcccac gccctgaccc gtcatctgga ggcgaacggt ggcggccccg cagggctggt   13500
gctcatggac atctacaccc ccgccgaccc cggcgcgatg ggcgtctggc ggaacgacat   13560
gttccagtgg gtctggcggc gctcggacat ccccccggac gaccaccgcc tcacggccat   13620
gggcgcctac caccggctgc ttctcgactg gtcgcccacc ccgtccgcg ccccgtact   13680
```

-continued

```
gcatctgcgc gccgcggaac ccatgggcga ctggccaccc ggggacaccg gctggcagtc    13740
ccactgggac ggcgcgcaca ccaccgccgg catccccgga aaccacttca cgatgatgac    13800
cgaacacgcc tccgccgccg cccggctcgt gcacggctgg ctcgcggaac ggaccccgtc    13860
cgggcagggc gggtcaccgt cccgcgcggc ggggagagag gagaggccgt gaacacggca    13920
gccggcccga ccgcaccgc cgccggcggc accaccgccc cggcggcggc acacgacctg     13980
tcccgcgccg gacgcaggct ccaactcacc cgggccgcac agtggttcgc cggcaaccag    14040
ggagacccct acgggatgat cctgcgcgcc ggcaccgccg accggcaccc gtacgaggaa    14100
gagatccccg ggtaccgagc tcgaattctt aattaaggag gtcgtag atg agt aac      14156
                                                    Met Ser Asn
                                                    1
```

```
aag aac aac gat gag ctg cag cgg cag gcc tcg gaa aac acc ctg ggg      14204
Lys Asn Asn Asp Glu Leu Gln Arg Gln Ala Ser Glu Asn Thr Leu Gly
    5                   10                  15 ctg aac ccg gtc atc ggt atc cgc cgc aaa gac ctg ttg agc tcg gca      14252
Leu Asn Pro Val Ile Gly Ile Arg Arg Lys Asp Leu Leu Ser Ser Ala
20                  25                  30                  35 cgc acc gtg ctg cgc cag gcc gtg cgc caa ccg ctg cac agc gcc aag      14300
Arg Thr Val Leu Arg Gln Ala Val Arg Gln Pro Leu His Ser Ala Lys
                40                  45                  50 cat gtg gcc cac ttt ggc ctg gag ctg aag aac gtg ctg ctg ggc aag      14348
His Val Ala His Phe Gly Leu Glu Leu Lys Asn Val Leu Leu Gly Lys
            55                  60                  65 tcc agc ctt gcc ccg gaa agc gac gac cgt cgc ttc aat gac ccg gca      14396
Ser Ser Leu Ala Pro Glu Ser Asp Asp Arg Arg Phe Asn Asp Pro Ala
        70                  75                  80 tgg agc aac aac cca ctt tac cgc cgc tac ctg caa acc tat ctg gcc      14444
Trp Ser Asn Asn Pro Leu Tyr Arg Arg Tyr Leu Gln Thr Tyr Leu Ala
    85                  90                  95 tgg cgc aag gag ctg cag gac tgg atc ggc aac agc gac ctg tcg ccc      14492
Trp Arg Lys Glu Leu Gln Asp Trp Ile Gly Asn Ser Asp Leu Ser Pro
100                 105                 110                 115 cag gac atc agc cgc ggc cag ttc gtc atc aac ctg atg acc gaa gcc      14540
Gln Asp Ile Ser Arg Gly Gln Phe Val Ile Asn Leu Met Thr Glu Ala
                120                 125                 130 atg gct ccg acc aac acc ctg tcc aac ccg gca gca gtc aaa cgc ttc      14588
Met Ala Pro Thr Asn Thr Leu Ser Asn Pro Ala Ala Val Lys Arg Phe
            135                 140                 145 ttc gaa acc ggc ggc aag agc ctg ctc gat ggc ctg tcc aac ctg gcc      14636
Phe Glu Thr Gly Gly Lys Ser Leu Leu Asp Gly Leu Ser Asn Leu Ala
        150                 155                 160 aag gac ctg gtc aac aac ggt ggc atg ccc agc cag gtg aac atg gac      14684
Lys Asp Leu Val Asn Asn Gly Gly Met Pro Ser Gln Val Asn Met Asp
165                 170                 175 gcc ttc gag gtg ggc aag aac ctg ggc acc agt gaa ggc gcc gtg gtg      14732
Ala Phe Glu Val Gly Lys Asn Leu Gly Thr Ser Glu Gly Ala Val Val
180                 185                 190                 195 tac cgc aac gat gtg ctg gag ctg atc cag tac aag ccc atc acc gag      14780
Tyr Arg Asn Asp Val Leu Glu Leu Ile Gln Tyr Lys Pro Ile Thr Glu
                200                 205                 210 cag gtg cat gcc cgc ccg ctg ctg gtg gtg ccg ccg cag atc aac aag      14828
Gln Val His Ala Arg Pro Leu Leu Val Val Pro Pro Gln Ile Asn Lys
            215                 220                 225 ttc tac gta ttc gac ctg agc ccg gaa aag agc ctg gca cgc tac tgc      14876
Phe Tyr Val Phe Asp Leu Ser Pro Glu Lys Ser Leu Ala Arg Tyr Cys
        230                 235                 240
```

| | | |
|---|---|---|
| ctg cgc tcg cag cag cag acc ttc atc atc agc tgg cgc aac ccg acc<br>Leu Arg Ser Gln Gln Gln Thr Phe Ile Ile Ser Trp Arg Asn Pro Thr<br>245                          250                           255 | 14924 |
| aaa gcc cag cgc gaa tgg ggc ctg tcc acc tac atc gac gcg ctc aag<br>Lys Ala Gln Arg Glu Trp Gly Leu Ser Thr Tyr Ile Asp Ala Leu Lys<br>260                          265                        270                    275 | 14972 |
| gag gcg gtc gac gcg gtg ctg gcg att acc ggc agc aag gac ctg aac<br>Glu Ala Val Asp Ala Val Leu Ala Ile Thr Gly Ser Lys Asp Leu Asn<br>                        280                        285                        290 | 15020 |
| atg ctc ggt gcc tgc tcc ggc ggc atc acc tgc acg gca ttg gtc ggc<br>Met Leu Gly Ala Cys Ser Gly Gly Ile Thr Cys Thr Ala Leu Val Gly<br>              295                        300                        305 | 15068 |
| cac tat gcc gcc ctc ggc gaa aac aag gtc aat gcc ctg acc ctg ctg<br>His Tyr Ala Ala Leu Gly Glu Asn Lys Val Asn Ala Leu Thr Leu Leu<br>                  310                        315                        320 | 15116 |
| gtc agc gtg ctg gac acc acc atg gac aac cag gtc gcc ctg ttc gtc<br>Val Ser Val Leu Asp Thr Thr Met Asp Asn Gln Val Ala Leu Phe Val<br>325                          330                        335 | 15164 |
| gac gag cag act ttg gag gcc gcc aag cgc cac tcc tac cag gcc ggt<br>Asp Glu Gln Thr Leu Glu Ala Ala Lys Arg His Ser Tyr Gln Ala Gly<br>340                          345                        350                    355 | 15212 |
| gtg ctc gaa ggc agc gag atg gcc aag gtg ttc gcc tgg atg cgc ccc<br>Val Leu Glu Gly Ser Glu Met Ala Lys Val Phe Ala Trp Met Arg Pro<br>                        360                        365                        370 | 15260 |
| aac gac ctg atc tgg aac tac tgg gtc aac aac tac ctg ctc ggc aac<br>Asn Asp Leu Ile Trp Asn Tyr Trp Val Asn Asn Tyr Leu Leu Gly Asn<br>                  375                        380                        385 | 15308 |
| gag ccg ccg gtg ttc gac atc ctg ttc tgg aac aac gac acc acg cgc<br>Glu Pro Pro Val Phe Asp Ile Leu Phe Trp Asn Asn Asp Thr Thr Arg<br>                        390                        395                        400 | 15356 |
| ctg ccg gcc gcc ttc cac ggc gac ctg atc gaa atg ttc aag agc aac<br>Leu Pro Ala Ala Phe His Gly Asp Leu Ile Glu Met Phe Lys Ser Asn<br>405                          410                        415 | 15404 |
| ccg ctg acc cgc ccg gac gcc ctg gag gtt tgc ggc act ccg atc gac<br>Pro Leu Thr Arg Pro Asp Ala Leu Glu Val Cys Gly Thr Pro Ile Asp<br>420                          425                        430                    435 | 15452 |
| ctg aaa cag gtc aaa tgc gac atc tac agc ctt gcc ggc acc aac gac<br>Leu Lys Gln Val Lys Cys Asp Ile Tyr Ser Leu Ala Gly Thr Asn Asp<br>                  440                        445                    450 | 15500 |
| cac atc acc ccg tgg cag tca tgc tac cgc tcg gcg cac ctg ttc ggc<br>His Ile Thr Pro Trp Gln Ser Cys Tyr Arg Ser Ala His Leu Phe Gly<br>                        455                        460                    465 | 15548 |
| ggc aag atc gag ttc gtg ctg tcc aac agc ggc cac atc cag agc atc<br>Gly Lys Ile Glu Phe Val Leu Ser Asn Ser Gly His Ile Gln Ser Ile<br>                  470                        475                    480 | 15596 |
| ctc aac ccg cca ggc aac ccc aag gcg cgc ttc atg acc ggt gcc gat<br>Leu Asn Pro Pro Gly Asn Pro Lys Ala Arg Phe Met Thr Gly Ala Asp<br>485                          490                        495 | 15644 |
| cgc ccg ggt gac ccg gtg gcc tgg cag gaa aac gcc acc aag cat gcc<br>Arg Pro Gly Asp Pro Val Ala Trp Gln Glu Asn Ala Thr Lys His Ala<br>500                          505                        510                    515 | 15692 |
| gac tcc tgg tgg ctg cac tgg caa agc tgg ctg ggc gag cgt gcc ggc<br>Asp Ser Trp Trp Leu His Trp Gln Ser Trp Leu Gly Glu Arg Ala Gly<br>                  520                        525                    530 | 15740 |
| gag ctg gaa aag gcg ccg acc cgc ctg ggc aac cgt gcc tat gcc gct<br>Glu Leu Glu Lys Ala Pro Thr Arg Leu Gly Asn Arg Ala Tyr Ala Ala<br>535                          540                        545 | 15788 |
| ggc gag gca tcc ccg ggc acc tac gtt cac gag cgt tgagctgcag<br>Gly Glu Ala Ser Pro Gly Thr Tyr Val His Glu Arg<br>550                          555 | 15834 | cgccgtggcc acctgcggga cgccacggtg ttgaattc       15872

<210> SEQ ID NO 4
<211> LENGTH: 559
<212> TYPE: PRT
<213> ORGANISM: Streptomyces venezuelae

<400> SEQUENCE: 4

```
Met Ser Asn Lys Asn Asn Asp Glu Leu Gln Arg Gln Ala Ser Glu Asn
  1               5                  10                  15

Thr Leu Gly Leu Asn Pro Val Ile Gly Ile Arg Arg Lys Asp Leu Leu
                 20                  25                  30

Ser Ser Ala Arg Thr Val Leu Arg Gln Ala Val Arg Gln Pro Leu His
             35                  40                  45

Ser Ala Lys His Val Ala His Phe Gly Leu Glu Leu Lys Asn Val Leu
         50                  55                  60

Leu Gly Lys Ser Ser Leu Ala Pro Glu Ser Asp Asp Arg Arg Phe Asn
 65                  70                  75                  80

Asp Pro Ala Trp Ser Asn Asn Pro Leu Tyr Arg Arg Tyr Leu Gln Thr
                 85                  90                  95

Tyr Leu Ala Trp Arg Lys Glu Leu Gln Asp Trp Ile Gly Asn Ser Asp
                100                 105                 110

Leu Ser Pro Gln Asp Ile Ser Arg Gly Gln Phe Val Ile Asn Leu Met
            115                 120                 125

Thr Glu Ala Met Ala Pro Thr Asn Thr Leu Ser Asn Pro Ala Ala Val
        130                 135                 140

Lys Arg Phe Phe Glu Thr Gly Gly Lys Ser Leu Leu Asp Gly Leu Ser
145                 150                 155                 160

Asn Leu Ala Lys Asp Leu Val Asn Asn Gly Gly Met Pro Ser Gln Val
                165                 170                 175

Asn Met Asp Ala Phe Glu Val Gly Lys Asn Leu Gly Thr Ser Glu Gly
                180                 185                 190

Ala Val Val Tyr Arg Asn Asp Val Leu Glu Leu Ile Gln Tyr Lys Pro
            195                 200                 205

Ile Thr Glu Gln Val His Ala Arg Pro Leu Leu Val Val Pro Pro Gln
        210                 215                 220

Ile Asn Lys Phe Tyr Val Phe Asp Leu Ser Pro Glu Lys Ser Leu Ala
225                 230                 235                 240

Arg Tyr Cys Leu Arg Ser Gln Gln Gln Thr Phe Ile Ile Ser Trp Arg
                245                 250                 255

Asn Pro Thr Lys Ala Gln Arg Glu Trp Gly Leu Ser Thr Tyr Ile Asp
                260                 265                 270

Ala Leu Lys Glu Ala Val Asp Ala Val Leu Ala Ile Thr Gly Ser Lys
            275                 280                 285

Asp Leu Asn Met Leu Gly Ala Cys Ser Gly Gly Ile Thr Cys Thr Ala
        290                 295                 300

Leu Val Gly His Tyr Ala Ala Leu Gly Glu Asn Lys Val Asn Ala Leu
305                 310                 315                 320

Thr Leu Leu Val Ser Val Leu Asp Thr Thr Met Asp Asn Gln Val Ala
                325                 330                 335

Leu Phe Val Asp Glu Gln Thr Leu Glu Ala Ala Lys Arg His Ser Tyr
                340                 345                 350

Gln Ala Gly Val Leu Glu Gly Ser Glu Met Ala Lys Val Phe Ala Trp
            355                 360                 365
```

```
Met Arg Pro Asn Asp Leu Ile Trp Asn Tyr Trp Val Asn Asn Tyr Leu
    370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Met Phe
                405                 410                 415

Lys Ser Asn Pro Leu Thr Arg Pro Asp Ala Leu Glu Val Cys Gly Thr
                420                 425                 430

Pro Ile Asp Leu Lys Gln Val Lys Cys Asp Ile Tyr Ser Leu Ala Gly
            435                 440                 445

Thr Asn Asp His Ile Thr Pro Trp Gln Ser Cys Tyr Arg Ser Ala His
    450                 455                 460

Leu Phe Gly Gly Lys Ile Glu Phe Val Leu Ser Asn Ser Gly His Ile
465                 470                 475                 480

Gln Ser Ile Leu Asn Pro Pro Gly Asn Pro Lys Ala Arg Phe Met Thr
                485                 490                 495

Gly Ala Asp Arg Pro Gly Asp Pro Val Ala Trp Gln Glu Asn Ala Thr
                500                 505                 510

Lys His Ala Asp Ser Trp Trp Leu His Trp Gln Ser Trp Leu Gly Glu
            515                 520                 525

Arg Ala Gly Glu Leu Glu Lys Ala Pro Thr Arg Leu Gly Asn Arg Ala
    530                 535                 540

Tyr Ala Ala Gly Glu Ala Ser Pro Gly Thr Tyr Val His Glu Arg
545                 550                 555
```